(12) United States Patent
Huang et al.

(10) Patent No.: US 8,453,906 B2
(45) Date of Patent: Jun. 4, 2013

(54) SURGICAL INSTRUMENTS WITH ELECTRODES

(75) Inventors: Zhifan F. Huang, Mason, OH (US);
Jason L. Harris, Mason, OH (US);
Prasanna Malaviya, Mason, OH (US);
Foster B. Stulen, Mason, OH (US);
Jeffrey S. Swayze, Hamilton, OH (US);
Scott A. Woodruff, Cincinnati, OH (US); Gwendolyn P. Payne, Cincinnati, OH (US); Donna L. Korvick, Maineville, OH (US); David K. Norvell, Monroe, OH (US); Aron O. Zingman, Cincinnati, OH (US); Paul Guerra, Los Gatos, CA (US); Mary E. Mootoo, Cincinnati, OH (US); Jeffrey L. Aldridge, Lebanon, OH (US); Timothy G. Dietz, Terrace Park, OH (US); David A. Witt, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 390 days.

(21) Appl. No.: 12/836,383

(22) Filed: Jul. 14, 2010

(65) Prior Publication Data
US 2012/0012638 A1    Jan. 19, 2012

(51) Int. Cl.
*A61B 17/068* (2006.01)

(52) U.S. Cl.
USPC .... 227/176.1; 227/19; 227/175.2; 227/180.1; 606/139; 606/219

(58) Field of Classification Search
USPC .............. 227/19, 175.1, 176.1, 175.2, 178.1, 227/180.1; 606/139, 143, 151, 153, 219
See application file for complete search history.

(56) References Cited

U.S. PATENT DOCUMENTS

| 2,366,274 A | 1/1945 | Luth et al. |
| 2,458,152 A | 1/1949 | Eakins |

(Continued)

FOREIGN PATENT DOCUMENTS

| DE | 20004812 U1 | 9/2000 |
| DE | 10201569 A1 | 7/2003 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Scott A. Smith

(57) ABSTRACT

An end-effector assembly configured to be attached to a surgical instrument. The end-effector assembly comprises a first jaw and a second jaw comprising a staple cavity. At least one of the first jaw and the second jaw is movable relative to the other jaw. The end-effector assembly comprises a staple removably positioned within the staple cavity and an electrically-conductive driver configured to move the staple between a first stored position in which the staple is at least partially positioned within the staple cavity and a second position in which the staple is at least partially deployed from the staple cavity into tissue positioned intermediate the first jaw and the second jaw. The staple comprises an electrode.

24 Claims, 52 Drawing Sheets

U.S. PATENT DOCUMENTS

| | | | |
|---|---|---|---|
| 2,510,693 A | 6/1950 | Green | |
| 3,166,971 A | 1/1965 | Stoecker | |
| 3,580,841 A | 5/1971 | Cadotte et al. | |
| 3,703,651 A | 11/1972 | Blowers | |
| 4,005,714 A | 2/1977 | Hiltebrandt | |
| 4,058,126 A | 11/1977 | Leveen | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,545,926 A | 10/1985 | Fouts, Jr. et al. | |
| 4,582,236 A | 4/1986 | Hirose | |
| 4,761,871 A | 8/1988 | O'Connor et al. | |
| 4,849,133 A | 7/1989 | Yoshida et al. | |
| 4,910,389 A | 3/1990 | Sherman et al. | |
| 5,104,025 A | 4/1992 | Main et al. | |
| 5,106,538 A | 4/1992 | Barma et al. | |
| 5,108,383 A | 4/1992 | White | |
| 5,205,459 A | 4/1993 | Brinkerhoff et al. | |
| 5,285,945 A | 2/1994 | Brinkerhoff et al. | |
| 5,309,927 A | 5/1994 | Welch | |
| 5,387,207 A | 2/1995 | Dyer et al. | |
| 5,389,098 A * | 2/1995 | Tsuruta et al. | 606/41 |
| 5,395,312 A | 3/1995 | Desai | |
| 5,403,312 A | 4/1995 | Yates et al. | |
| 5,428,504 A | 6/1995 | Bhatla | |
| 5,496,317 A | 3/1996 | Goble et al. | |
| 5,504,650 A | 4/1996 | Katsui et al. | |
| 5,511,556 A | 4/1996 | DeSantis | |
| 5,522,839 A | 6/1996 | Pilling | |
| 5,558,671 A | 9/1996 | Yates | |
| 5,563,179 A | 10/1996 | Stone et al. | |
| 5,599,350 A | 2/1997 | Schulze et al. | |
| 5,624,452 A | 4/1997 | Yates | |
| 5,647,871 A | 7/1997 | Levine et al. | |
| 5,665,085 A | 9/1997 | Nardella | |
| 5,665,100 A | 9/1997 | Yoon | |
| 5,674,220 A | 10/1997 | Fox et al. | |
| 5,688,270 A | 11/1997 | Yates et al. | |
| 5,693,051 A | 12/1997 | Schulze et al. | |
| 5,709,680 A | 1/1998 | Yates et al. | |
| 5,716,366 A | 2/1998 | Yates | |
| 5,735,848 A | 4/1998 | Yates et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,797,941 A | 8/1998 | Schulze et al. | |
| 5,800,432 A | 9/1998 | Swanson | |
| 5,807,393 A | 9/1998 | Williamson, IV et al. | |
| 5,810,811 A * | 9/1998 | Yates et al. | 606/50 |
| 5,817,033 A | 10/1998 | DeSantis et al. | |
| 5,817,093 A * | 10/1998 | Williamson et al. | 606/50 |
| 5,880,668 A | 3/1999 | Hall | |
| 5,906,625 A | 5/1999 | Bito et al. | |
| 5,984,938 A | 11/1999 | Yoon | |
| 6,003,517 A | 12/1999 | Sheffield et al. | |
| 6,013,052 A | 1/2000 | Durman et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,099,550 A | 8/2000 | Yoon | |
| H1904 H | 10/2000 | Yates et al. | |
| 6,206,876 B1 | 3/2001 | Levine et al. | |
| 6,292,700 B1 | 9/2001 | Morrison et al. | |
| 6,340,878 B1 | 1/2002 | Oglesbee | |
| H2037 H | 7/2002 | Yates et al. | |
| 6,443,968 B1 | 9/2002 | Holthaus et al. | |
| 6,464,702 B2 | 10/2002 | Schulze et al. | |
| 6,500,176 B1 | 12/2002 | Truckai et al. | |
| 6,503,248 B1 | 1/2003 | Levine | |
| 6,514,252 B2 | 2/2003 | Nezhat et al. | |
| 6,517,565 B1 * | 2/2003 | Whitman et al. | 606/219 |
| 6,533,784 B2 | 3/2003 | Truckai et al. | |
| 6,554,829 B2 | 4/2003 | Schulze et al. | |
| 6,558,376 B2 | 5/2003 | Bishop | |
| 6,572,639 B1 | 6/2003 | Ingle et al. | |
| 6,575,969 B1 | 6/2003 | Rittman, III et al. | |
| 6,589,200 B1 | 7/2003 | Schwemberger et al. | |
| 6,602,252 B2 | 8/2003 | Mollenauer | |
| 6,635,057 B2 | 10/2003 | Harano et al. | |
| 6,656,177 B2 | 12/2003 | Truckai et al. | |
| 6,656,198 B2 | 12/2003 | Tsonton et al. | |
| 6,673,248 B2 | 1/2004 | Chowdhury | |
| 6,679,882 B1 | 1/2004 | Kornerup | |
| 6,722,552 B2 | 4/2004 | Fenton, Jr. | |
| 6,770,072 B1 | 8/2004 | Truckai et al. | |
| 6,773,409 B2 | 8/2004 | Truckai et al. | |
| 6,789,939 B2 | 9/2004 | Schrödinger et al. | |
| 6,800,085 B2 | 10/2004 | Selmon et al. | |
| 6,802,843 B2 | 10/2004 | Truckai et al. | |
| 6,811,842 B1 | 11/2004 | Ehrnsperger et al. | |
| 6,821,273 B2 | 11/2004 | Mollenauer | |
| 6,860,880 B2 | 3/2005 | Treat et al. | |
| 6,905,497 B2 | 6/2005 | Truckai et al. | |
| 6,908,463 B2 | 6/2005 | Treat et al. | |
| 6,913,579 B2 | 7/2005 | Truckai et al. | |
| 6,926,716 B2 | 8/2005 | Baker et al. | |
| 6,929,622 B2 | 8/2005 | Chian | |
| 6,929,644 B2 | 8/2005 | Truckai et al. | |
| 6,953,461 B2 | 10/2005 | McClurken et al. | |
| 7,000,818 B2 | 2/2006 | Shelton, IV et al. | |
| 7,011,657 B2 | 3/2006 | Truckai et al. | |
| 7,041,102 B2 | 5/2006 | Truckai et al. | |
| 7,066,936 B2 | 6/2006 | Ryan | |
| 7,070,597 B2 | 7/2006 | Truckai et al. | |
| 7,083,619 B2 | 8/2006 | Truckai et al. | |
| 7,087,054 B2 | 8/2006 | Truckai et al. | |
| 7,101,372 B2 | 9/2006 | Dycus et al. | |
| 7,112,201 B2 | 9/2006 | Truckai et al. | |
| 7,125,409 B2 | 10/2006 | Truckai et al. | |
| 7,143,925 B2 | 12/2006 | Shelton, IV et al. | |
| 7,147,138 B2 * | 12/2006 | Shelton, IV | 227/176.1 |
| 7,156,846 B2 | 1/2007 | Dycus et al. | |
| 7,169,146 B2 | 1/2007 | Truckai et al. | |
| 7,169,156 B2 | 1/2007 | Hart | |
| 7,186,253 B2 | 3/2007 | Truckai et al. | |
| 7,189,233 B2 | 3/2007 | Truckai et al. | |
| 7,207,471 B2 | 4/2007 | Heinrich et al. | |
| 7,220,951 B2 | 5/2007 | Truckai et al. | |
| 7,225,964 B2 | 6/2007 | Mastri et al. | |
| 7,235,073 B2 | 6/2007 | Levine et al. | |
| 7,267,685 B2 | 9/2007 | Butaric et al. | |
| 7,307,313 B2 | 12/2007 | Ohyanagi et al. | |
| 7,309,849 B2 | 12/2007 | Truckai et al. | |
| 7,311,709 B2 | 12/2007 | Truckai et al. | |
| 7,329,257 B2 | 2/2008 | Kanehira et al. | |
| 7,354,440 B2 | 4/2008 | Truckal et al. | |
| 7,371,227 B2 | 5/2008 | Zeiner | |
| 7,381,209 B2 | 6/2008 | Truckai et al. | |
| 7,396,356 B2 * | 7/2008 | Mollenauer | 606/51 |
| 7,404,508 B2 | 7/2008 | Smith et al. | |
| 7,407,077 B2 | 8/2008 | Ortiz et al. | |
| 7,435,582 B2 | 10/2008 | Zimmermann et al. | |
| 7,445,621 B2 | 11/2008 | Dumbauld et al. | |
| 7,464,846 B2 | 12/2008 | Shelton, IV et al. | |
| 7,488,319 B2 | 2/2009 | Yates | |
| 7,510,107 B2 | 3/2009 | Timm et al. | |
| 7,513,025 B2 | 4/2009 | Fischer | |
| 7,517,349 B2 | 4/2009 | Truckai et al. | |
| 7,550,216 B2 | 6/2009 | Ofer et al. | |
| 7,559,452 B2 * | 7/2009 | Wales et al. | 227/176.1 |
| 7,588,176 B2 | 9/2009 | Timm et al. | |
| 7,597,693 B2 | 10/2009 | Garrison | |
| 7,604,150 B2 | 10/2009 | Boudreaux | |
| 7,628,792 B2 | 12/2009 | Guerra | |
| 7,641,671 B2 | 1/2010 | Crainich | |
| 7,644,848 B2 * | 1/2010 | Swayze et al. | 227/2 |
| 7,658,311 B2 | 2/2010 | Boudreaux | |
| 7,665,647 B2 | 2/2010 | Shelton, IV et al. | |
| 7,666,206 B2 | 2/2010 | Taniguchi et al. | |
| 7,703,459 B2 * | 4/2010 | Saadat et al. | 128/898 |
| 7,708,751 B2 | 5/2010 | Hughes et al. | |
| 7,722,607 B2 | 5/2010 | Dumbauld et al. | |
| 7,753,904 B2 | 7/2010 | Shelton, IV et al. | |
| 7,762,445 B2 * | 7/2010 | Heinrich et al. | 227/180.1 |
| 7,766,910 B2 | 8/2010 | Hixson et al. | |
| 7,776,037 B2 | 8/2010 | Odom | |

| | | | |
|---|---|---|---|
| 7,780,663 B2 * | 8/2010 | Yates et al. ............... 606/51 | |
| 7,784,663 B2 | 8/2010 | Shelton, IV | |
| 7,815,641 B2 | 10/2010 | Dodde et al. | |
| 7,819,298 B2 | 10/2010 | Hall et al. | |
| 7,832,408 B2 | 11/2010 | Shelton, IV et al. | |
| 7,832,612 B2 | 11/2010 | Baxter, III et al. | |
| 7,879,035 B2 | 2/2011 | Garrison et al. | |
| 7,879,070 B2 | 2/2011 | Ortiz et al. | |
| 7,931,649 B2 | 4/2011 | Couture et al. | |
| 7,935,114 B2 | 5/2011 | Takashino et al. | |
| 7,955,331 B2 | 6/2011 | Truckai et al. | |
| 7,963,963 B2 | 6/2011 | Francischelli et al. | |
| 7,981,113 B2 | 7/2011 | Truckai et al. | |
| 8,070,036 B1 * | 12/2011 | Knodel ............... 227/178.1 | |
| 8,136,712 B2 | 3/2012 | Zingman | |
| 8,141,762 B2 | 3/2012 | Bedi et al. | |
| 8,157,145 B2 * | 4/2012 | Shelton et al. ......... 227/175.1 | |
| 8,246,618 B2 | 8/2012 | Bucciaglia et al. | |
| 8,298,232 B2 | 10/2012 | Unger | |
| 2002/0165541 A1 | 11/2002 | Whitman | |
| 2003/0105474 A1 | 6/2003 | Bonutti | |
| 2003/0114851 A1 | 6/2003 | Truckai et al. | |
| 2003/0130693 A1 | 7/2003 | Levin et al. | |
| 2003/0158548 A1 | 8/2003 | Phan et al. | |
| 2003/0216722 A1 | 11/2003 | Swanson | |
| 2004/0019350 A1 | 1/2004 | O'Brien et al. | |
| 2004/0138621 A1 | 7/2004 | Jahns et al. | |
| 2004/0193150 A1 | 9/2004 | Sharkey et al. | |
| 2004/0232196 A1 | 11/2004 | Shelton, IV et al. | |
| 2005/0085809 A1 | 4/2005 | Mucko et al. | |
| 2005/0165429 A1 | 7/2005 | Douglas et al. | |
| 2005/0203507 A1 | 9/2005 | Truckai et al. | |
| 2005/0261581 A1 | 11/2005 | Hughes et al. | |
| 2005/0267464 A1 | 12/2005 | Truckai et al. | |
| 2006/0052778 A1 | 3/2006 | Chapman et al. | |
| 2006/0064086 A1 | 3/2006 | Odom | |
| 2006/0069388 A1 | 3/2006 | Truckai et al. | |
| 2006/0159731 A1 | 7/2006 | Shoshan | |
| 2006/0217709 A1 | 9/2006 | Couture et al. | |
| 2007/0027469 A1 | 2/2007 | Smith et al. | |
| 2007/0073341 A1 | 3/2007 | Smith et al. | |
| 2007/0106158 A1 | 5/2007 | Madan et al. | |
| 2007/0146113 A1 | 6/2007 | Truckai et al. | |
| 2007/0191713 A1 | 8/2007 | Eichmann et al. | |
| 2007/0208312 A1 | 9/2007 | Norton et al. | |
| 2007/0232920 A1 | 10/2007 | Kowalski et al. | |
| 2007/0232926 A1 | 10/2007 | Stulen et al. | |
| 2007/0232927 A1 | 10/2007 | Madan et al. | |
| 2007/0232928 A1 | 10/2007 | Wiener et al. | |
| 2007/0239025 A1 | 10/2007 | Wiener et al. | |
| 2007/0260242 A1 | 11/2007 | Dycus et al. | |
| 2008/0071269 A1 | 3/2008 | Hilario et al. | |
| 2008/0147062 A1 | 6/2008 | Truckai et al. | |
| 2008/0167522 A1 | 7/2008 | Giordano et al. | |
| 2008/0188851 A1 | 8/2008 | Truckai et al. | |
| 2008/0221565 A1 | 9/2008 | Eder et al. | |
| 2008/0262491 A1 | 10/2008 | Swoyer et al. | |
| 2008/0294158 A1 | 11/2008 | Pappone et al. | |
| 2009/0048589 A1 | 2/2009 | Takashino et al. | |
| 2009/0076506 A1 | 3/2009 | Baker | |
| 2009/0076534 A1 | 3/2009 | Shelton, IV et al. | |
| 2009/0099582 A1 | 4/2009 | Isaacs et al. | |
| 2009/0125027 A1 | 5/2009 | Fischer | |
| 2009/0206140 A1 | 8/2009 | Scheib et al. | |
| 2009/0209979 A1 | 8/2009 | Yates et al. | |
| 2009/0248002 A1 | 10/2009 | Takashino et al. | |
| 2009/0320268 A1 | 12/2009 | Cunningham et al. | |
| 2010/0010299 A1 | 1/2010 | Bakos et al. | |
| 2010/0032470 A1 | 2/2010 | Hess et al. | |
| 2010/0036370 A1 | 2/2010 | Mirel et al. | |
| 2010/0036380 A1 | 2/2010 | Taylor et al. | |
| 2010/0036405 A1 | 2/2010 | Giordano et al. | |
| 2010/0081863 A1 | 4/2010 | Hess et al. | |
| 2010/0081864 A1 | 4/2010 | Hess et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0094323 A1 | 4/2010 | Isaacs et al. | |
| 2010/0237132 A1 | 9/2010 | Measamer et al. | |
| 2010/0264194 A1 | 10/2010 | Huang et al. | |
| 2011/0087208 A1 | 4/2011 | Boudreaux et al. | |
| 2011/0087209 A1 | 4/2011 | Boudreaux et al. | |
| 2011/0087218 A1 | 4/2011 | Boudreaux et al. | |
| 2011/0087219 A1 | 4/2011 | Boudreaux et al. | |
| 2011/0087220 A1 | 4/2011 | Felder et al. | |
| 2011/0155781 A1 | 6/2011 | Swensgard et al. | |
| 2011/0238065 A1 | 9/2011 | Hunt et al. | |
| 2011/0251608 A1 | 10/2011 | Timm et al. | |
| 2011/0251609 A1 | 10/2011 | Johnson et al. | |
| 2011/0251612 A1 | 10/2011 | Faller et al. | |
| 2011/0251613 A1 | 10/2011 | Guerra et al. | |
| 2011/0264093 A1 | 10/2011 | Schall | |
| 2011/0276057 A1 | 11/2011 | Conlon et al. | |
| 2011/0282339 A1 | 11/2011 | Weizman et al. | |
| 2011/0306963 A1 | 12/2011 | Dietz et al. | |
| 2011/0306964 A1 | 12/2011 | Stulen et al. | |
| 2011/0306965 A1 | 12/2011 | Norvell et al. | |
| 2011/0306966 A1 | 12/2011 | Dietz et al. | |
| 2011/0306967 A1 | 12/2011 | Payne et al. | |
| 2011/0306968 A1 | 12/2011 | Beckman et al. | |
| 2011/0306972 A1 | 12/2011 | Widenhouse et al. | |
| 2011/0306973 A1 | 12/2011 | Cummings et al. | |
| 2012/0010615 A1 | 1/2012 | Cummings et al. | |
| 2012/0010616 A1 | 1/2012 | Huang et al. | |
| 2012/0012636 A1 | 1/2012 | Beckman et al. | |
| 2012/0016413 A1 | 1/2012 | Timm et al. | |
| 2012/0022519 A1 | 1/2012 | Huang et al. | |
| 2012/0022524 A1 | 1/2012 | Timm et al. | |
| 2012/0022525 A1 | 1/2012 | Dietz et al. | |
| 2012/0022526 A1 | 1/2012 | Aldridge et al. | |
| 2012/0022527 A1 | 1/2012 | Woodruff et al. | |
| 2012/0022528 A1 | 1/2012 | White et al. | |
| 2012/0022529 A1 | 1/2012 | Shelton, IV et al. | |
| 2012/0022530 A1 | 1/2012 | Woodruff et al. | |
| 2012/0101488 A1 | 4/2012 | Aldridge et al. | |
| 2012/0150176 A1 | 6/2012 | Weizman | |

FOREIGN PATENT DOCUMENTS

| | | |
|---|---|---|
| EP | 0630612 A1 | 12/1994 |
| EP | 0705571 A1 | 4/1996 |
| EP | 0640317 B1 | 9/1999 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/045348 A2 | 4/2008 |
| WO | WO 2008/099529 A1 | 8/2008 |

| WO | WO 2008/101356 A1 | 8/2008 |
| WO | WO 2009/022614 A1 | 2/2009 |
| WO | WO 2009/036818 A1 | 3/2009 |
| WO | WO 2009/059741 A1 | 5/2009 |
| WO | WO 2009/082477 A2 | 7/2009 |
| WO | WO 2010/017266 A1 | 2/2010 |
| WO | WO 2010/104755 A1 | 9/2010 |
| WO | WO 2011/089717 A1 | 7/2011 |

OTHER PUBLICATIONS

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1..., accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomechanical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/635,415, filed Dec. 10, 2009.
U.S. Appl. No. 12/647,134, filed Dec. 24, 2009.
U.S. Appl. No. 12/622,113, filed Nov. 19, 2009.

Partial International Search Report for PCT/US2011/043844, Oct. 21, 2011 (2 pages).

International Search Report for PCT/US2011/043844, Jun. 1, 2012 (6 pages).

Wright, et al., "Time-Temperature Equivalence of Heat-Induced Changes in Cells and Proteins," Feb. 1998. ASME Journal of Biomechanical Engineering, vol. 120, pp. 22-26.

U.S. Appl. No. 13/221,410, filed Aug. 30, 2011.
U.S. Appl. No. 13/189,169, filed Jul. 22, 2011.

* cited by examiner

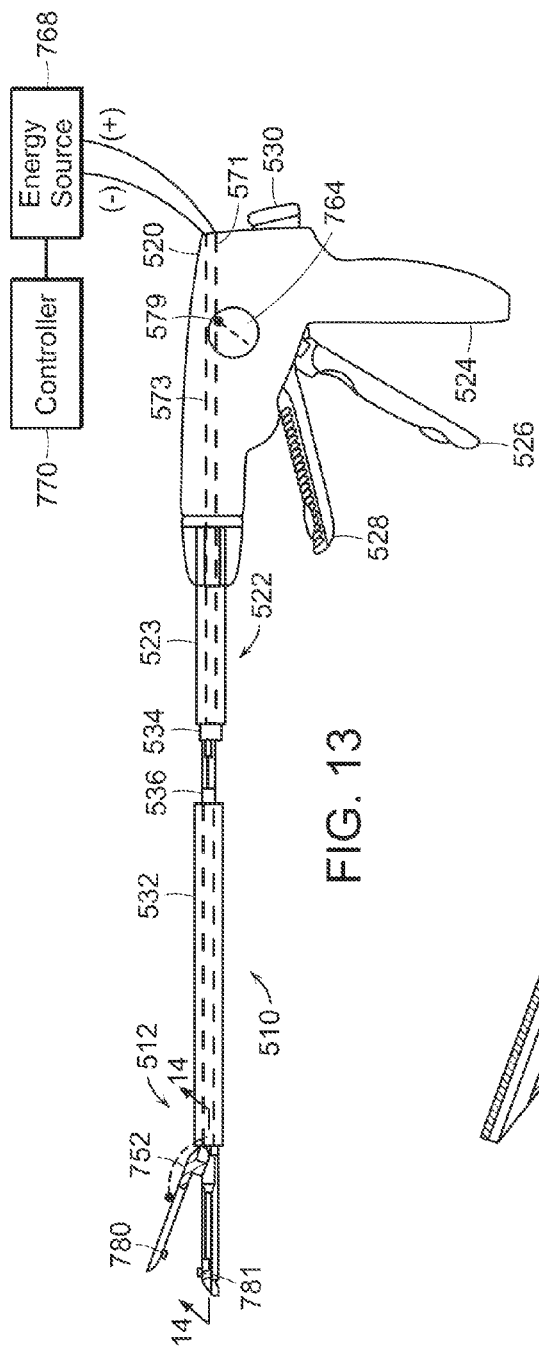
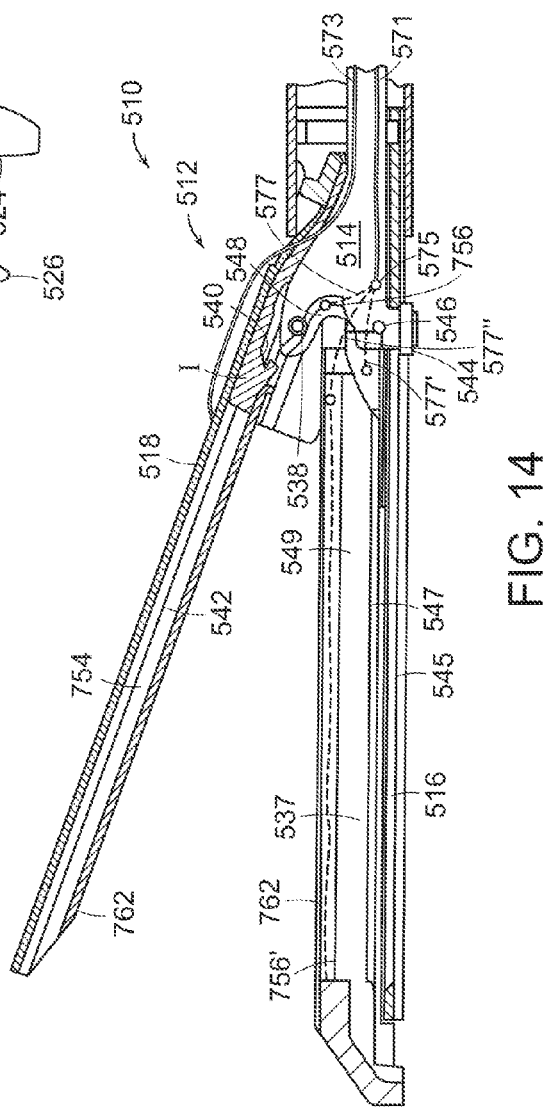
FIG. 13
FIG. 14

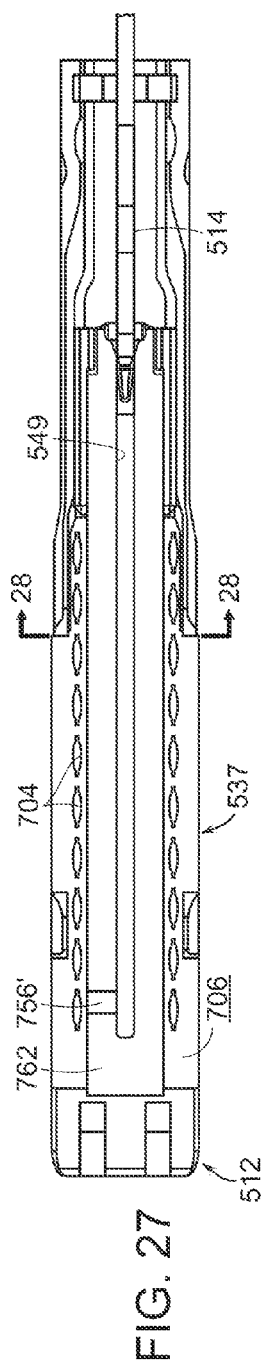
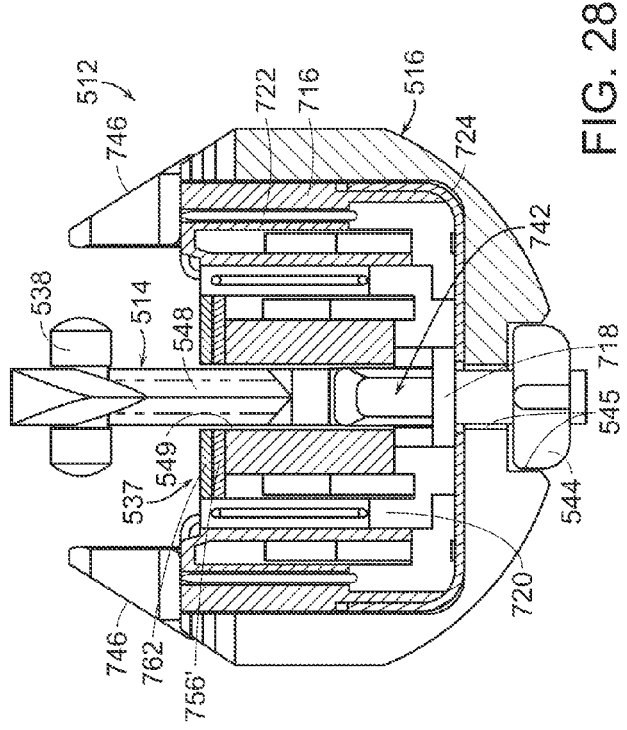
FIG. 27
FIG. 28

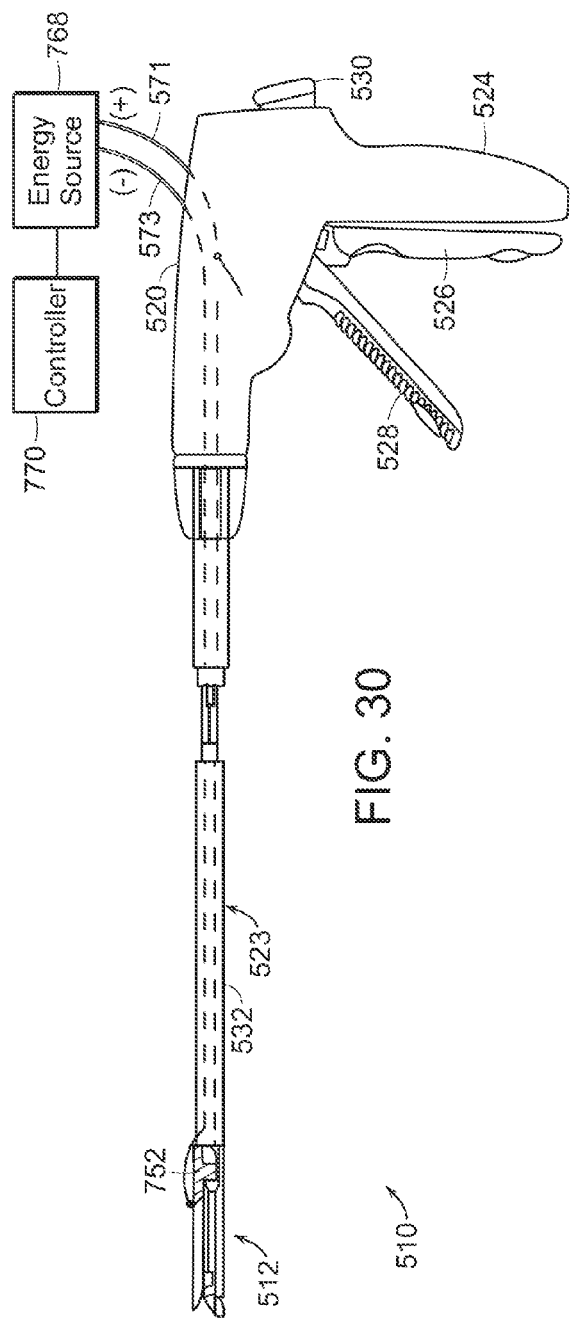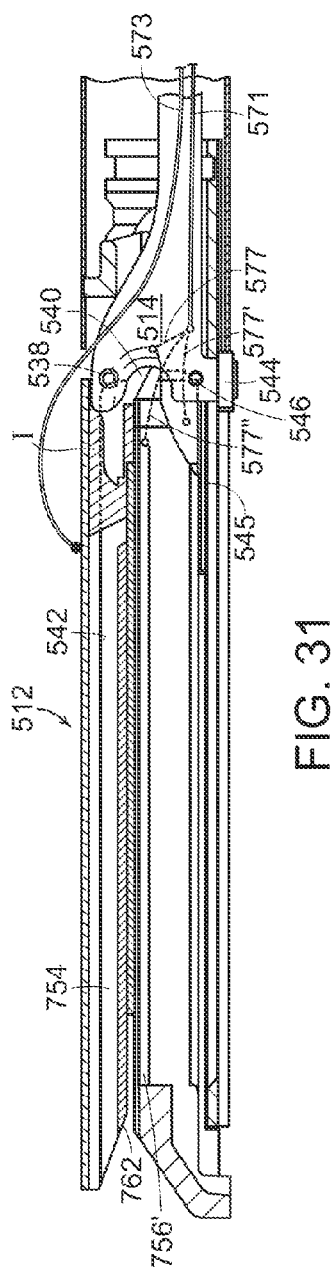

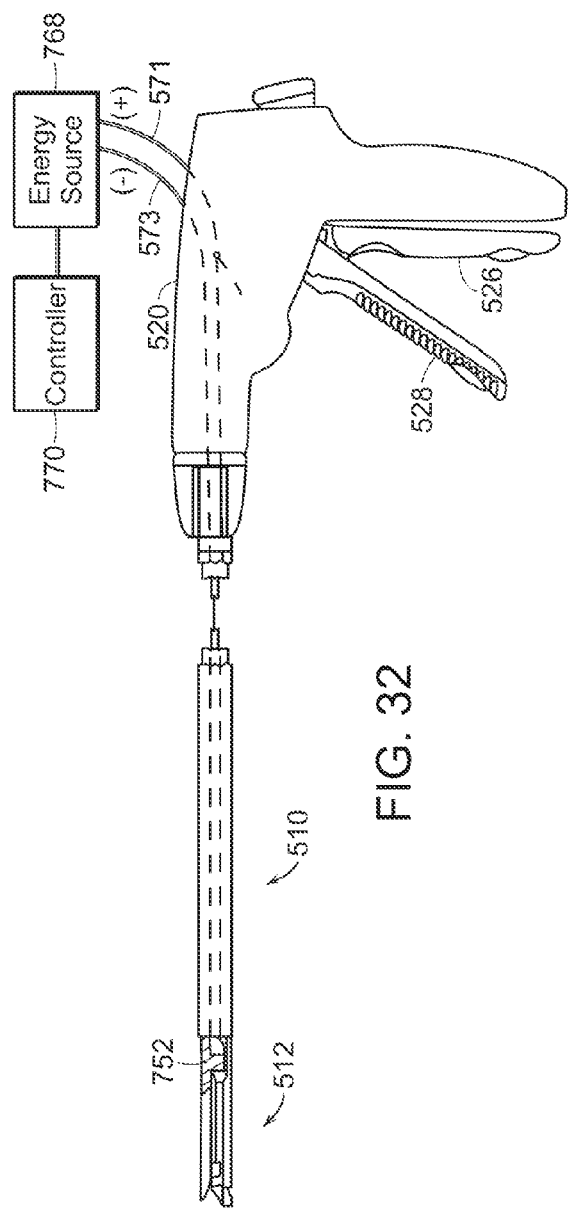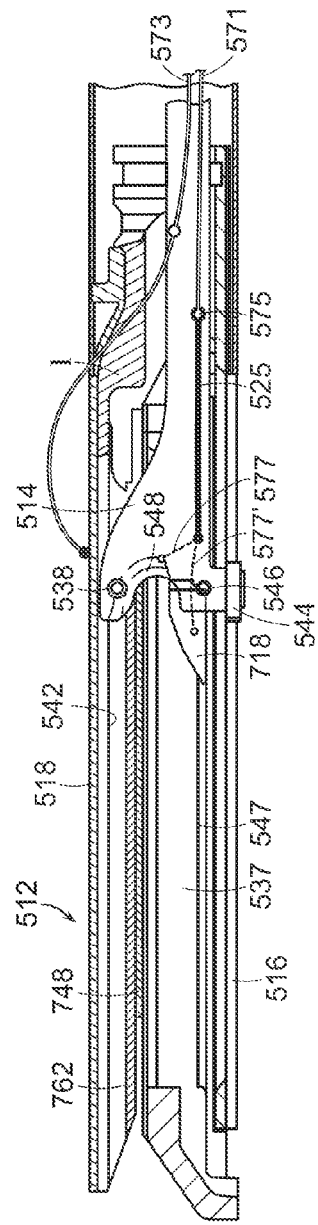

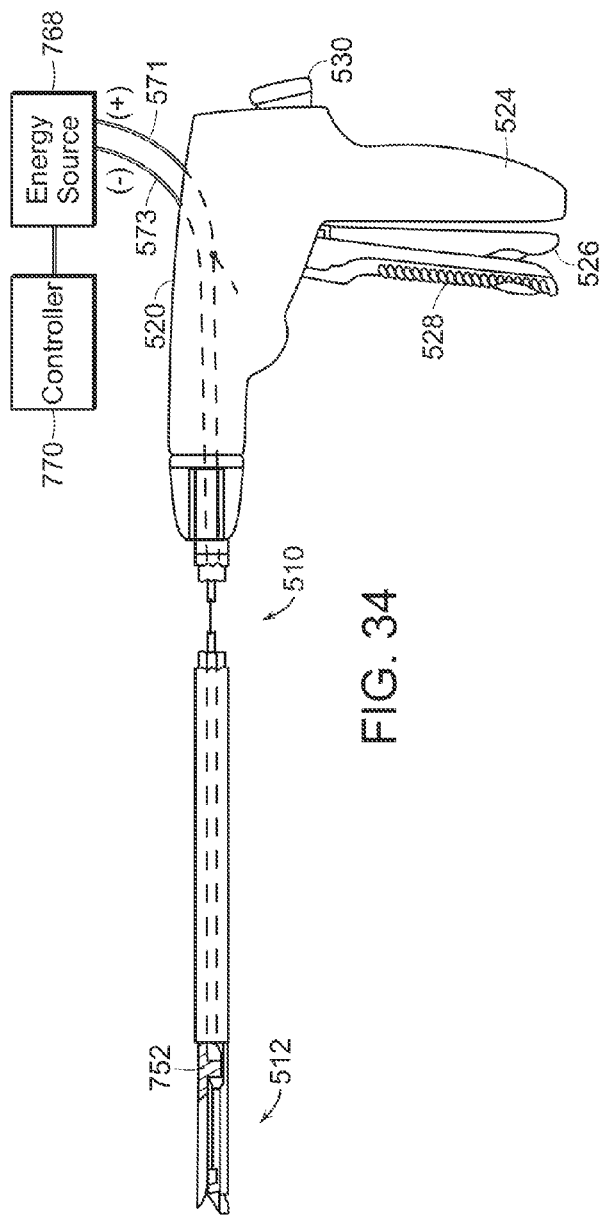
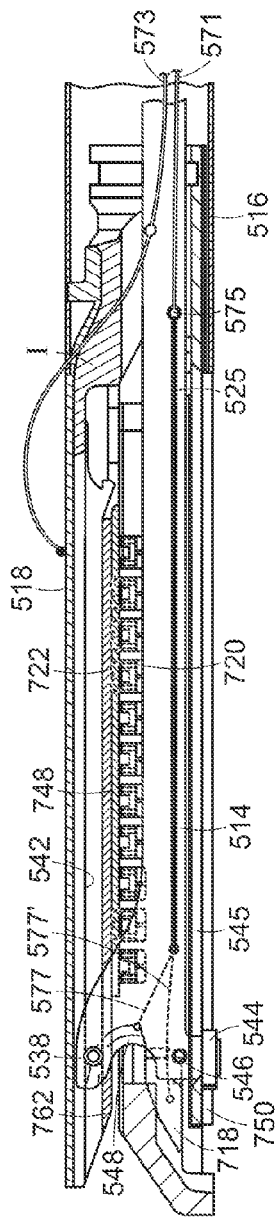
FIG. 34
FIG. 35

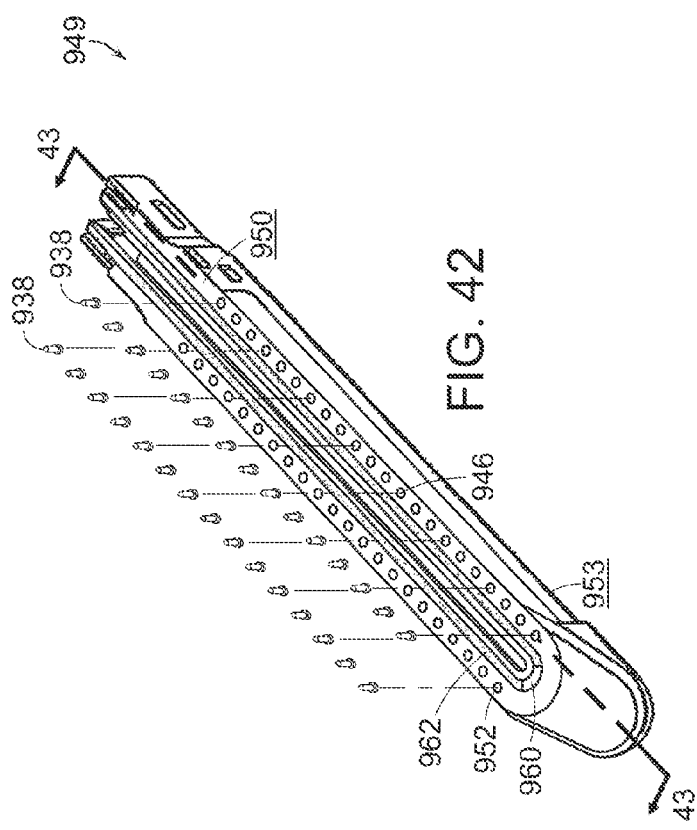
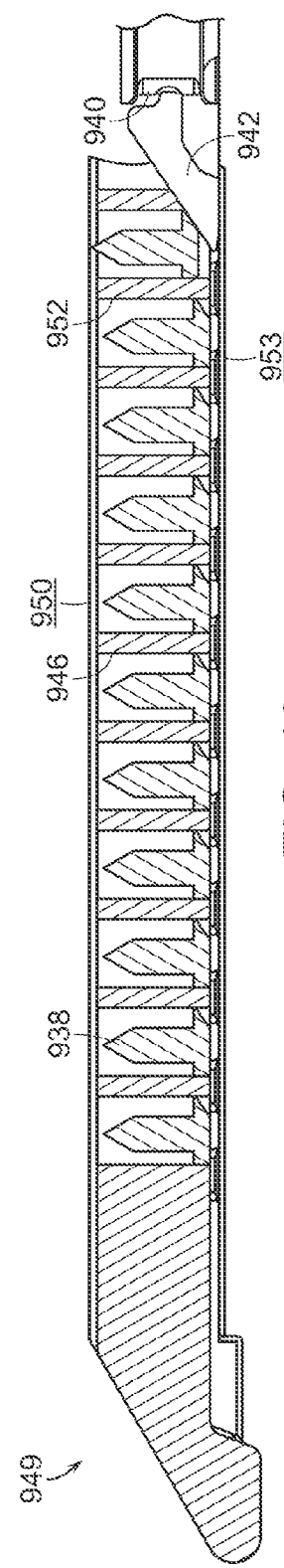
FIG. 42
FIG. 43

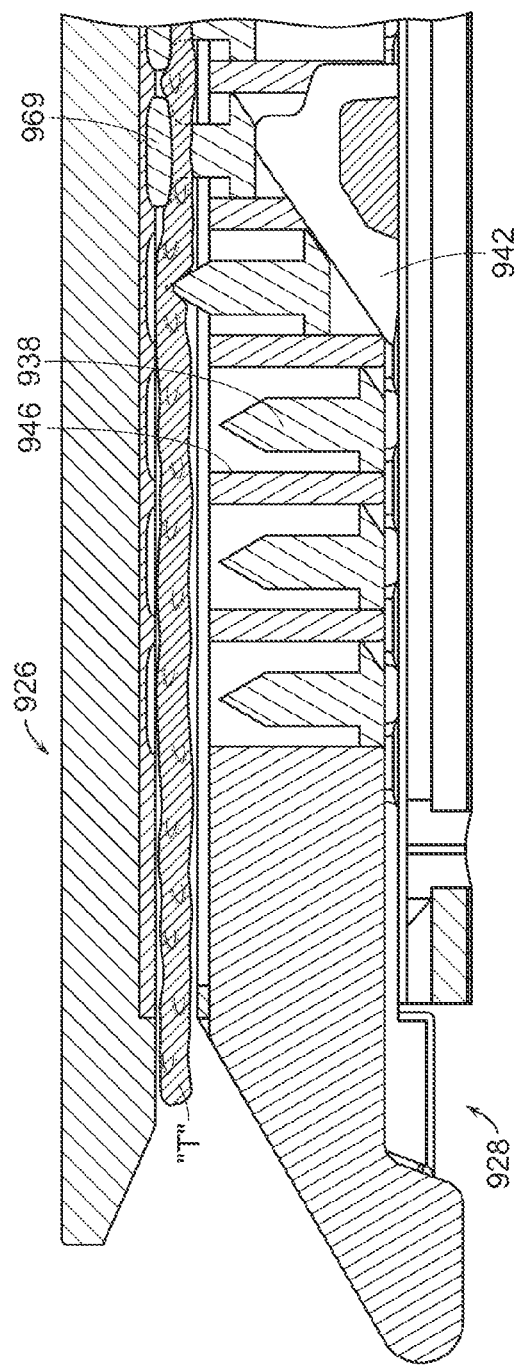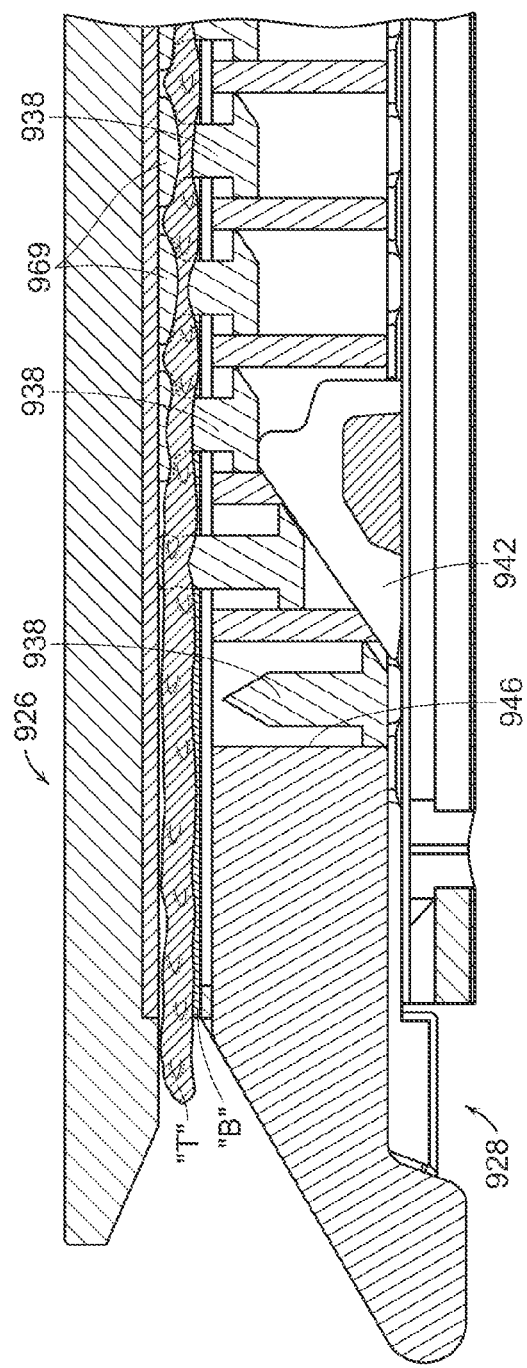

SURGICAL INSTRUMENTS WITH ELECTRODES

FIELD

The present disclosure is generally directed to surgical instruments and, more particularly, is directed to surgical instruments comprising electrodes.

BACKGROUND

In various open, endoscopic, and/or laparoscopic surgeries, for example, it may be desirable to coagulate, seal, and/or fuse tissue. One method of sealing tissue relies upon the application of energy, such as electrical energy, for example, to tissue captured or clamped within an end effector or an end-effector assembly of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue can elevate the temperature of the tissue and, as a result, the energy can at least partially denature proteins within the tissue. Such proteins, like collagen, for example, can be denatured into a proteinaceous amalgam that intermixes and fuses, or seals, together as the proteins renature. As the treated region heals over time, this biological seal may be reabsorbed by the body's wound healing process.

The foregoing discussion is intended only to illustrate various aspects of the related art and should not be taken as a disavowal of claim scope.

SUMMARY

In one non-limiting embodiment, the present disclosure, in part, is directed to an end-effector assembly configured to be attached to a surgical instrument. The end-effector assembly comprises a first jaw and a second jaw comprising a staple cavity. At least one of the first jaw and the second jaw is movable relative to the other jaw. The end-effector assembly comprises a staple removably positioned within the staple cavity and an electrically-conductive driver configured to move the staple between a first stored position in which the staple is at least partially positioned within the staple cavity and a second position in which the staple is at least partially deployed from the staple cavity into tissue positioned intermediate the first jaw and the second jaw. The staple comprises an electrode.

In one non-limiting embodiment, the present disclosure, in part, is directed to an end-effector assembly configured to be engaged with a surgical instrument. The end-effector assembly comprises a first jaw and a second jaw comprising a staple cavity. At least one of the first jaw and the second jaw is movable relative to the other jaw. The end-effector assembly comprises a staple removably positioned within the staple cavity and an electrically-conductive driver configured to deploy the staple at least partially from the staple cavity into tissue positioned intermediate the first jaw and the second jaw. The staple comprises a first electrode one of the first jaw and the second jaw comprises a second electrode.

In one non-limiting embodiment, the present disclosure, in part, is directed to an end-effector assembly configured to be engaged with a surgical instrument. The end-effector assembly comprises an electrode system comprising an electrode and a staple deploying system comprising a staple cavity, a staple removably positioned within the staple cavity, and a staple driver configured to move the staple between a first position in which the staple is stored at least partially within the staple cavity and a second position in which the staple is at least partially deployed from the staple cavity. The end-effector assembly comprises a staple sensor configured to sense when the staple is in the first position, a tissue thickness sensor configured to sense a thickness of tissue positioned within the end-effector assembly, and a lockout device configured to deactivate the electrode system when the sensed thickness is greater than a predetermined tissue thickness threshold and when the staple sensor does not sense the staple in the first position.

The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with the advantages thereof, may be understood in accordance with the following description taken in conjunction with the accompanying drawings as follows.

FIG. 13 is a partial cut-away side view of a surgical instrument configured to cut, staple, and/or seal tissue in accordance with one non-limiting embodiment of the present disclosure;

FIG. 14 is a cut-away side view of an end-effector assembly of the surgical instrument of FIG. 13 in accordance with one non-limiting embodiment of the present disclosure;

FIG. 27 is a sectional view of the end-effector assembly of FIG. 22 taken along line 27-27 in accordance with one non-limiting embodiment of the present disclosure;

FIG. 28 is a sectional view of the end-effector assembly of FIG. 27 taken along line 28-28 in accordance with one non-limiting embodiment of the present disclosure;

FIG. 30 is a partial cut-away side view of the surgical instrument of FIG. 13 with the end-effector assembly in a closed position in accordance with one non-limiting embodiment of the present disclosure;

FIG. 31 is a sectional view of the end-effector assembly of FIG. 30 taken along the longitudinal centerline of the end-effector assembly when tissue positioned within the end-effector is compressed in accordance with one non-limiting embodiment of the present disclosure;

FIG. 32 is a partial cut-away side view of the surgical instrument of FIG. 13 in a partially fired positioned in accordance with one non-limiting embodiment of the present disclosure;

FIG. 33 is a sectional view of the end-effector assembly of FIG. 32 taken along the longitudinal centerline of the end-effector assembly in a partially fired position in accordance with one non-limiting embodiment of the present disclosure;

FIG. 34 is a partial cut-away side view of the surgical instrument of FIG. 13 in a fully fired positioned in accordance with one non-limiting embodiment of the present disclosure;

FIG. 35 is a sectional view of the end-effector assembly of FIG. 34 taken along the longitudinal centerline of the end-effector assembly in a fully fired position in accordance with one non-limiting embodiment of the present disclosure;

FIG. 42 is a perspective view of a rivet cartridge configured for use with an end-effector in accordance with one non-limiting embodiment of the present disclosure;

FIG. 43 is a cross-sectional view of the rivet cartridge taken along line 43-43 of FIG. 42 in accordance with one non-limiting embodiment of the present disclosure;

FIGS. 45 and 46 are cross-sectional views of an end-effector of the surgical instrument of FIG. 39 with some rivets deployed into the tissue in accordance with one non-limiting embodiment of the present disclosure;

Figure 1:
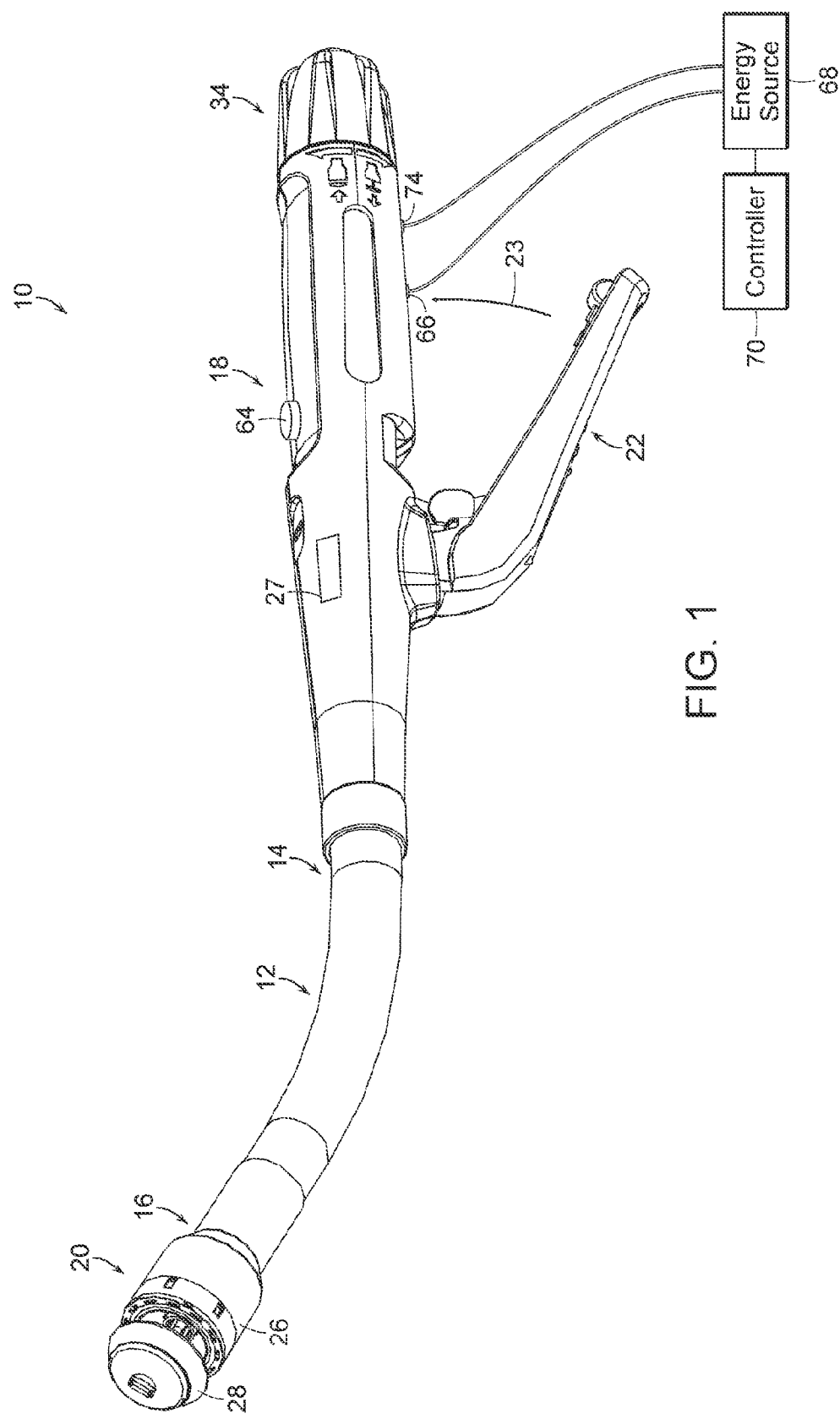
FIG. 1 is a perspective view a surgical instrument in accordance with one non-limiting embodiment of the present disclosure.
Figure 2:
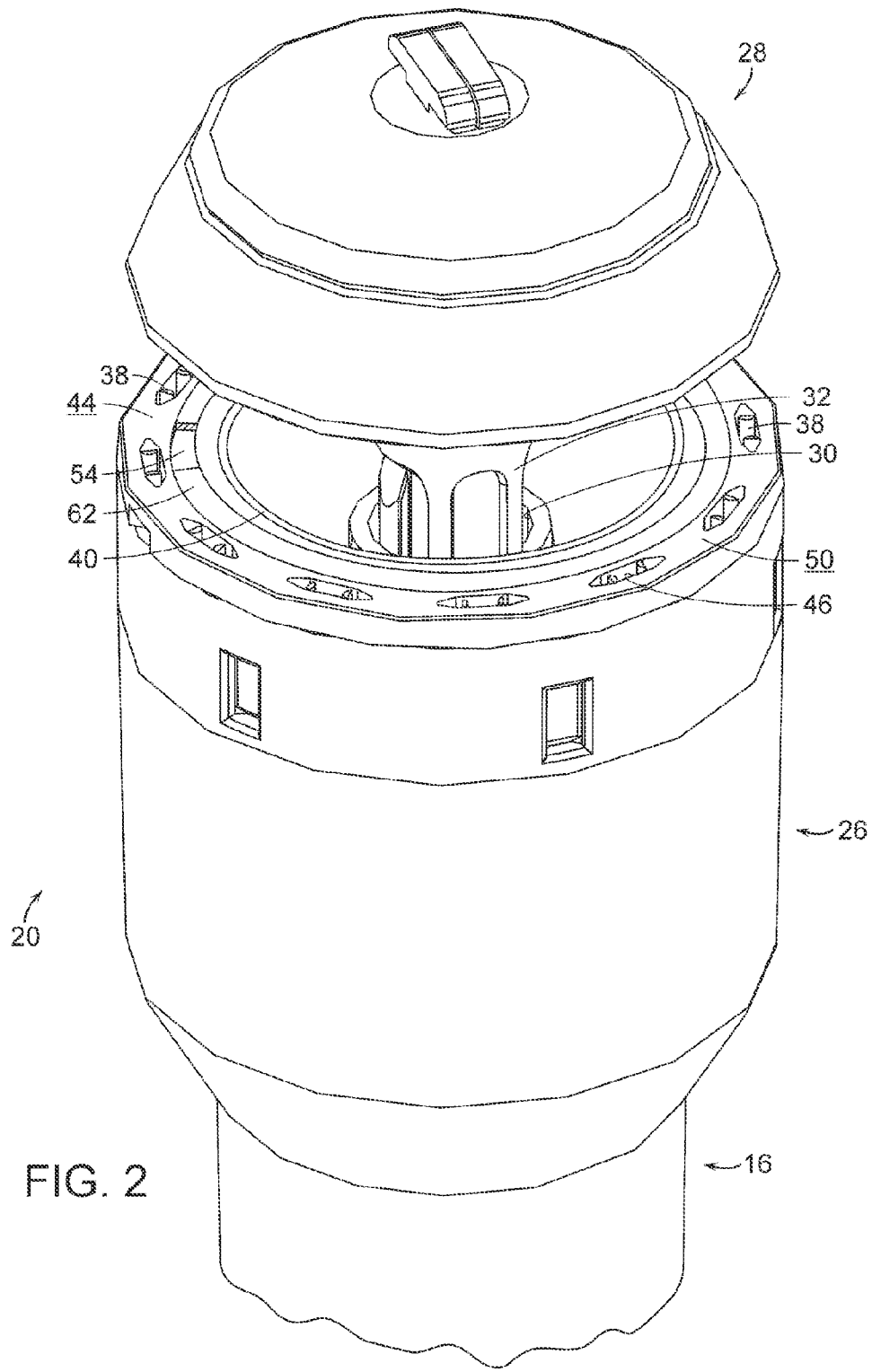
FIG. 2 is a perspective view of an end-effector of the surgical instrument of FIG. 1 in accordance with one non-limiting embodiment of the present disclosure.
Figure 3:
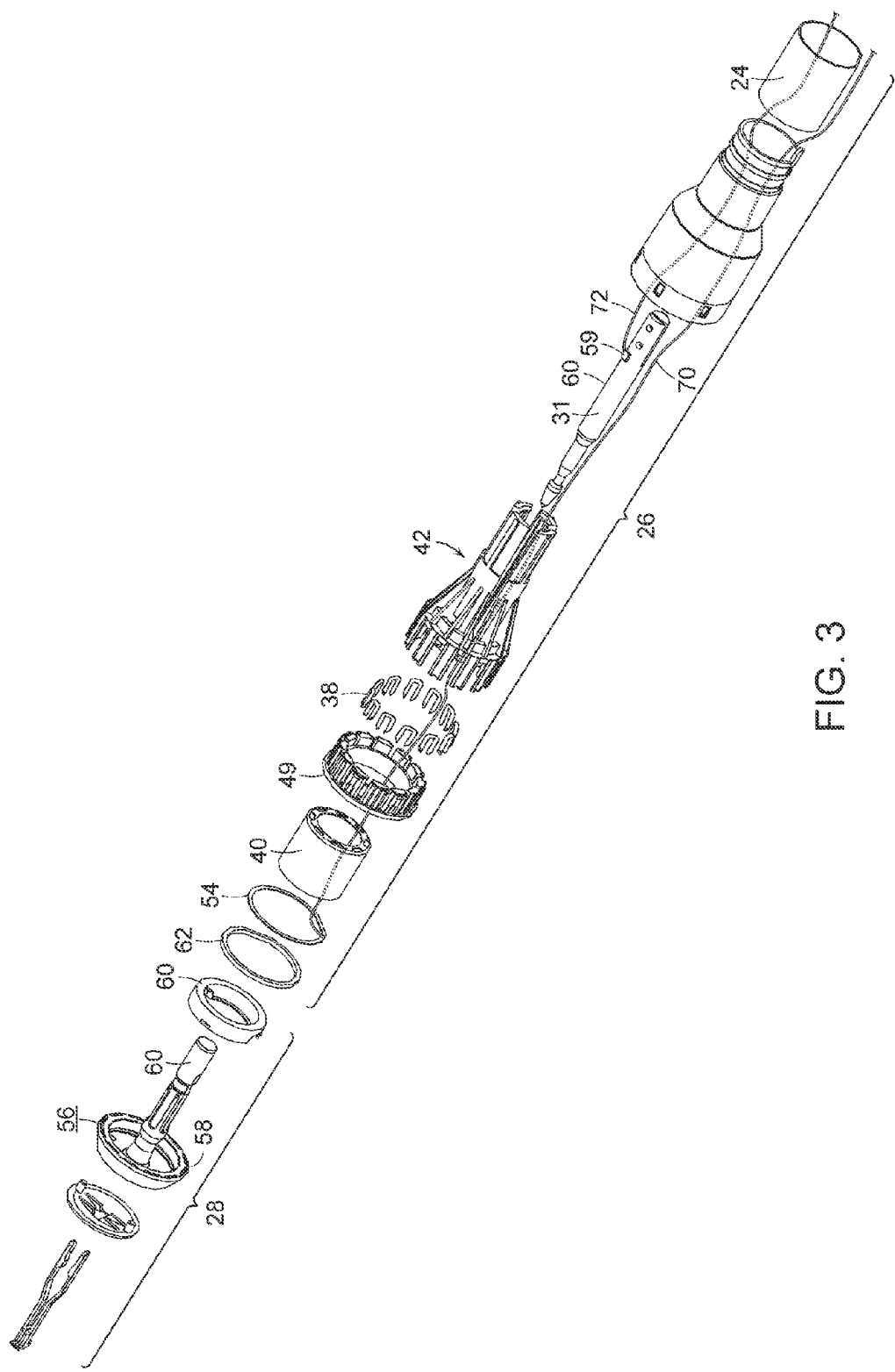
FIG. 3 is an exploded perspective view of the end-effector of FIG. 2 in accordance with one non-limiting embodiment of the present disclosure.

Corresponding reference characters indicate corresponding parts throughout the several views. The example embodiments set out herein illustrate various embodiments of the present disclosure, in one form, and such example embodiments are not to be construed as limiting the scope of the present disclosure in any manner.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," "certain embodiments," or "an embodiment", or the like, means that a particular feature, structure, or characteristic described in connection with the embodiment is included in at least one embodiment. Thus, appearances of the phrases "in various embodiments," "in some embodiments," "in one embodiment," "in certain embodiments," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209 to Truckai et al., entitled ELECTROSURGICAL INSTRUMENT, which issued on Jun. 3, 2008;

U.S. Pat. No. 7,354,440 to Truckai et al., entitled ELECTROSURGICAL INSTRUMENT AND METHOD OF USE, which issued on Apr. 8, 2008;

U.S. Pat. No. 7,311,709 to Truckai et al., entitled ELECTROSURGICAL INSTRUMENT AND METHOD OF USE, which issued on Dec. 25, 2007;

U.S. Pat. No. 7,309,849 to Truckai et al., entitled POLYMER COMPOSITIONS EXHIBITING A PTC PROPERTY AND METHODS OF FABRICATION, which issued on Dec. 18, 2007;

U.S. Pat. No. 7,220,951 to Truckai et al., entitled SURGICAL SEALING SURFACES AND METHODS OF USE, which issued on May 22, 2007;

U.S. Pat. No. 7,189,233 to Truckai et al., entitled ELECTROSURGICAL INSTRUMENT, which issued on Mar. 13, 2007;

U.S. Pat. No. 7,186,253 to Truckai et al., entitled ELECTROSURGICAL JAW STRUCTURE FOR CONTROLLED ENERGY DELIVERY, which issued on Mar. 6, 2007;

U.S. Pat. No. 7,169,146 to Truckai et al., entitled ELECTROSURGICAL PROBE AND METHOD OF USE, which issued on Jan. 30, 2007;

U.S. Pat. No. 7,125,409 to Truckai et al., entitled ELECTROSURGICAL WORKING END FOR CONTROLLED ENERGY DELIVERY, which issued on Oct. 24, 2006; and U.S. Pat. No. 7,112,201 to Truckai et al., entitled ELECTROSURGICAL INSTRUMENT AND METHOD OF USE, which issued on Sep. 26, 2006.

Various embodiments of apparatuses, systems, and methods of the present disclosure relate to creating thermal "welds," "seals," and/or "fusion" within native tissue volumes. These terms may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The sealing, welding, or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "sealing" as the term is used herein. Such surface coagulation may not create a seal that provides any substantial strength in the treated tissue.

At the molecular level, the phenomena of truly "sealing" tissue as disclosed herein may result from the thermally-induced denaturation of collagen and other protein molecules in a targeted tissue volume to create a transient liquid or gel-like proteinaceous amalgam. A selected energy density can be provided in the targeted tissue to cause hydrothermal breakdown of intra- and intermolecular hydrogen crosslinks in collagen and other proteins. The denatured amalgam can be maintained at a selected level of hydration—without desiccation—for a selected time interval which can be very brief. The targeted tissue volume can be maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments disclosed herein provide electrosurgical jaw structures or portions adapted for transecting captured tissue between the jaws or portions and for contemporaneously sealing the captured tissue margins with controlled application of RF energy or other energy. The jaw structures can comprise a scoring or cutting element which can cut or score tissue independently of the tissue capturing and sealing functions of the jaw structures or portions. The jaw structures or portions can comprise first and second opposing jaws that carry fuses, such as positive temperature coefficient materials, for example, for modulating RF energy or other energy delivery to the engaged tissue.

The embodiments of the devices described herein may be introduced inside a patient using minimally invasive or open surgical techniques. In some instances, it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. In some circumstances, the devices can then access various tissue treatment regions translumenally. In other instances, the devices may not access the various tissue treatment regions translumenally. In any event, such procedures can be combined with laparoscopic, percutaneous, and/or open approaches. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions. Laparoscopic approaches can comprise Single Site Laparoscopy (SSL), which can involve a single trocar usually placed in the umbilicus containing multiple ports. SSL can also include the placement of multiple trocars in a single location to minimize scarring. In one embodiment, these SSL approaches may be combined with most NOTES™ procedures, natural orifice procedures, and/or percutaneous procedures, for example. SSL can also be referred to as Single Incision Laparocopic Surgery (SILS™) and Single Port Access (SPA). Robotic surgical approaches can also be used with the embodiments of the present disclosure.

Endoscopic minimally invasive surgical and diagnostic medical procedures can be used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Certain example embodiments will now be described to provide an overall understanding of the principles of the structure, function, manufacture, and use of the devices and methods disclosed herein. One or more examples of these embodiments are illustrated in the accompanying drawings.

Those of ordinary skill in the art will understand that the devices and methods specifically described herein and illustrated in the accompanying drawings are non-limiting example embodiments and that the scope of the various embodiments of the present disclosure is defined solely by the claims. The features illustrated or described in connection with one example embodiment may be combined with the features of other embodiments. Such modifications and variations are intended to be included within the scope of the present disclosure.

In various embodiments, surgical instruments, such as circular staplers, for example, have been developed for use in a surgical procedure known as an anastomosis. Circular staplers useful for performing an anastomosis are disclosed, for example, in U.S. Pat. No. 5,104,025 to Main et al. entitled INTRALUMINAL ANASTOMOTIC SURGICAL STAPLER WITH DETACHED ANVIL, which was issued on Apr. 14, 1992, U.S. Pat. No. 5,205,459 to Brinkerhoff et al., entitled SURGICAL ANASTOMOSIS STAPLING INSTRUMENT, which was issued on Apr. 27, 1993, U.S. Pat. No. 5,285,945 to Brinkerhoff et al., entitled SURGICAL ANASTOMOSIS STAPLING INSTRUMENT, which was issued on Feb. 15, 1994, and U.S. Pat. No. 5,309,927 to Welch, entitled CIRCULAR STAPLER TISSUE RETENTION SPRING METHOD, which was issued on May 10, 1994, and in U.S. patent application Ser. No. 12/408,905 to Measamer et al., entitled CIRCULAR SURGICAL STAPLING INSTRUMENT WITH ANVIL LOCKING SYSTEM, filed on Mar. 23, 2009, which are each herein incorporated by reference in their respective entireties.

One form of an anastomosis comprises a surgical procedure where two tubular sections of intestine are joined together after a diseased portion of the intestine has been excised. The procedure usually requires re-joining ends of the two tubular sections together to form a continuous tubular pathway. Previously, this surgical procedure was a laborious and time consuming operation. In most instances, the surgeon had to precisely cut and align the ends of the two tubular sections of intestine and maintain the alignment while joining the ends with numerous suture stitches. The development of surgical instruments, such as circular staplers, for example, has greatly simplified the anastomosis procedure and has also decreased the time required to perform an anastomosis.

In one embodiment, referring to FIGS. 1-5, a surgical instrument 10, such a surgical stapler, a circular tissue joining device, a circular surgical stapler, and/or a surgical stapling assembly, for example, can comprise an elongate shaft 12 comprising a proximal end 14 and a distal end 16. In various embodiments, the elongate shaft 12 can be rigid, while, in other embodiments, the elongate shaft 12 can be semi-rigid or flexible or can comprise semi-rigid or flexible portions. In one embodiment, at least a portion of the surgical instrument 10 can be configured to be partially inserted through a natural orifice in a patient, such as the anus, mouth, and/or vagina, or through an incision in a body wall using a trocar, for example. A handle portion 18 can extend from the proximal end 14 of the elongate shaft 12 and an end-effector 20 can extend from the distal end 16 of the elongate shaft 12. The terms "proximal" and "distal" are used herein with reference to the clinician or surgeon (hereafter "surgeon") holding the handle portion 18 of the surgical instrument 10. For example, the end-effector 20 is located distal from the surgeon while the handle portion 18 is located proximal to the surgeon. In various embodiments, the handle portion 18 can comprise two portions which are assembled together to form the handle portion 18, for example. In one embodiment, the two portions of the handle portion 18 can be snap-fit, press-fit, adhered, glued, and/or fastened to one another, for example.

In one embodiment, the handle portion 18 can comprise a trigger 22 operably engaged with an actuation mechanism 24. The actuation mechanism 24 can extend from the handle portion 18 to or proximate to a portion of the end-effector 20. In various embodiments, the actuation mechanism 24, or portions thereof, can be rigid, semi-rigid, or flexible. In an embodiment, where the actuation mechanism 24 is flexible, or comprises flexible portions, the material can still be rigid enough to drive a staple driver 42 and/or a cutting member 40 distally within the end-effector 20. The trigger 22 can be moved toward the handle portion 18 in the direction indicated generally by arrow 23 to cause the actuation mechanism 24 to move distally and fire or drive staples positioned within a portion of the end-effector 20 distally into tissue compressed within the end-effector 20, as described in further detail below. When the trigger 22 is moved toward the handle portion 18, thereby moving the actuation mechanism 24 distally, the cutting member 40 can also be moved distally to incise tissue compressed within the end-effector 20, as described in further detail below. In one embodiment, the actuation mechanism 24 or portions of the end-effector 20 can be steerable, for example.

In one embodiment, referring again to FIGS. 1-5, the end-effector 20 can comprise a first portion 26 and a second portion 28. The first portion 26 can comprise an aperture 30 extending therethrough such that a portion of an actuation member 31 can extend into the aperture 30 (see e.g., FIG. 5). A portion of the actuation member 31 can extend through the actuation mechanism 24. The second portion 28 of the end-effector 20 can comprise a projection 32 configured to extend at least partially into the aperture 30 and be operably engaged with the actuation member 31 via any suitable connection, such as an interlocking connection as illustrated in FIG. 5, for example. In one embodiment, a portion of the projection 32 can slide over a distal portion of the actuation member 31 and engage sidewalls or detents in the sidewalls of the actuation member 31 to operably join the portion of the projection 32 and the actuation member 31. In other various embodiments, a distal portion of an actuation member can slide over a portion of the projection and engage sidewalls or detents in the sidewalls of the projection to operably join the portion of the projection and the actuation member 31.

In one embodiment, when the projection 32 of the second portion 28 is operably engaged with the actuation member 31, the second portion 28 can be moved relative (e.g., distal/proximal movement) to the first portion 26 using an adjustment knob 34 located on a proximal portion of the handle portion 18, for example. The adjustment knob 34 can be operably engaged with the actuation member 31 such that as the adjustment knob 34 is moved or rotated, the actuation member 31 can move distally and/or proximally within the surgical instrument 10 (i.e., rotational motion of the adjustment knob 34 is converted into linear motion of the actuation member 31). In one embodiment, referring to FIG. 5, by turning the adjustment knob 34, the length of the adjustment member 31 extending into the aperture 30 in the first portion 26 can be adjusted. Stated another way, rotation of the adjustment knob 34 about its longitudinal axis can move the second portion 28 relative to the first portion 26 owing to the engagement of the portion of the projection 32 of the second portion 28 with the distal portion of the actuation member 31. For example, if the adjustment knob 34 is rotated in the clockwise direction, the length of the actuation member 31 within the aperture 30 can be increased, while if the adjustment knob 34 is rotated in the counter-clockwise direction, the length of the actuation member 31 within the aperture 30 can be decreased. Such adjustment of the length of the actuation member 31 within the aperture 30 in turn can adjust the distance that the second portion 28 is positioned from the first portion 26 thereby allowing the end-effector 20 to clamp and release tissue positioned intermediate the first portion 26 and the second portion 28.

Figure 4:
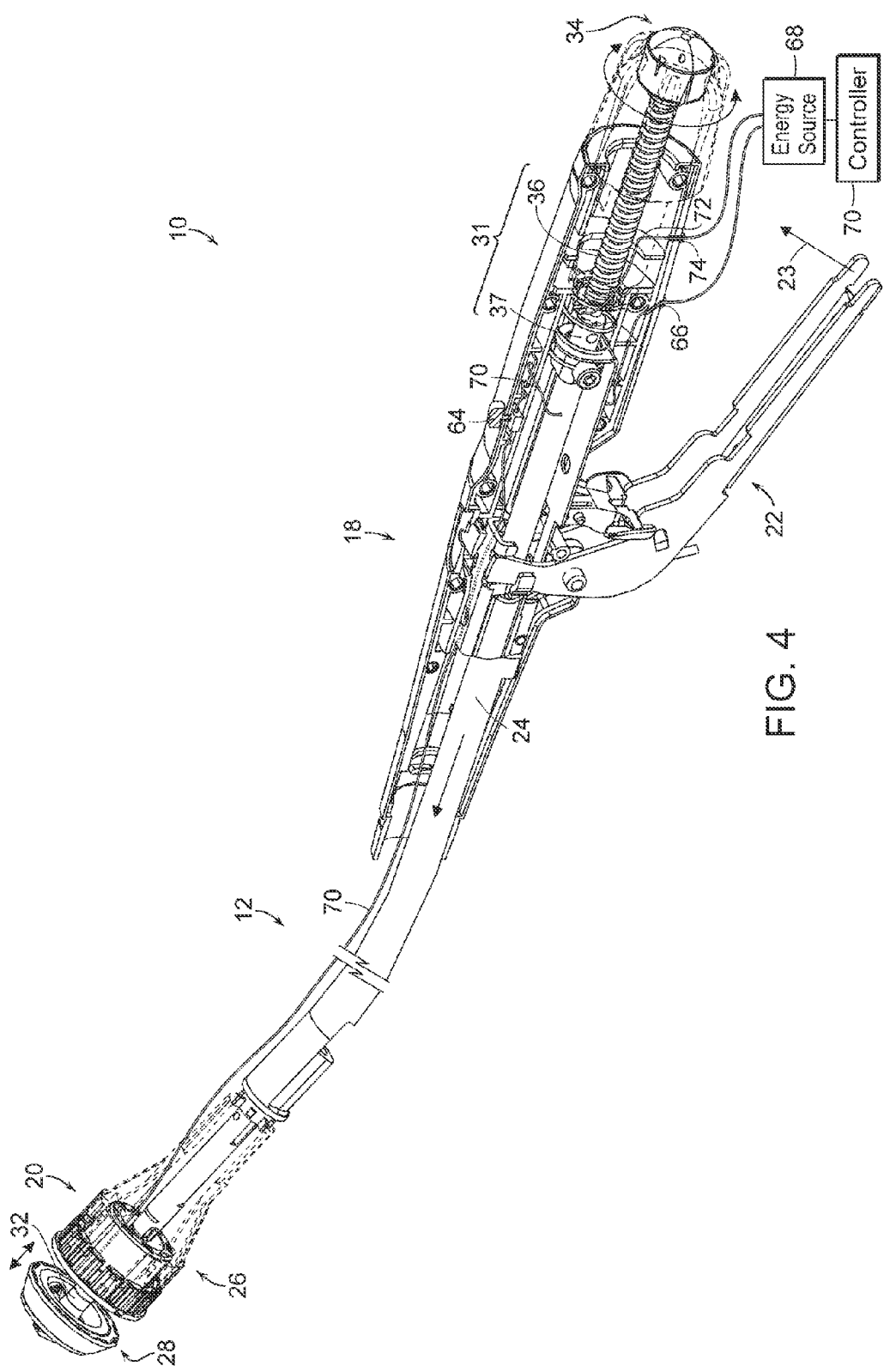
FIG. 4 is a cut-away perspective view of the surgical instrument of FIG. 1 in accordance with one non-limiting embodiment of the present disclosure.
Figure 5:
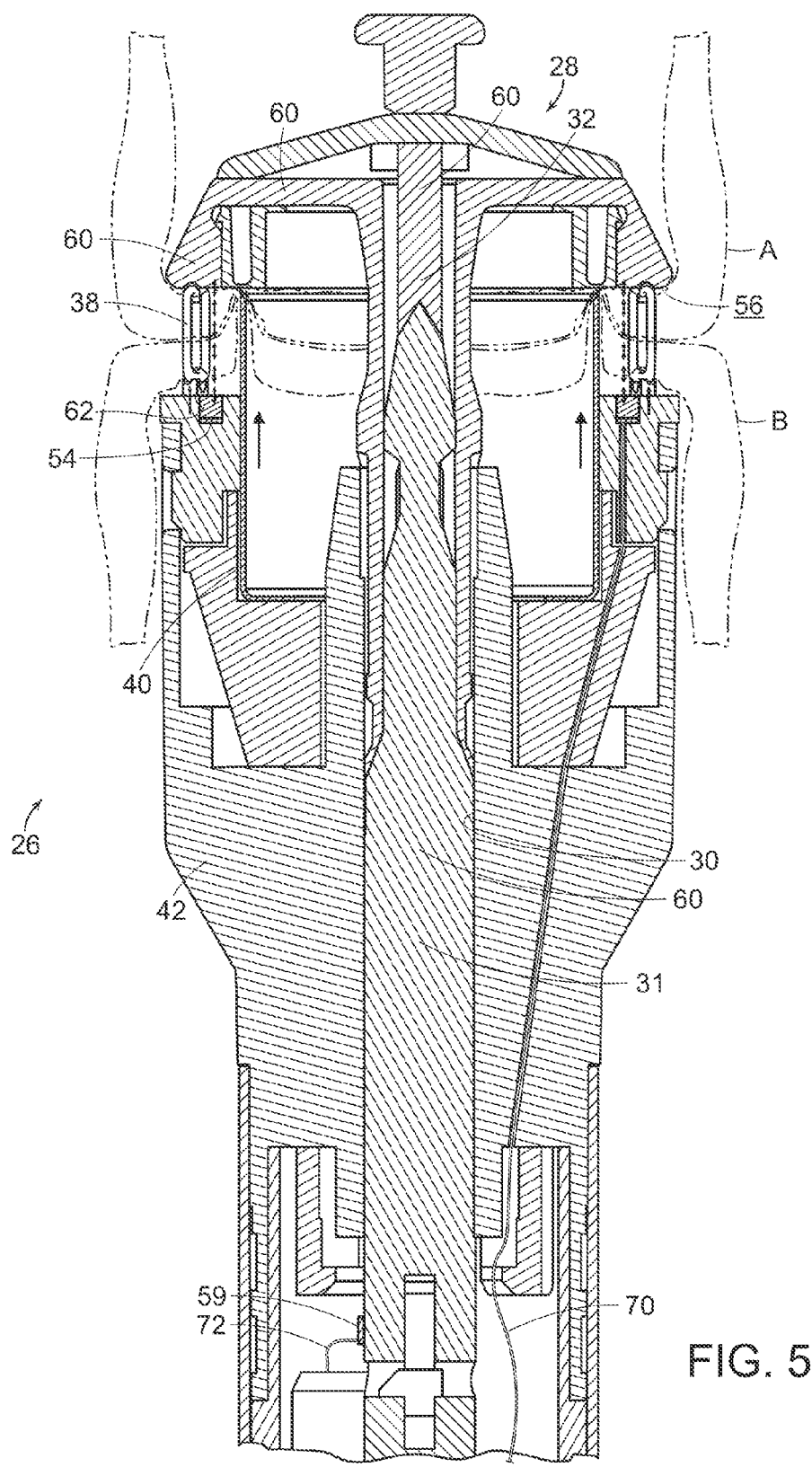
FIG. 5 is a cross-sectional view of an end-effector having tissue compressed between a first portion and a second portion thereof in accordance with one non-limiting embodiment of the present disclosure.

In one embodiment, referring to FIG. 4, the actuation member 31 can comprise a threaded rod 36 and an adjustment tube 37. A proximal end of the threaded rod 37 can be engaged with the actuation knob 34, such that rotation of the actuation knob 34 rotates the threaded rod 37. A distal end of the threaded rod 36 can be operably engaged with the adjustment tube 37. The adjustment tube 37 can comprise threads on its inner surface, for example, such that the threaded rod 36 can be threadably engaged with the adjustment tube 37 to move the adjustment tube 37 distally and proximally when the threaded rod 36 is rotated. Stated another way, the proximal end of the adjustment tube 37 can essentially ride on the distal end or portion of threaded rod 36 in threadable engagement. In one embodiment, the adjustment tube 37 can be configured and situated such that it does not rotate when the threaded rod 36 is rotated to allow distal/proximal movement of the adjustment tube 37.

In one embodiment, the adjustment knob 34 can be fixedly attached to the proximal end of the threaded rod 36 such that as the adjustment knob 34 is rotated in the clockwise direction, for example, the threaded rod 36 can also be rotated in the clockwise direction. Likewise, as the adjustment knob 34 is rotated in the counter-clockwise direction, the threaded rod 36 can also be rotated in the counter-clockwise direction. In one embodiment, when the adjustment knob 34 is rotated in the clockwise direction, the adjustment tube 37 can be moved distally and when the adjustment knob 34 is rotated in the counter-clockwise direction the adjustment tube 37 can be moved proximally. Such movement can adjust the distance between the first portion 26 and the second portion 28 when the portion of the projection 32 is engaged with the distal end or portion of the adjustment tube 37. In various embodiments, the adjustment tube 37 can comprise a flexible, a semi-rigid, and/or a rigid material, for example. In one embodiment, although not illustrated, an adjustment tube may extend fully through the aperture 30 in the first portion 26 such that it can be engaged with the second portion 28. In such an embodiment, the second portion 28 of the end-effector 20 may not comprise a projection.

In one embodiment, the adjustment knob 34 and the actuation member 31 can be configured to move the second portion 28 to at least one predetermined distance from the first portion 26 to cause tissue positioned between the first portion 26 and the second portion 28 to be compressed or clamped. In various embodiments, the adjustment knob 34, during rotation, can encounter a stop (not illustrated) when the predetermined distance or a minimum distance between the second portion 28 and the first portion 26 is reached so as to not allow a surgeon to over compress tissue positioned intermediate the first portion 26 and the second portion 28. In one embodiment, a tissue compression indicator 27 can be provided on the surgical instrument 10. The tissue compression indicator 27 can be operably or electronically linked to the adjustment knob 34, the actuation member 31, or the end-effector 20 such that the tissue compression indicator 27 can provide the surgeon with visual, audible, or tactile feedback of the tissue compression or the distance between the first portion 26 or the second portion 28. In one embodiment, the tissue compression indicator 27 can indicate to a surgeon the degree to which staple legs will be deformed, for example, based on the distance between the first portion 26 and the second portion 28. Various embodiments of such tissue compression indicators are known to those of skill in the art. In one embodiment, the projected tissue compression and projected staple leg deformation can be measured by measuring the impedance of the tissue across the thickness of the tissue, for example.

In one embodiment, referring to FIGS. 1 and 4, the trigger 22 extending from the handle portion 18, when moved in the direction indicated generally by arrow 23, can cause the actuation mechanism 24 to move distally within the elongate shaft 12 to drive the staple driver member 42 distally and deploy staples 38 distally into tissue compressed intermediate the first portion 26 and the second portion 28 and/or drive the cutting member 40 distally to incise the tissue. In one embodiment, the actuation mechanism 24, the staples 38, the staple driver member 42, and/or the cutting member 40 can each comprise an electrically conductive portion or can be comprised of an electrically conductive material, such that energy can be transmitted to the staples 38 and/or the cutting member 40, as discussed in further detail herein. In one embodiment, a staple driver member and a cutting member can be formed of the same component. In various embodiments, the trigger 22 can be pivotably attached to the handle portion 18 such that as the proximal end of the trigger 22 is moved toward the handle portion 18, the distal end of the trigger 22 forces the actuation mechanism 24 distally within the elongate shaft 12 owing to an attachment between the distal portion of the trigger 22 and a proximal portion of actuation mechanism 24.

In one embodiment, the trigger 22 can be normally-biased away from the handle portion 18 such that after the proximal portion of the trigger 22 is pulled toward the handle portion 18 and the force applied by the surgeon to the trigger 22 is released, the trigger 22 can again be biased into the position shown in FIG. 1, for example. Such biasing can cause the actuation mechanism 24 to move proximally or remain proximally positioned within the elongate shaft 12 owing to the attachment between the distal portion of the trigger 22 and the proximal portion of actuation mechanism 24. The biasing can be accomplished by any suitable biasing member.

In one embodiment, referring to FIGS. 1-5, the first portion 26 can comprise a first face 44 at least partially or fully surrounding the aperture 30. The first portion 26 can also optionally comprise one or more staple cavities 46 defined in the first face 44. In one embodiment, the one or more staple cavities 46 can be formed in a staple cartridge 49 and a top surface 50 of the staple cartridge 49 can form a portion of the first face 44 and/or can be positioned flush with a plane of the first face 44. If the staple cartridge 49 is provided, the first portion 26 can define a receiving slot into which the staple cartridge 49 can be removably positioned. A staple 38 can be removably positioned within each staple cavity 46.

In various embodiments, the first portion 26 can also comprise the cutting member 40 and the staple driver member 42. The staple driver member 42, upon a force applied to it by the actuation mechanism 24, can drive the cutting member 40 and the staples 38 distally into tissue positioned intermediate the first portion 26 and the second portion 28. In one embodiment, the staple driver member 42 can be configured to move the one or more staples 38 between a first stored position in which the staples 38 are at least partially positioned within the staple cavities 46 and a second position in which the staples 38 are at least partially deployed from the staple cavities 46 into the tissue positioned intermediate the first face 44 of the first portion 26 and a second face of the second portion 28.

In one embodiment, the first portion 26 can also comprise a first electrode 54, such as an electrode comprising an arcuate or circular shape, for example, that can at least partially surround the aperture 30. In one embodiment, the first electrode 54 can function as a positive electrode that provides energy to the end-effector 20. The first electrode 54 can be positioned one of on and proximate to the first face 44, as discussed in further detail below. In various embodiments, the cutting member 40 and/or the staples 38 can also act as electrodes when driven by the actuation mechanism 24, as described herein. In one embodiment, the first portion 26 can comprise a fuse, such as a positive temperature coefficient material, for example, and an insulator as discussed in further detail herein.

In one embodiment, still referring to FIGS. 1-5, the second portion 28 can comprise a second face 56 that substantially opposes the first face 44 when the projection 32 of the second portion 28 at least partially extends into the aperture 30 of the first portion 26 and is engaged with the actuation member 31. The second portion 28 can function as an anvil having one or more anvil pockets 58 defined in the second face 56. The anvil pockets 58 can receive portions of legs of the staples 38 after those legs extend through tissue to deform portions of those legs and form staples in any suitable manner. The second portion 28 can also comprise a second electrode 60 positioned one of on and proximate to the second face 56. In certain embodiments, the second electrode 60 can comprise an electrically conductive portion of the second portion 28, such as a metal portion, for example. In one embodiment, the second electrode 60 can function as the return electrode, or negative electrode, in combination with the actuation member 31, for example. In such an embodiment, the actuation member 31 can comprise an electrically conductive member or portion or can be attached to a conductive member or portion, such as a wire, for example. In other various embodiments, the actuation member 31 can be comprised of an electrically conductive material, for example. In one embodiment, the second portion 28 can comprise a fuse, such as a positive temperature coefficient material, for example, and an insulator as discussed in more detail herein.

In one embodiment, the fuse 62 can be positioned intermediate or at least partially intermediate the first electrode 54 of the first portion 26 and the second electrode 60 of the second portion 28. In other embodiments, the fuse 62 can be positioned on, attached to, or form a portion of the first portion 26 and/or the second portion 28. In still other embodiments, the fuse can be positioned on portions of the staples 38 and/or within the anvil pockets 58, for example. In various embodiments, the fuse 62 can function like a conventional fuse. In one embodiment, the fuse 62 can selectively interrupt energy flowing from the first electrode 54 to the second electrode 60 to at least inhibit over sealing or over heating of the tissue during sealing of the tissue positioned intermediate the first electrode 54 and the second electrode 60. As will be recognized by those of skill in the art, heat is generated in tissue when energy, such as electrical current, for example, flows from one electrode, such as the first electrode 54, through the tissue, to another electrode, such as the second electrode 60. This heat is caused by the resistance that the tissue provides to the energy flow between the two electrodes. In one embodiment, the fuse 62 can be used to control the amount of heat generated, i.e., by limiting or stopping the energy flow between the electrodes if the temperature of the tissue exceeds a predetermined temperature, such as a temperature of 100 degrees C., for example.

In one embodiment, the fuse 62 can comprise a positive temperature coefficient material (hereafter "PTC material"), for example. As the PTC material increases in temperature, the electrical impedance of the PTC material can increase. Thus, the PTC material can become power limiting when the temperature of the PTC material rises above a desired level and, thus, the impedance can rise above the desired level. In one embodiment, if a PTC material is used, a constant voltage source can be used. The electrical characteristics of the heating thus can be sensed to indirectly sense tissue temperature. Examples of PTC materials and their functions are described in greater detail in U.S. Pat. No. 5,624,452 to Yates, entitled HEMOSTATIC SURGICAL CUTTING OR STAPLING INSTRUMENT, which was issued on Apr. 29, 1997 U.S. Pat. No. 6,929,644 to Truckai et al., entitled ELECTROSURGICAL JAW STRUCTURE FOR CONTROLLED ENERGY DELIVERY, which was issued on Aug. 16, 2005, U.S. Pat. No. 6,770,072, to Truckai et al., entitled ELECTROSURGICAL JAW STRUCTURE FOR CONTROLLED ENERGY DELIVERY, which was issued on Aug. 3, 2004, and U.S. Pat. No. 6,929,622 to Chian, entitled SAFETY SYRINGE CYLINDER, which was issued on Aug. 16, 2005, the entire disclosures of which are hereby fully incorporated by reference.

In one embodiment, temperature measuring devices or sensors, such as thermocouples, RTD's (resistive thermal devices), thermistors, and other suitable devices can be embedded at strategic locations within the end-effector 20 or other end-effectors or end-effector assemblies to sense the temperature of the tissue positioned within the end-effector 20. As a result, the delivery of energy to at least one of the electrodes can be controlled in response to feedback from these devices, for example.

In one embodiment, the surgical instrument 10 can be configured to supply energy, such as electrical energy, RF energy, ultrasonic energy, and/or thermal energy, for example, to the tissue compressed between the first face 44 and the second face 56 using the first and second electrodes 54 and 60 to seal or otherwise energize the tissue. As discussed above, the heat can be generated by the resistance to energy flow between the first and second electrodes 54 and 60 or other electrodes that the tissue creates. In various embodiments, the surgical instrument 10 can comprise an activation button 64 or a trigger on the handle portion 18 configured to cause the energy to flow to the first electrode 54, for example, when depressed or retracted. The activation button 64 can essentially act as a switch that is closed when the activation button 64 is depressed. The switch can remain closed until a predetermined time has lapsed to ensure adequate tissue sealing. In one embodiment, the switch can be normally-open such that energy does not flow to the end-effector at undesirable times. In other embodiments, the trigger 22 can activate the energy flow or can contact a switch when the proximal end of the trigger 22 is moved toward the handle portion 18 to allow the energy to flow to the first electrode 54 or another suitable electrode.

In various embodiments, referring to FIG. 4, the handle portion 18 can comprise one or more energy inputs, such as input or terminal 66, for example, which can be operably coupled with an energy source 68, such as a voltage source, a direct current source, an RF, and/or an ultra-sonic source, for example. Suitable energy sources are known in the art. In various embodiments, the energy source 68 can provide energy to the surgical instrument 10 and at least to the first electrode 54, wherein the magnitude, duration, wave form, and/or frequency, for example, of the energy can be sufficiently controlled or modulated, by a controller 70, for example, to provide a desired amount of energy to the surgical instrument 10 and/or the end-effector 20 of the surgical instrument 10. In various embodiments, the activation button 64 can be configured to operably support a switch or a trigger, for example, which can be configured to electrically couple the energy source 68 with a first electrical conductor 70 of the surgical instrument 10 such that the energy supplied to the input 66 can be transmitted to the end-effector 20 and/or one of the electrodes.

In various embodiments, further to the above, the first electrical conductor 70 of the surgical instrument 10 can comprise a wire, such as insulated wire, for example, which can extend between the input 66 and the activation button 64 and extend between the activation button 64 and the first electrode 54, for example. As discussed above, the activation button 64 can act as a switch to allow energy to pass through the first electrical conductor 70 from one side of the activation button 64 to the other side of the activation button 64 when the activation button 64 is depressed or engaged. The energy can then be in electrical communication with the first electrode 54, for example, until the activation button 64 is released or until a predetermined time has lapsed, such as after 2 to 6 seconds, after 4 seconds, after 5 to 20 seconds, or after 10 to 15 seconds, for example. In one embodiment, the first electrical conductor 70 can comprise a conductive insert, comprised of copper or other conductive material, for example, which can be at least partially positioned within an insulative jacket or sheath, for example. In certain circumstances, the insulative jacket can be molded over the first electrical conductor 70 during an injection molding process, for example.

In one embodiment, energy can be transmitted from the first electrical conductor 70 to the first electrode 54, pass through the tissue compressed intermediate the first portion 26 and the second portion 28, and then flow to the second electrode 60. The second electrode 60 can be in electrical communication with a second electrical conductor 72. In one embodiment, the second electrical conductor 72 can be formed with the activation member 31, a portion of the activation member 31, or can be an electrical conductor attached to, formed on, formed within, or positioned within the activation member 31. As a result, the energy can pass from the second electrode 60 to a contact 59 on the projection 32 or the actuation member 31 to the second electrical conductor 72 to an electrical output or terminal 74 and back to the energy source 68. The contact 59 can be in electrical communication with the second electrode 60. In other embodiments, a second electrical conductor can extend from a contact on the distal end or portion of the actuation member 31 to the electrical output or terminal 74. The contact 59 can be in conductive communication with the second electrode 60 when the projection 32 is engaged with the actuation member 31 such that return energy can flow to the output or terminal 74 and then back to the energy source 68 to complete the circuit of the energy source 68.

In various embodiments, insulative materials or non-conductive portions can be suitably positioned within the end-effector 20 and/or the surgical instrument, such that the energy can flow appropriately along a predetermined path through the end-effector 20 and/or the surgical instrument 10. Those of skill in the art will recognize the suitable placement of the various insulative materials and non-conductive portions within the end-effector 20 and/or the surgical instrument 10.

Figure 6:
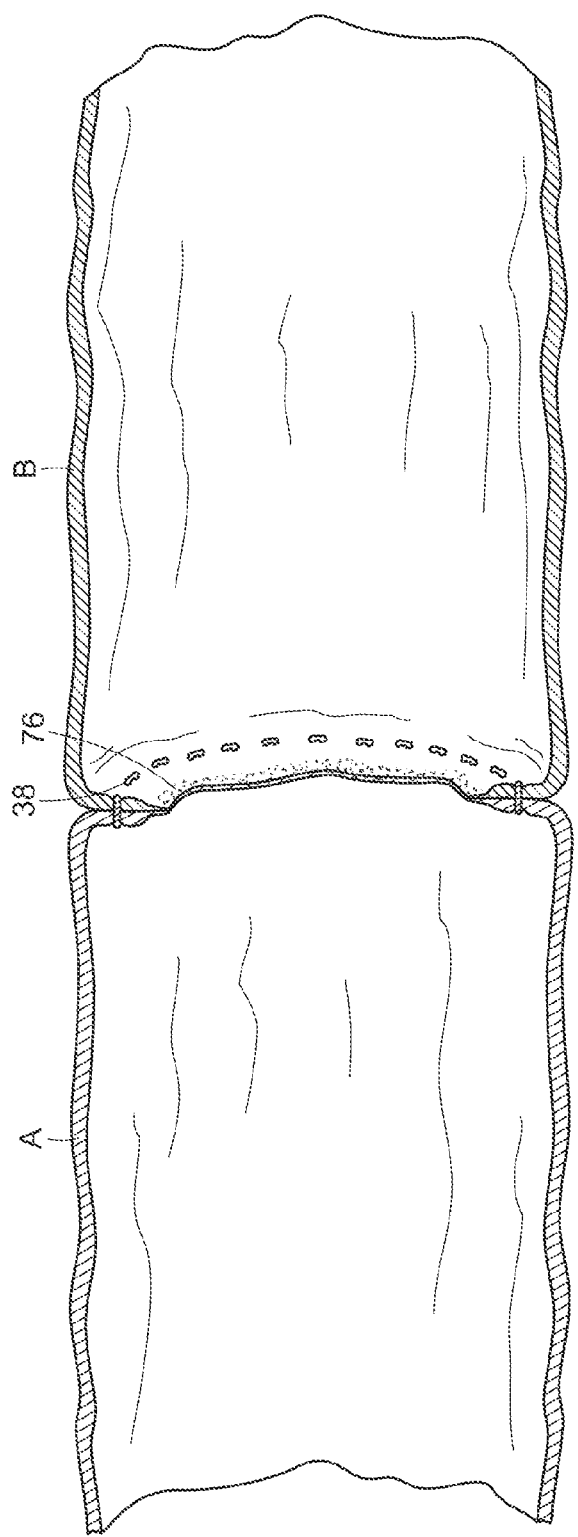
FIG. 6 is a view of a formed anastomosis in tissue after the end-effector of FIG. 5 has been used in accordance with one non-limiting embodiment of the present disclosure.

In one embodiment, referring to FIGS. 5 and 6, in the performance of a surgical anastomotic operation, two tubular pieces of lumen or tubular tissue A and B (e.g., intestinal tissue), can be attached together by the staples 38, and/or by seals 76 created by the energy flowing through the first and second electrodes 54 and 60 or through other electrodes. In various embodiments, it may be desirable to use only the staples 38 or to use only the seals 76 to attach the tubular tissue A to the tubular tissue B, depending on the wall thickness of the tubular tissue A and B compressed between the first face 44 and the second face 56. In one embodiment, the two pieces of tubular tissue A and B may be attached end-to-end or one piece of the tubular tissue may be attached laterally around an opening formed in the side of another piece of the tubular tissue. In performing the anastomosis with the surgical instrument 10, the two pieces of tubular tissue A and B can first be compressed together intermediate the first face 44 and the second face 56 by rotating the adjustment knob 34 in a clockwise direction, for example. The activation button 64 can then optionally be depressed to allow energy to pass to the first electrode 54, through the fuse 62 or fuses, through the tissue, and to the second electrode 60. The staple driver member 42 can then be driven distally by actuation of the trigger 22 to drive the staples 38 into the tissue and form the staples 38 using the anvil pockets 58 of the second portion 28 (i.e., by deforming a portion of the legs of the staples 38). At the same time, the cutting member 40 can be driven distally by the same actuation of the trigger 22 to cut the excess tissue positioned intermediate the first portion 26 and the second portion 28. In other embodiments, an additional trigger (not illustrated) can be provided such that one trigger drives the staple driver member 42 distally and the other trigger drives the cutting member 40 distally, for example. As a result of the cutting member 40 being driven distally, a donut-shaped section of tissue can be severed from each of the tubular pieces of tissue A and B by the cutting member 40. The tubular tissue A and B joined by the staples 38 and/or the seal 76 can be released from being compressed intermediate the first face 44 and the second face 56 by rotating the adjustment knob 34 in the counter-clockwise direction, for example, to thereby move the actuation member 31 distally and move the second portion 28 away from the first portion 26. The surgical instrument 10 can then be removed from the surgical site by pulling the end-effector 20 through the circular opening between the pieces of tubular tissue A and B attached by the staples 38 and/or the seal 76.

In one embodiment, the cutting member 40 and/or the staples 38 can function as an additional or a third electrode. In other embodiments, the cutting member 40 can function as a third electrode and the staples 38 can function as a fourth electrode, or vice versa, for example. In such embodiments, the cutting member 40 and/or the staples 38 can comprise a conductive material, such as a metal, for example, such that the energy from the energy source 68 can flow therethrough. In one embodiment, the input or terminal 66 can be in electrical communication with an electrical conductor (not illustrated) formed with, formed on, positioned on, attached to, positioned within, or formed of the actuation mechanism 24. As a result, when the actuation mechanism 24 is brought into contact with the staple driver member 42, the cutting member 40 and/or the staples 38 can be energized with the energy owing to the fact that the staple driver member 42, the cutting member 40, and/or the staples 38 can comprise electrically conductive portions or can be comprised of electrically conductive materials, for example. The energy can flow through the staples 38 and/or the cutting member 40, through the tissue compressed between the first face 44 and the second face 56, and to the second electrode 60 and exit the surgical instrument 10 through the second electrical conductor 72, as discussed above. The energy can also flow through the fuse 62 or another suitable fuse. In other embodiments, the energy can flow through the staples, through the tissue, and be returned to the energy source 68 using the cutting member 40 or the second electrode 60 as a return electrode, for example. Here, again, the energy can also flow through the fuse 62 or another suitable fuse. In one embodiment, a separate electrical conductor (not illustrated) can be provided in communication with the cutting member 40 to assist the cutting member 40 in acting as the return electrode for the energy passing through the tissue from the staples 38. The separate electrical conductor can be used to complete the circuit with the energy source 68. In one embodiment, by energizing the staples 38 and/or the cutting member 40, a seal can be created at the site of piercing and/or cutting of the tissue (i.e., where the staple legs pierce the tissue and/or where the cutting member 40 cuts the tissue), thereby reducing bleeding through the creation of a seal at the piercing and/or cutting site. In one embodiment, energy flowing through the staples 38 as they are fired can tend to have its highest flux density at the tips of the staples 38 owing to the tips being pointed (minimum surface area) and the closest to the return electrode. In various embodiments, energy flowing through the cutting member 40 can also have its highest flux density at the tip of the cutting member 40 owing to the tip having a reduced surface area compared to the remainder of the cutting member 40. The above can result in enhanced mechanical sharpness and reduced force to fire of the staples 38 and/or the cutting member.

In one embodiment, the activation button 64 can be used to allow energy to flow to the staples 38 and/or to the cutting member 40. Although not illustrated, a separate activation button can also be used to allow energy to pass to the staples 38 and/or to the cutting member 40. The separate activation button can be configured and operate similar to the activation button 64 described above. In other embodiments, other convention types of activation buttons or switches can be used with the surgical instrument 10, for example.

In various embodiments, a separate energy source (not illustrated) can be used to provide energy to the cutting member 40 and/or the staples 38 for example. In such an embodiment, a circuit can be created through the use of electrical conductors from the separate energy source, to the cutting member 40 and/or the staple driver member 42, and back to the separate energy source. In one embodiment, the separate energy source can be similar to or the same as the energy source 68 described above and can be controlled by a controller similar to or the same as the controller 70.

By providing energy to the cutting member 40 and/or the staples 38, a seal can be created where the cutting member 40 cuts the tissue and/or where legs of the staples 38 pierce the tissue. These seals at the point of tissue cutting and/or piercing can reduce bleeding of the tissue. In one embodiment, the seals formed where the cutting member 40 cuts the tissue and/or where the legs of the staples 38 pierce the tissue can be used to seal the tissue in place of the seal 76 formed by the first and second electrodes 54 and 60. In other embodiments, the seals formed where the cutting member 40 cuts the tissue and/or where the legs of the staples 38 pierce the tissue can be used to seal the tissue as a supplementary seal to the seal 76 formed by the first and second electrodes 54 and 60.

In various configurations, by using more than two electrodes of the end-effector 20, the thermal spread of heat within the tissue compressed between the first face 44 and the second face 56 can be minimalized thereby reducing heating of the tissue adjacent to the end-effector 20 (i.e., tissue outside of the end-effector 20). Such minimalization can occur owing to a controlled path of the energy through the various electrodes.

In the embodiments described below, like numerals (e.g., 26, 126, 126', 226 etc.) describe similar components, as those described above, unless otherwise indicated. A full description of each like numbered component below has been omitted for brevity.

Figure 7A:
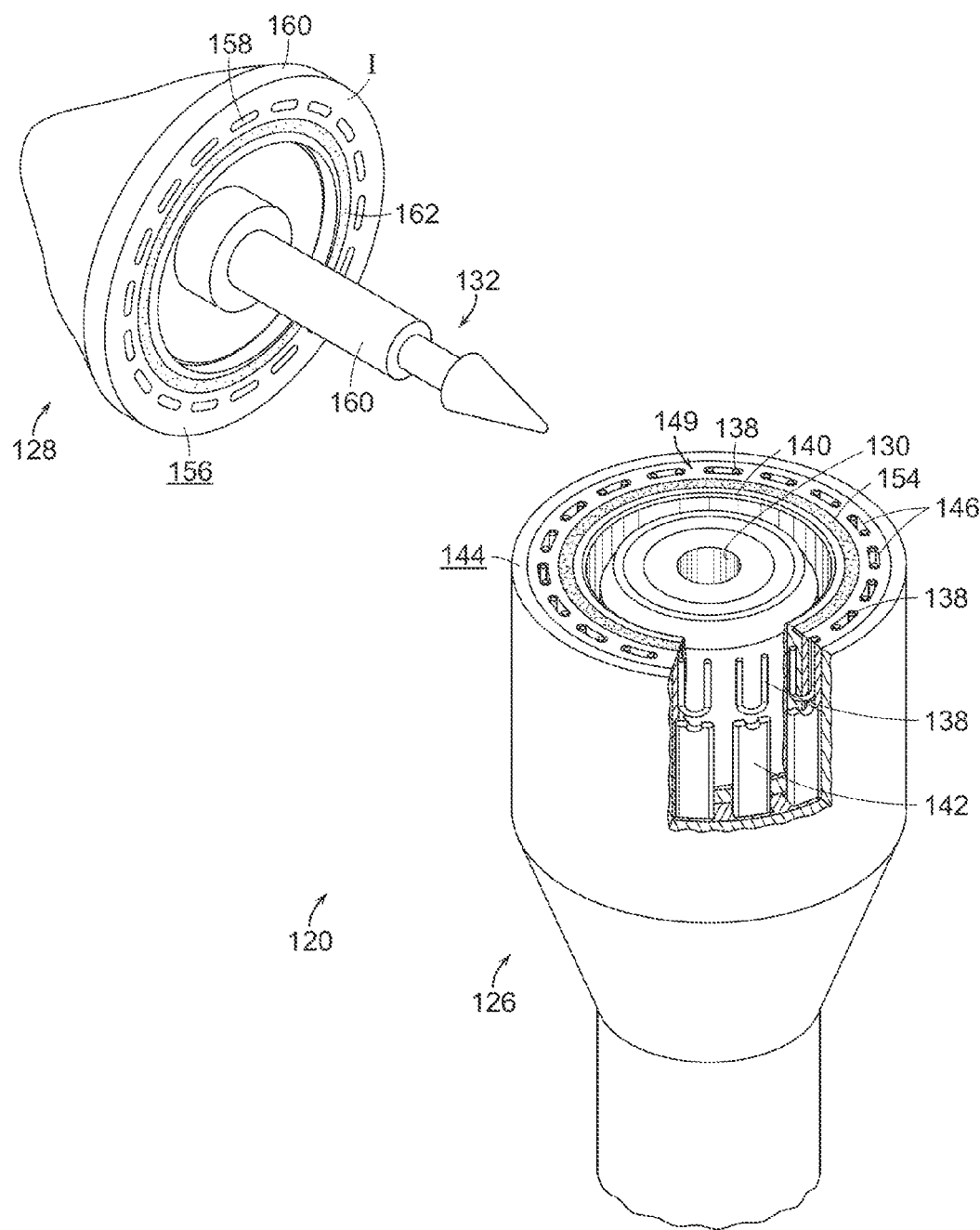
FIG. 7a is a perspective view of an end-effector in accordance with one non-limiting embodiment of the present disclosure.

In one embodiment, referring to FIG. 7a, an end-effector 120 is disclosed. The end-effector 120 can comprise a first portion 126 and a second portion 128. The first portion 126 can comprise staple cavities 146 that can be configured to each receive a staple 138, as explained in greater detail above. In one embodiment, the first portion 126 can also be configured to receive a staple cartridge 149 that comprises the staple cavities 146 and the staples 138 and fits at least partially within a receiving slot in the first portion 126. The staples 138 can be driven distally toward the second portion 128 by a staple driving member 142, similar to that explained above. The first portion 126 can comprise a cutting member 140 configured to cut tissue, a first electrode 154, and an aperture 130. The second portion 128 can comprise a projection 132 configured to be at least partially positioned within the aperture 130, a second electrode 160, a fuse 162, such as PTC material, for example, and anvil pockets 158. In FIG. 7a, the second portion 128 is not connected to the first portion 126 for clarity in illustration. In one embodiment, the first electrode 154 can be positioned radially inwardly of the staple cavities 146 and radially outward from the cutting member 140 on the first portion 126. The anvil pockets 158 can be aligned with the staple cavities 146 when the first portion 126 is engaged with the second portion 128 such that they can deform the staple legs when the staples 138 are pushed distally. Similarly, the first electrode 154 can be aligned with the fuse 162 when the first portion 126 is engaged with the second portion 128. As a result, a seal can be formed in tissue positioned intermediate the first portion 126 and the second portion 128 between a cutting line formed by the cutting member 140 and a staple line formed by the staples 138. In various embodiments, portions of the first face 144, the second face 156, and/or other portions of the end-effector 120 can comprise insulative materials "I" such that energy flows from the first electrode 154 through the fuse 162 to the second electrode 160. If the insulative materials "I" are not provided, the energy may flow in undesirable directions. In one embodiment, insulative materials (not illustrated) can be provided around the staple cavities 146 and/or around the anvil pockets 158, such that when tissue is compressed intermediate the staple cavities 146 and the anvil pockets 158 and the end-effector 120 is energized, energy will not be attracted to the staples 138 owing to the insulative barrier created by the insulative materials.

Figure 7B:
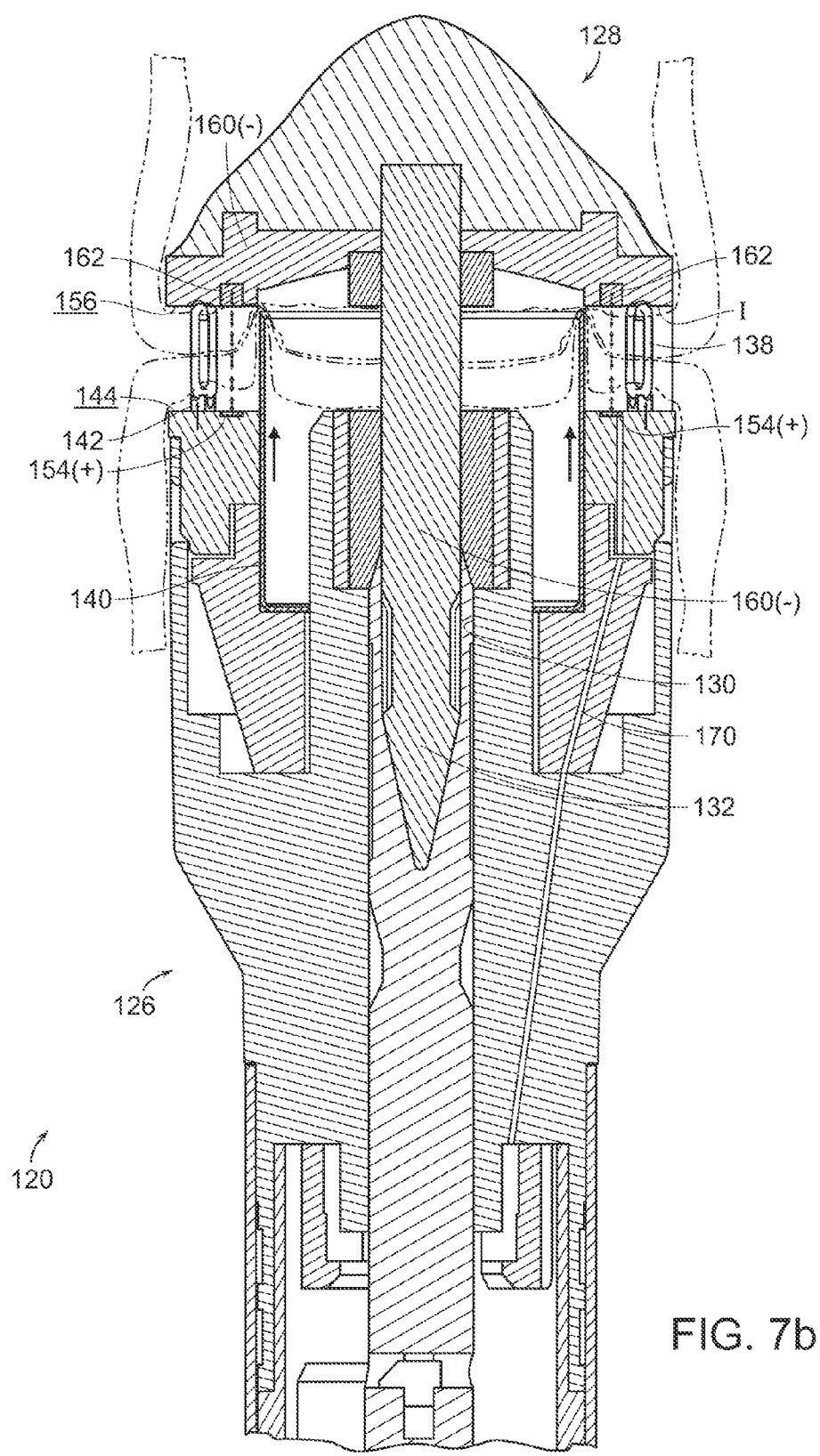
FIG. 7b is a cross-sectional view of the end-effector of FIG. 7a, when a second portion is attached to a first portion in accordance with one non-limiting embodiment of the present disclosure.

In one embodiment, FIG. 7b illustrates a cross-sectional view of the end-effector 120 of FIG. 7a when the first portion 126 is engaged with the second portion 128. In various embodiments, FIG. 7b illustrates the energy flow and the polarity of the first and second electrodes 154 (+) and 160 (−) and an example of where the insulative materials "I" are provided in the end-effector 120.

In one embodiment, although not illustrated, a first electrode can be positioned a depth within a first face of a first portion of an end-effector. A fuse, such as PTC material, for example, can be positioned over the first electrode and be flush, or substantially flush with a plane of the first face of the first portion. In such an embodiment, a portion of a second electrode may be positioned on a second face of the second portion. In one embodiment, the second electrode can be positioned a depth within a second face of the second portion of the end-effector. A fuse, such as PTC material, for example, can be positioned over the second electrode and be flush, or substantially flush with the plane of the second face of the second portion. In other embodiments, the fuse may only be provided on the first portion or the second portion. The portions of the first face and the second face not comprising the fuse can be comprised of an insulative material, such that energy from the first electrode can be directed through the fuse toward the second electrode and may be inhibited from bypassing the fuse to get to the second electrode. As discussed herein, the fuse can limit or stop the energy flow from the first electrode to the second electrode, when appropriate, to maintain the temperature of the tissue in the end-effector within a reasonable sealing temperature, such as 100 degrees C., for example.

Figure 8A:
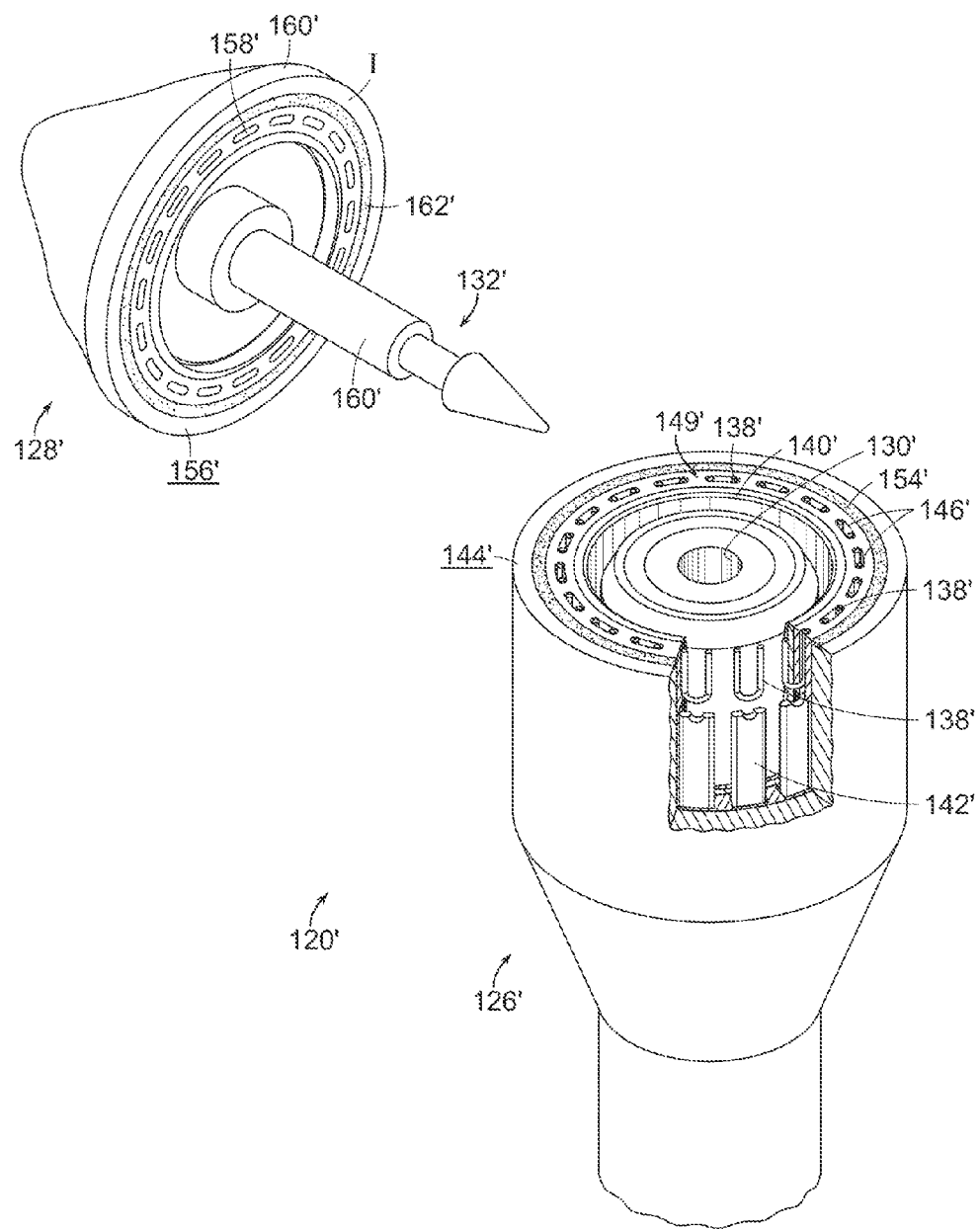
FIG. 8a is a perspective view of an end-effector in accordance with one non-limiting embodiment of the present disclosure.

In one embodiment, referring to FIG. 8a, another end-effector 120' is illustrated. The end-effector 120' can comprise a first portion 126' and a second portion 128'. In such an embodiment, the first portion 126' can comprise a first electrode 154' positioned radially outward from staple cavities 146'. A cutting member 140' can be positioned radially inward from the staple cavities 146'. Correspondingly, a staple driver member 142' can be positioned radially inward as compared to that illustrated in the embodiment of FIG. 7a. Also, in such an embodiment, a fuse 162' on the second portion 128' can be positioned radially outward from the anvil pockets 158'. Similar to the embodiment of FIG. 7a, anvil pockets 158' can be aligned with staple cavities 146' when a projection 132' of the second portion 128' is at least partially positioned within an aperture 130' in the first portion 126' such that staple legs of staples 138' positioned within the staple cavities 146' can be deformed by the anvil pockets 158' when the staples 138' are driven distally toward the second portion 128'. In various embodiments, portions of the first face 144', the second face 156', and/or other portions of the end-effector 120' can comprise insulative materials such that energy flows from the first electrode 154' through the fuse 162' to the second electrode 160'. If the insulative materials are not provided, the energy may flow in undesirable directions. In one embodiment, insulative materials (not illustrated) can be provided around the staple cavities 146' and/or around the anvil pockets 158', such that when tissue is compressed intermediate the staple cavities 146' and the anvil pockets 158' and the end-effector 120' is energized, energy will not be attracted to the staples 138' owing to the insulative barrier created by the insulative materials.

Figure 8B:
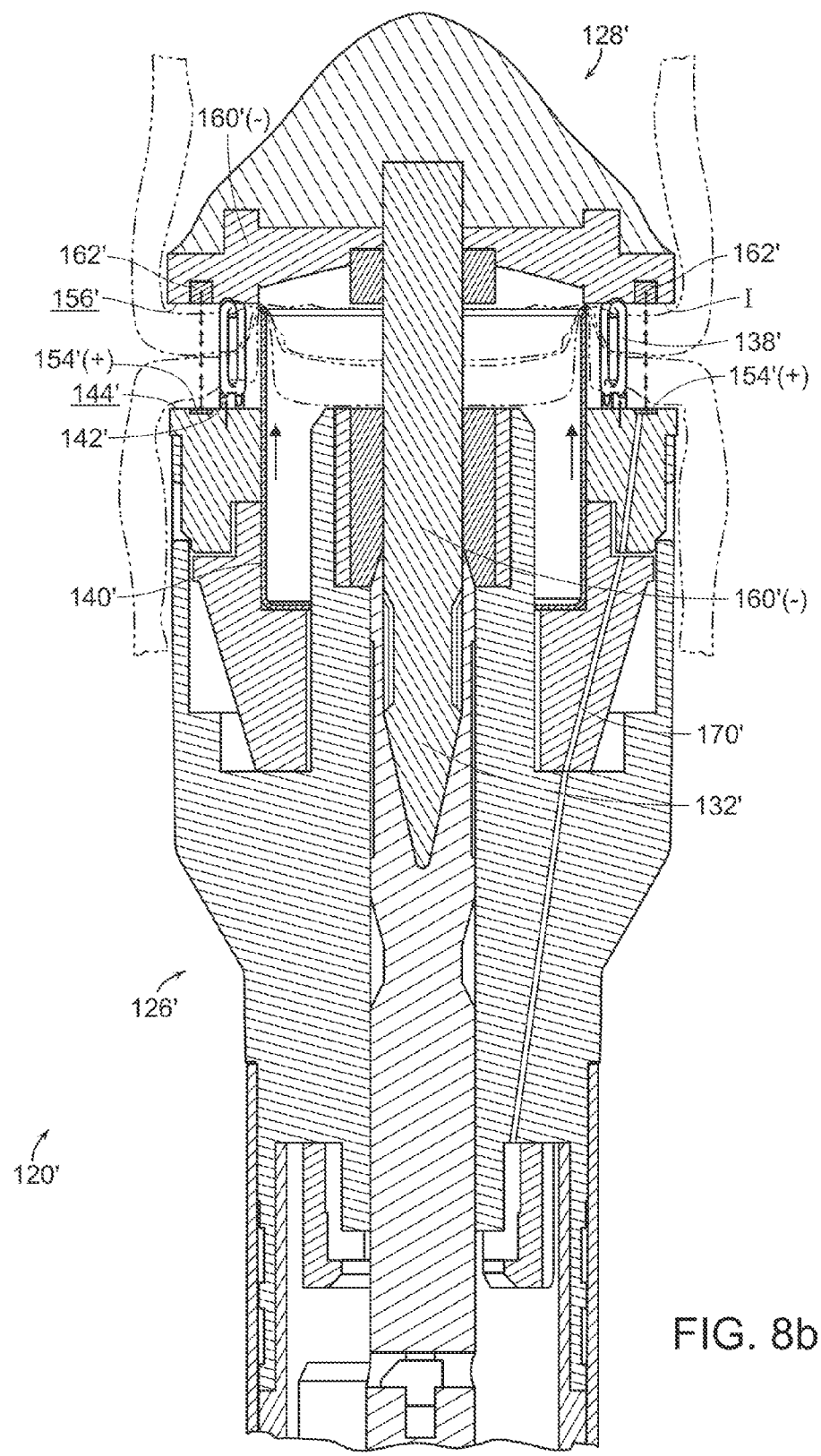
FIG. 8b is a cross-sectional view of the end-effector of FIG. 8a, when a second portion is attached to a first portion in accordance with one non-limiting embodiment of the present disclosure.

In one embodiment, FIG. 8b is a cross-sectional view of the end-effector 120' of FIG. 8a when the first portion 126' is attached to the second portion 128'. In various embodiments, FIG. 8b illustrates the energy flow and the polarity of the first and second electrodes 154' (+) and 160' (–) and an example of where the insulative materials "I" are provided in the end-effector 120'.

Figure 9A:
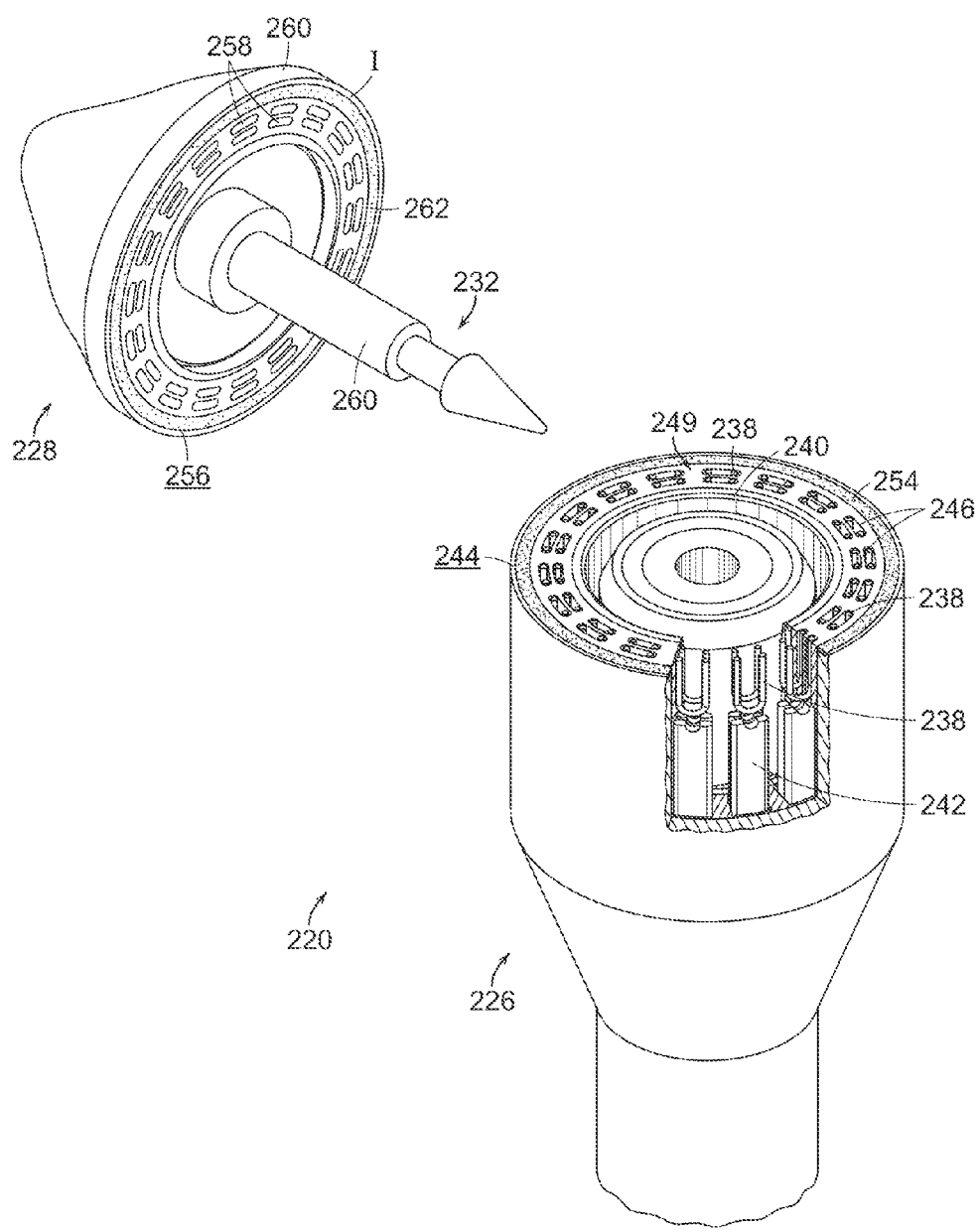
FIG. 9a is a perspective view of an end-effector in accordance with one non-limiting embodiment of the present disclosure.

In one embodiment, referring to FIG. 9a, an end-effector 220 is disclosed which is similar to end-effector 120' above, but that has two rows of staple cavities 246 defined in a first portion 226 and two rows of anvil pockets 258 defined in a second portion 228. In such an embodiment, a staple driving member 242 can drive the two rows of staples 238 into the tissue compressed between the first portion 226 and the second portion 228. The first portion 226 can comprise a first electrode 254 and an aperture 230 configured to at least partially receive a projection 232 of the second portion 228. The first electrode 254 can be positioned radially outward of the two rows of staples 254 and radially outward of a cutting member 240. The cutting member 240 can be positioned radially inward of the two rows of staple cavities 246. The second portion 228 can comprise a fuse 262. The fuse 262 can be positioned radially outward of the two rows of the anvil pockets 258. In various embodiments, portions of the first face 244, the second face 256, and/or other portions of the end-effector 220 can comprise insulative materials "I" such that energy flows from the first electrode 254, through the fuse 262, and to the second electrode 260. If the insulative materials are not provided, the energy may flow in undesirable directions. In one embodiment, insulative materials (not illustrated) can be provided around the staple cavities 249 and/or around the anvil pockets 258, such that when tissue is compressed intermediate the staple cavities 249 and the anvil pockets 258 and the end-effector 220 is energized, energy will not be attracted to the staples 238 owing to the insulative barrier created by the insulative materials.

Figure 9B:
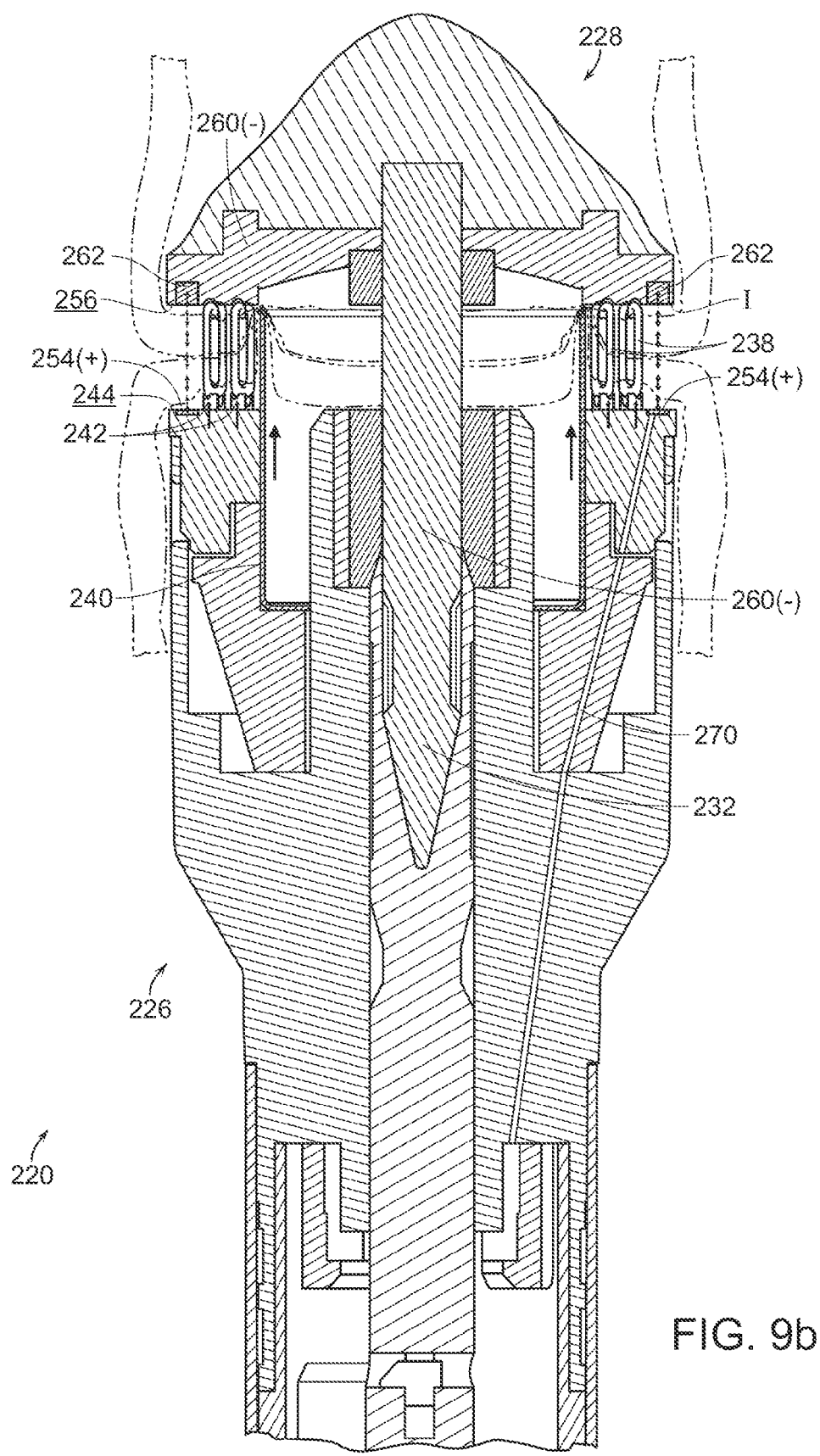
FIG. 9b is a cross-sectional view of the end-effector of FIG. 9a, when a second portion is attached to a first portion in accordance with one non-limiting embodiment of the present disclosure.

In one embodiment, FIG. 9b is a cross-sectional view of the end-effector 220 of FIG. 9a when the first portion 226 is attached to the second portion 228. In various embodiments, FIG. 9b illustrates the energy flow and the polarity of the first and second electrodes 254 (+) and 260 (–) and an example of where the insulative materials are provided in the end-effector 220.

Figure 10A:
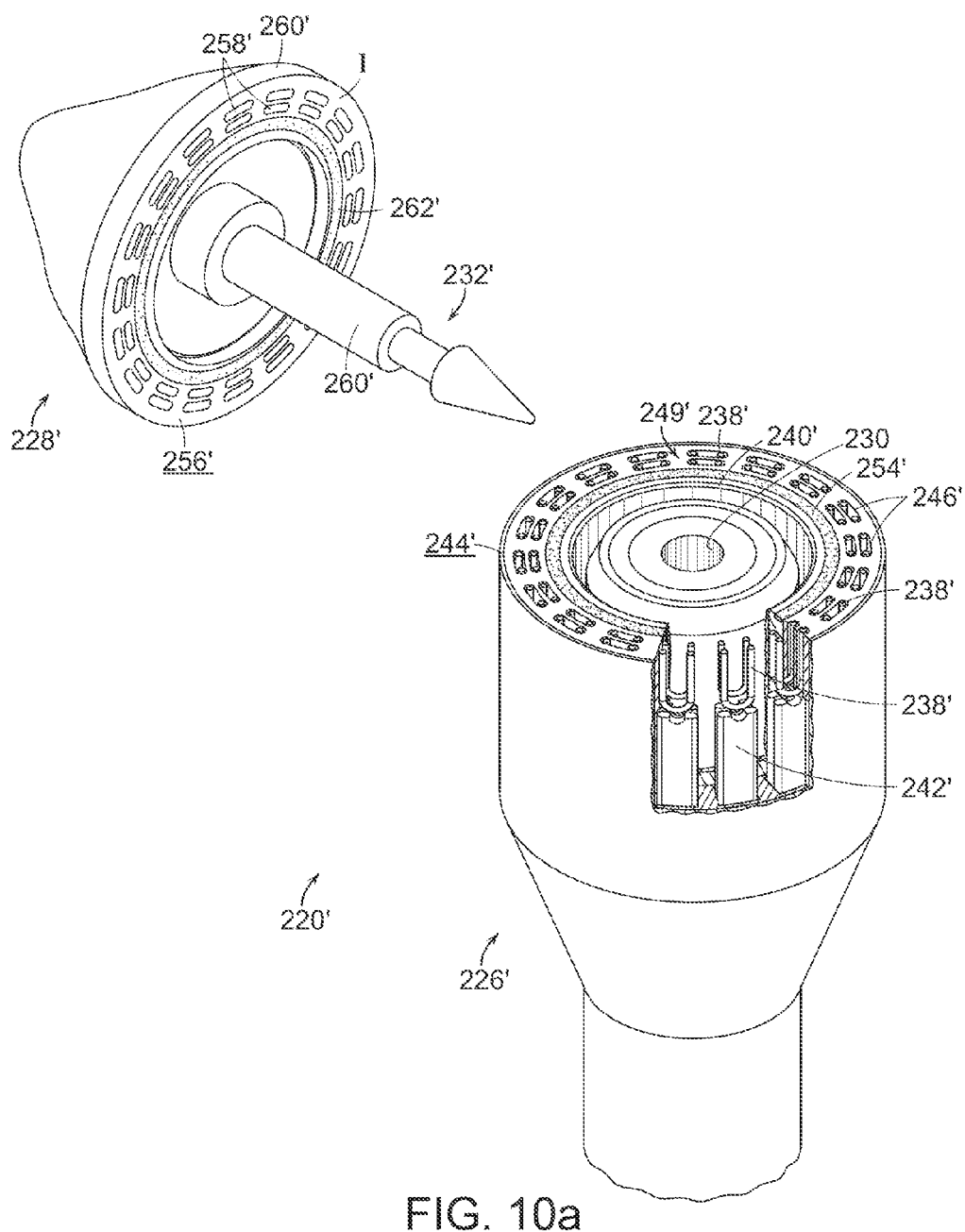
FIG. 10a is a perspective view of an end-effector in accordance with one non-limiting embodiment of the present disclosure.

In one embodiment, referring to FIG. 10a, an end-effector 220' comprising a first portion 226' and a second portion 228' is provided. The end-effector 220' is the same as the end-effector 220 except that a first portion 226' of the end-effector 220' has a first electrode 254' that is positioned radially inward of two rows of staples 238' and except that the second portion 228' has a fuse 262' positioned radially inward of two rows of anvil pockets 258'. A cutting member 240' of the first portion 226' can be positioned radially inward of the first electrode 254'. A staple driving member 242' on the first portion 226' can be positioned accordingly. In various embodiments, portions of the first face 244', the second face 256', and/or other portions of the end-effector 220' can comprise insulative materials "I" such that energy flows from the first electrode 254' through the fuse 262' to the second electrode 260'. If the insulative materials "I" are not provided, the energy may flow in undesirable directions. In one embodiment, insulative materials (not illustrated) can be provided around the staple cavities 249' and/or around the anvil pockets 258', such that when tissue is compressed intermediate the staple cavities 249' and the anvil pockets 258' and the end-effector 220' is energized, energy will not be attracted to the staples 238' owing to the insulative barrier created by the insulative materials.

Figure 10B:
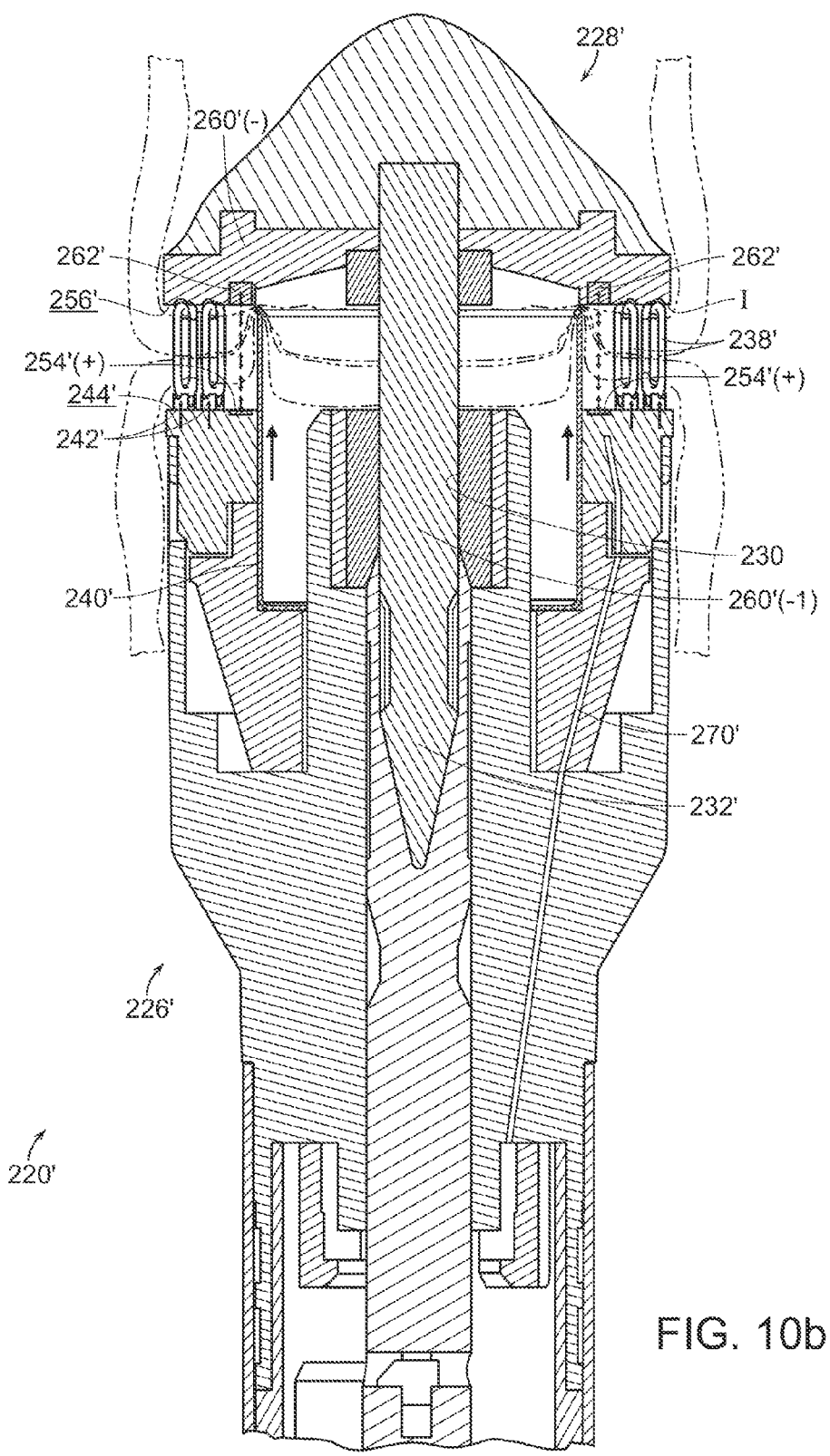
FIG. 10b is a cross-sectional view of the end-effector of FIG. 10a, when a second portion is attached to a first portion in accordance with one non-limiting embodiment of the present disclosure.

In one embodiment, FIG. 10b is a cross-sectional view of the end-effector 220' of FIG. 10a when the first portion 226' is attached to the second portion 228'. In one embodiment, FIG. 10b illustrates the energy flow and the polarity of the first and second electrodes 254' and 260' and an example of where the insulative materials are provided in the end-effector 220'.

Figure 11A:
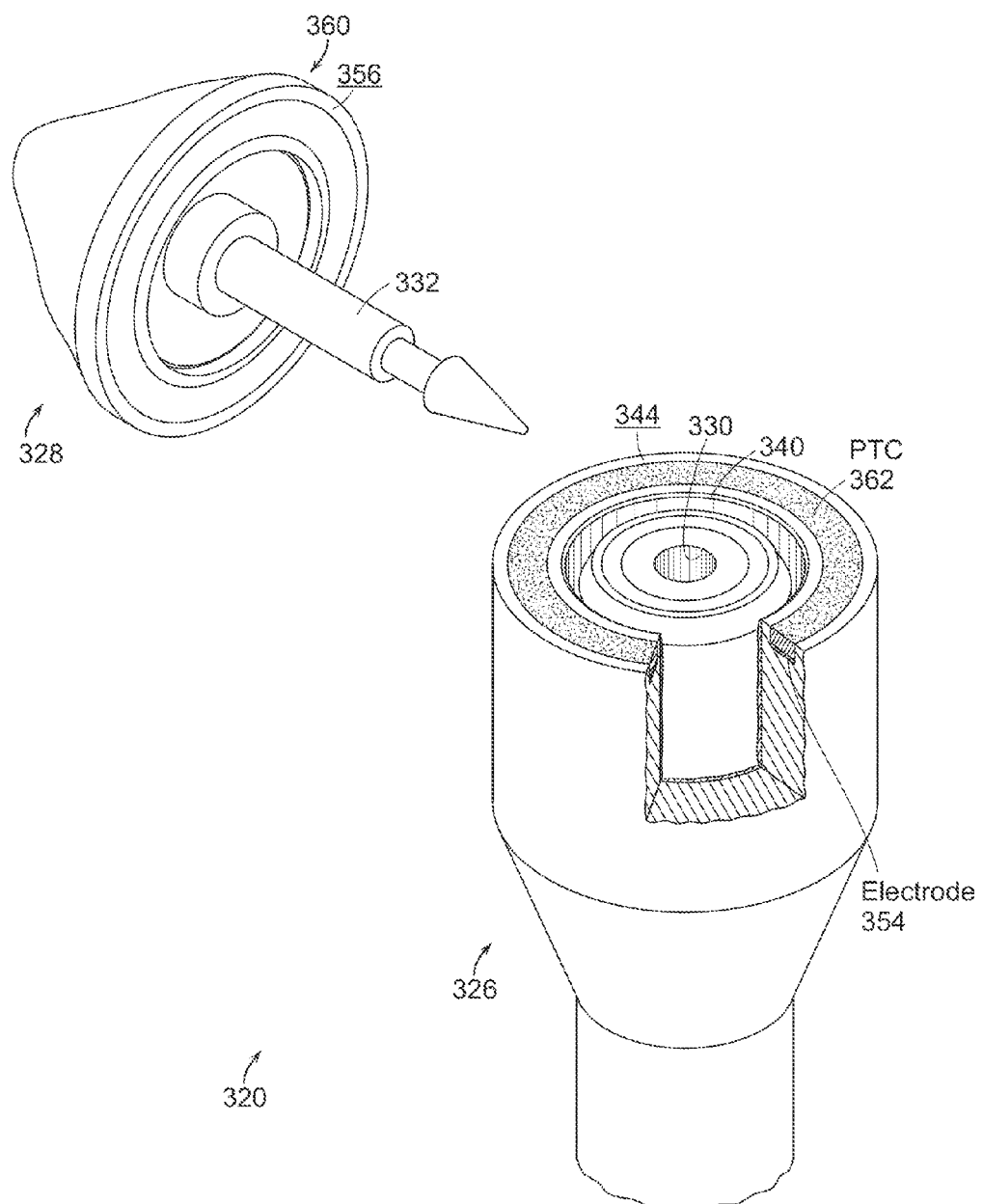
FIG. 11a is a perspective view of an end-effector in accordance with one non-limiting embodiment of the present disclosure.

In one embodiment, referring to FIG. 11a, an end-effector 320 comprises a first portion 326 and a second portion 328. The first portion 326 can comprise a first electrode 354, an aperture 330 configured to receive a projection 332 of the second portion 328, and optionally a fuse 362, such as PTC material, for example. The first portion 326 can comprise a cutting member 340 positioned radially inward of the first electrode 354. The second portion 328 can comprise a second electrode 360 and optionally a fuse (not illustrated), such as PTC material, for example. In such an embodiment, fewer or no staples may be required. Such an embodiment may be useful for sealing relatively thin tissue, such as in tissue in the range of 0.25 mm to 1.0 mm or less than 1.0 mm, for example. In various embodiments, portions of the first face 344, the second face 356, and/or other portions of the end-effector 320 can comprise insulative materials such that energy flows from the first electrode 354, through the fuse 362, and to the second electrode 360.

Figure 11B:
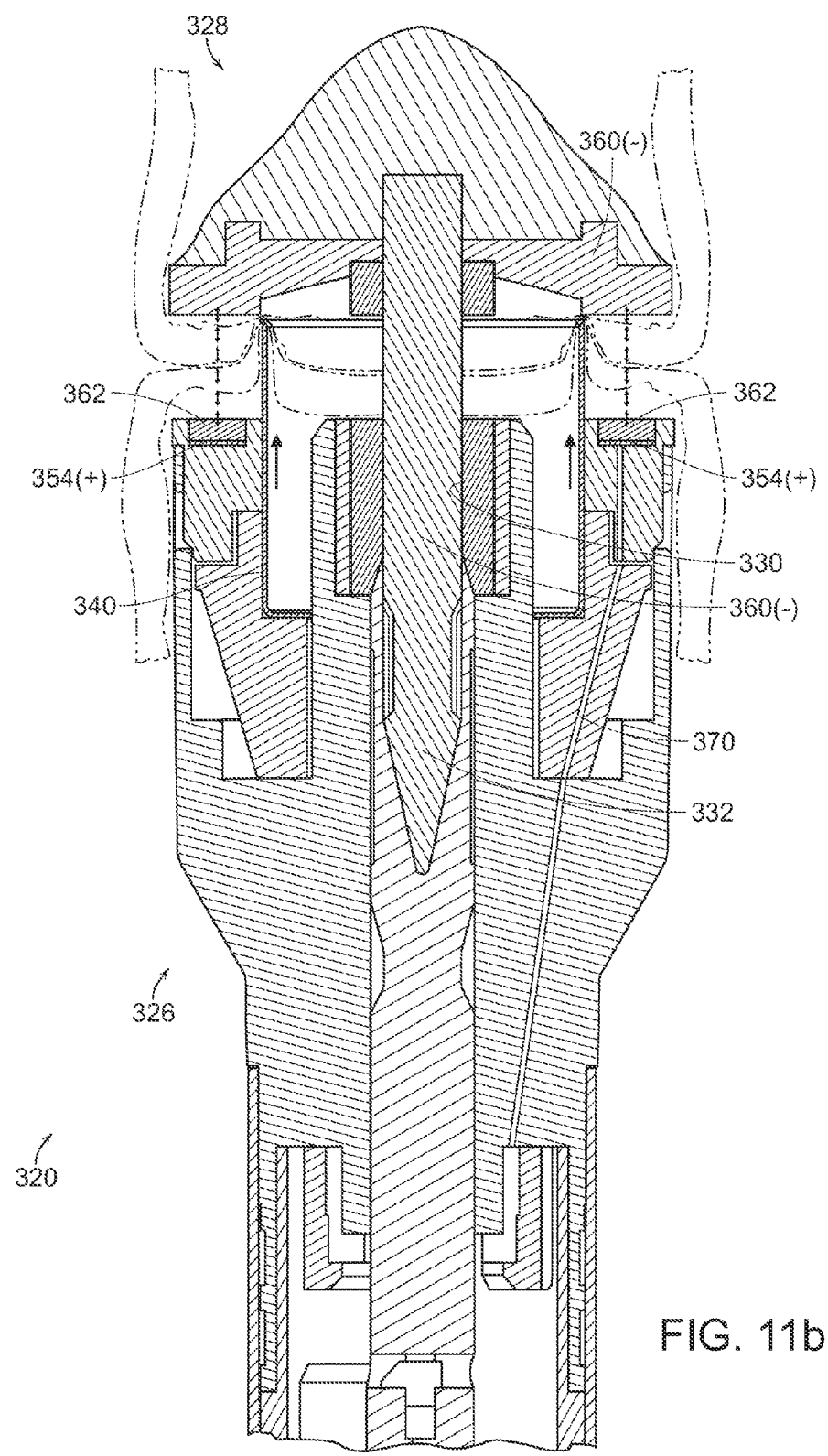
FIG. 11b is a cross-sectional view of the end-effector of FIG. 11a, when a second portion is attached to a first portion in accordance with one non-limiting embodiment of the present disclosure.

In one embodiment, FIG. 11b is a cross-sectional view of the end-effector 320 of FIG. 11a when the first portion 326 is attached to the second portion 328. In various embodiments, FIG. 11b illustrates the energy flow and the polarity of the first and second electrodes 354 (+) and 360 (–).

In one embodiment, the surgical instruments disclosed herein can be operated in at least two ways. In a first method of operation, the second portion of the end-effector can be engaged with the first portion of the end-effector inside separated pieces of tubular tissue, such as an intestine, for example, such that the actuation mechanism is operably engaged with the second portion. Next, the actuation knob can be rotated about its longitudinal axis to compress the tissue positioned intermediate the first portion and the second portion. After the tissue has been compressed to the surgeon's liking or to a suitable predetermined thickness for adequate staple formation in the tissue or sealing of the tissue, possibly using a tissue compression indicator, such as tissue compression indicator 27, for example, the proximal end of the trigger can be moved or pulled toward the handle portion of the surgical instrument to move the actuation mechanism distally within the surgical instrument to fire the staples and move the cutting member distally and optionally to energize the first electrode. In other embodiments, the first electrode can be energized when the activation button is depressed, for example. In various embodiments, energy can also be supplied to the staples, such as the staples 38, and to the cutting member, such as the cutting member 40, as discussed above. By causing the actuation mechanism to move distally, the staples can be fired into the tissue and formed against the second portion of the end-effector or the anvil pockets and the cutting member can be advanced distally to excise the tissue. In one embodiment, the surgeon can hold, pull, or bias the proximal end of the trigger against the handle portion of the surgical instrument, or can hold the activation button in a depressed position, until an indicator informs the surgeon that the tissue has been adequately sealed. In various embodiments, the indicator can be a visual indicator, such as a light emitting diode, for example, or an audible indicator, such as a buzzer or an alarm, for example. In certain embodiments, the time required to fully seal the tissue can be in the range of 2 to 6 seconds, 4 seconds, 2 to 15 seconds, or 3 to 10 seconds, for example.

In one embodiment, further to the above, the surgical instrument can comprise a trigger lockout (not illustrated) configured to maintain the proximal end of the trigger proximal to the handle portion (i.e., in the actuated position) until a suitable sealing time has lapsed. In such an embodiment, upon retraction of the proximal end of the trigger toward the handle portion, a solenoid, for example, positioned proximate to the trigger can be energized to drive a piston from the body of the solenoid and engage an aperture or detent in the trigger to maintain the trigger in the actuated position. The solenoid can be de-energized and the piston can retract into the body of the solenoid after a predetermined tissue sealing time has lapsed to allow the trigger to be biased back into the position illustrated in FIG. 1, thereby ceasing the energy flow to the electrodes. In such an embodiment, energy can flow to the electrodes when the trigger is held in the actuated position. In other various embodiments, the solenoid can be de-energized and the piston can retract into the body of the solenoid when the measured tissue impedance exceeds a threshold value that indicates that the tissue is fully treated and/or sealed. The solenoid can be activated or energized by a switch, or other suitable activation technique, when the trigger is initially moved toward the handle portion. Such a trigger lockout can prevent, or at least inhibit, the surgeon from releasing the trigger or allowing the trigger to be biased into the positioned illustrated in FIG. 1 prior to the seal being fully formed in the tissue compressed intermediate the first portion and the second portion. Such a feature can prevent, or at least reduce, the chance that a weak or unsuitable seal is formed in the tissue.

In other various embodiments, other suitable trigger lockout devices can be used and are within the scope of the present disclosure. Such trigger lockout devices are within the skill of those of ordinary skill in the art.

In one embodiment, a similar solenoid can be operably engaged with a portion of the activation button. The solenoid can be activated or energized when the activation button is depressed. While energized, the piston of this solenoid can be extended to engage a portion of the activation button to hold the activation button in the depressed position and maintain energy flow to the electrodes for a predetermined or suitable period of time. The solenoid can be de-energized and the piston can then be retracted and withdrawn from contact with the portion of the activation button after the predetermined or suitable period of time has passed to allow energy flow to the electrodes to cease.

In the second method of operation, the second portion of the end-effector can be engaged with the first portion of the end-effector inside separate pieces of tubular tissue, such as an intestine, for example, such that the actuation member is operably engaged with the second portion. Next, the actuation knob can be rotated about its longitudinal axis to compress the tissue positioned intermediate the first portion and the second portion. After the tissue has been compressed to the surgeon's liking or to a suitable predetermined thickness for adequate staple formation in the tissue or sealing of the tissue, possibly using a tissue compression indicator, such as tissue compression indicator 27, for example, the surgeon can depress the activation button 64 or other suitable activation button to supply energy to the first electrode or to another electrode. In various embodiments, energy can also be supplied to the staples, such as the staples 38, and to the cutting member, such as cutting member 40, as discussed above. While energy is being supplied to the first electrode, the staples, and/or the cutting member, the trigger can be locked in the biased position illustrated in FIG. 1, such that the proximal end of the trigger cannot be moved toward the handle portion, to thereby prevent firing of the staples and distal movement of the cutting member, until the first electrode, the staples, and/or the cutting member have been energized for a period of time long enough to form a suitable seal in the tissue. In one embodiment, the proximal end of the trigger can be prevented from moving toward the handle portion using a trigger lockout, similar to the trigger lockout comprising a solenoid described above, for example. After a predetermined sealing time has lapsed, the trigger lockout can release from the trigger (e.g., the piston of the solenoid is retracted into a body of the solenoid) thereby allowing the proximal end of the trigger to be moved toward the handle portion to fire the staples and move the cutting member distally. Other methods of operation will be recognized as part of the present disclosure by those of skill in the art.

Figure 12:
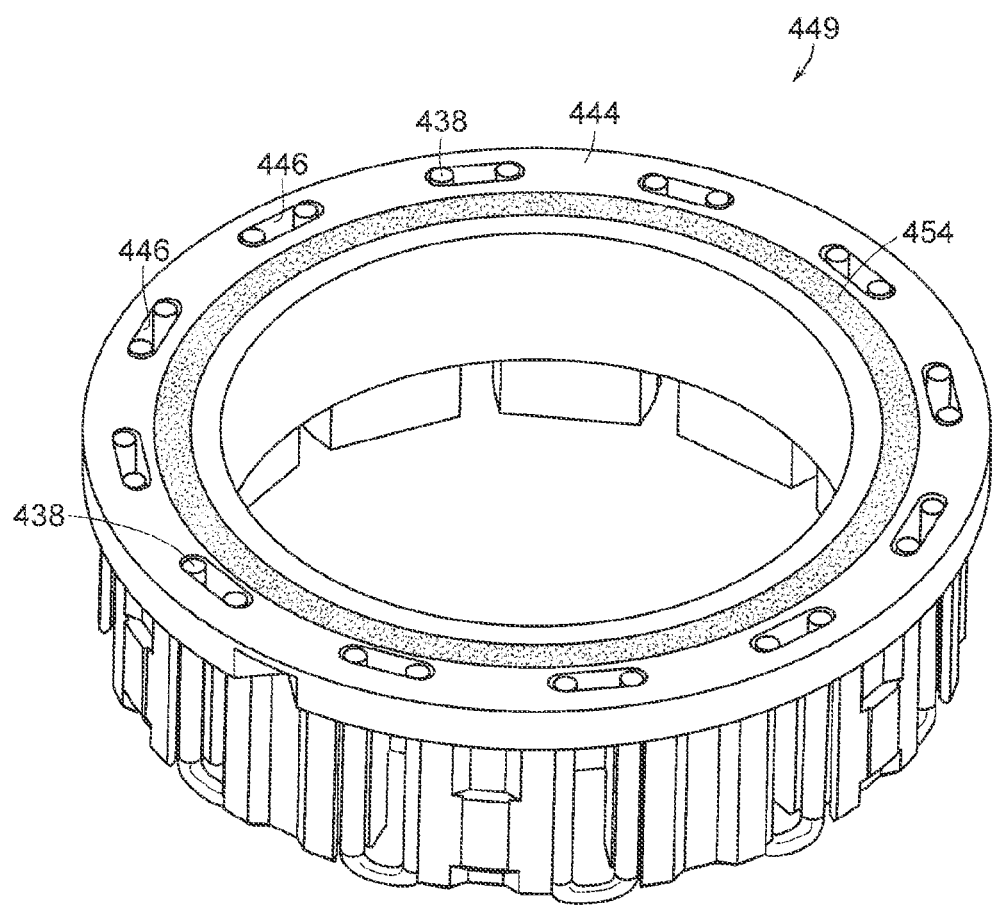
FIG. 12 is a perspective view of a staple cartridge configured to be used in a surgical stapling instrument in accordance with one non-limiting embodiment of the present disclosure.

In one embodiment, referring to FIG. 12, a staple cartridge 449 comprising an electrode 454 is disclosed. The staple cartridge 449 can comprise a face 444 and a tissue-contacting surface having staple cavities 446 defined therein. The staple cavities 446 can each comprise a staple 438 comprising one or more staple legs. The staple cartridge 449 can be configured to be positioned within a receiving slot in a first portion of a surgical instrument, such as the first portion 26 of the surgical instrument 10 described above. The staples 438 can then be driven from the staple cartridge 444 distally into tissue using a staple driver member, such as the staple driver member 42 of the surgical instrument 10 described above. In one embodiment, the staple driver member 42 can be comprised of a PTC material or the staple contacting surface of the staple driver member 42 can be comprised of a PTC material. In one embodiment, the electrode 454 can be positioned radially inward of the staple cavities 446, for example. The electrode 454 can be engaged with an electrical conductor such that energy can flow to the electrode at an appropriate time. Although one embodiment of the staple cartridge 449 is illustrated in FIG. 12, those of skill in the art will recognize that other configurations of staple cartridges are within the scope of the present disclosure. For example, a staple cartridge could have two rows of staple pockets and/or one or more electrodes. In various embodiments, the staple pockets can be positioned radially inward or radially outward of the electrodes, for example.

Although multiple example embodiments of the first portion and the second portion of the end-effector of the present disclosure are discussed herein, those of skill in the art will recognize that various other configurations are also within the scope of the present disclosure. For example, a first portion of an end-effector can have three sets of staple cavities positioned radially inward or radially outward of an electrode, while the second portion can have a corresponding electrode and/or fuse positioning and anvil pocket positioning. In certain other embodiments, one or more rows of staple cavities can be positioned radially outward from an electrode and one or more rows of staple cavities can be positioned radially inward from the electrode in a first portion of an end-effector. In such an embodiment, a second portion of the end-effector can have corresponding anvil pocket positioning and electrode and/or fuse positioning. In such an embodiment, a staple line can be formed in tissue compressed within the end-effector intermediate one or more rows of staples. Other various embodiments and configurations of the electrodes, the fuse, the staple cavities, and the anvil pockets are envisioned and are within the scope of the present disclosure. It will be understood that the example embodiments presented herein are not intended to limit the scope of the appended claims.

Although the surgical instrument 10 is illustrated and described with a first portion 26 that functions as the staple deploying portion and a second portion 28 that functions as an anvil for deforming the staples, the first portion can function as the anvil and the second portion can function as the staple deploying portion and/or staple cartridge. In such an embodiment, the staples can be positioned within a receiving slot, a staple cartridge, or staple cavities in the second portion and anvil pockets can be positioned within the first portion. A cutting member can also be engaged with the second portion. The electrode configuration can be similar to that discussed above. In such an embodiment, the second portion can be pulled toward the first portion to deploy the staples proximally against the first portion and to move the cutting member proximally toward the first portion.

In one embodiment, the end effector 20 can comprise a tissue thickness indicator (not illustrated) configured to sense a thickness of the tissue positioned intermediate the first face 44 and the second face 56. In various embodiments, the tissue thickness indicator can be positioned on the first face 44, the second face 56, or the first face 44 and the second face 56, for example. In other embodiments, the tissue thickness indicator can be positioned at other suitable locations on the end-effector 20. Suitable tissue thickness indicators will be apparent to those of skill in the art, such as proximity sensors, for example. In one embodiment, the projected tissue compression and projected staple leg deformation can be measured by measuring the impedance of the tissue across the thickness of the tissue, for example. The tissue thickness indicator can be in electrical communication with a processor, such as a microprocessor, for example, which can interpret the signal generated by the tissue thickness indicator and instruct a suitable element accordingly. In one embodiment, the staple driver member 42 can be activated separate from the cutting member 40. In such an embodiment, the staple driver member 42 may only be activated when a sensed tissue thickness is greater than a predetermined tissue thickness threshold. Tissue thicknesses above the predetermined tissue thickness threshold may benefit from staples being deployed into the tissue, while tissue thicknesses below the predetermined tissue thickness threshold may not require staples to be deployed into the tissue. In such an embodiment, only the cutting member 40 and the various electrodes (and not the staple driver member 42) may be activated to create a seal in the tissue owing to the relatively thin nature of the tissue clamped within the end-effector 20. In various circumstances, relatively thin tissue may not require that staples be deployed to effect a suitable seal in the tissue.

In one embodiment, a staple sensor (not illustrated) can be configured to sense when the staple 38 is in the first stored position or at least partially in the first stored position. The staple sensor 38 can also be in electrical communication with the processor described above, or another suitable processor, to interpret a signal received from the staple sensor. When the processor receives an indication from the staple sensor 38 that indicates a staple is not in the first stored position and the tissue thickness is above a predetermined tissue thickness threshold, the processor can activate a lockout device configured to selectively restrict movement of the cutting member 40 and/or the staple driver member 42 relative to the first face 44. In one embodiment, the lockout device can be a solenoid in electrical communication with the processor, for example. When the lockout device is activated by the processor, it can engage the cutting member 40 and/or the staple driver member 42 and restrict their movement relative to the first face 44, thereby preventing, or at least inhibiting, the cutting member 40 and/or the staple driver member 42 from cutting and deploying staples into the tissue clamped within the end-effector 20 at least until a staple is sensed by the staple sensor. In other embodiments, the lockout device can essentially function as a switch and can interrupt energy flow to the various electrodes, for example. In other various embodiments, the surgical instruments of the present disclosure can comprise other suitable sensors, lockout devices, and/or electronic controls as will be recognized by those of ordinary skill in the art.

In one embodiment, FIGS. 13 and 14 illustrate a surgical stapling, sealing, and/or severing instrument 510. The surgical stapling and severing instrument 510 can comprise an end-effector and/or an end-effector assembly 512 configured to be attached to or formed with the surgical instrument 510. The end-effector assembly 512 can comprise an E-beam firing mechanism ("firing bar") 514 or other suitable firing mechanism that can control the spacing of the end-effector assembly 512. In particular, an elongate channel or second jaw 516 (hereafter the terms "elongate channel" and "second jaw" can be used interchangeably) and a pivotally translatable anvil or first jaw 518 (hereinafter the terms "pivotally translatable anvil," "anvil" and "first jaw" can be used interchangeably) can be maintained at a spacing that can assure effective stapling and severing of tissue. In various embodiments, at least one of the first jaw 518 and the second jaw 516 can be movable relative to the other, both of the first jaw 518 and the second jaw 516 can be movable, and/or the second jaw 516 can be movable relative to the first jaw 518, for example.

In various embodiments, the surgical instrument 510 can comprise a handle portion 520 connected to an implement portion 522. The implement portion 522 can comprise a shaft 523 distally terminating in the end-effector assembly 512 or attached to the end-effector assembly 512. The handle portion 520 can comprise a pistol grip 524 toward which a closure trigger 526 can be pivotally drawn by the surgeon to cause clamping and/or closing of the first jaw 518 toward the second jaw 516 of the end-effector assembly 512. A firing trigger 528 can be positioned farther outboard of the closure trigger 526 and can be pivotally drawn by the surgeon to cause the stapling, sealing, and/or severing of tissue clamped within the end-effector assembly 512.

In one embodiment, the closure trigger 526 can first be actuated by the surgeon. Once the surgeon is satisfied with the positioning of the end-effector assembly 512 about the tissue, the surgeon can draw back the closure trigger 526 to its fully closed, locked position proximate to the pistol grip 524. Then, the firing trigger 528 can be actuated by the surgeon. The firing trigger 528 can springedly return to its unfired state when the surgeon removes pressure therefrom. A release button 530, when depressed, on the proximal end of the handle portion 520 can release the locked closure trigger 526 and allow it to return to its unretracted position.

In various embodiments, a closure sleeve 532 can enclose a frame 534, which in turn can enclose a firing drive member 536 that can be positioned by the firing trigger 528. The frame 534 can connect the handle portion 520 to the end-effector assembly 512. With the closure sleeve 532 withdrawn proximally by the closure trigger 526, the first jaw 518 can springedly open, pivoting away from the second jaw 516 and translating proximally with the closure sleeve 532. The second jaw 516 can be configured to receive a staple cartridge 537 comprising at least one staple.

Figure 15:
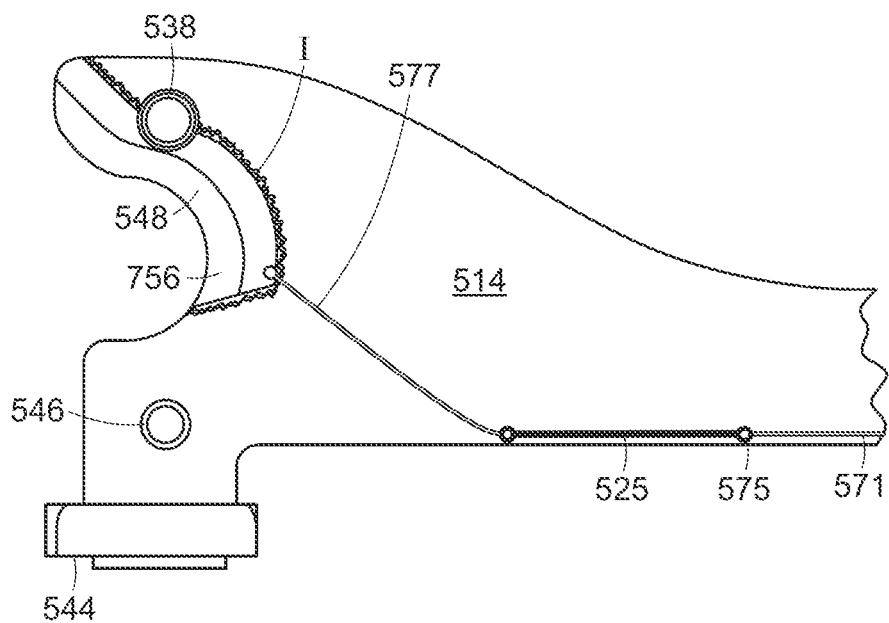
FIG. 15 is a side view of a cutting member of the end-effector assembly of the surgical instrument of FIG. 14 in accordance with one non-limiting embodiment of the present disclosure.
Figure 16:
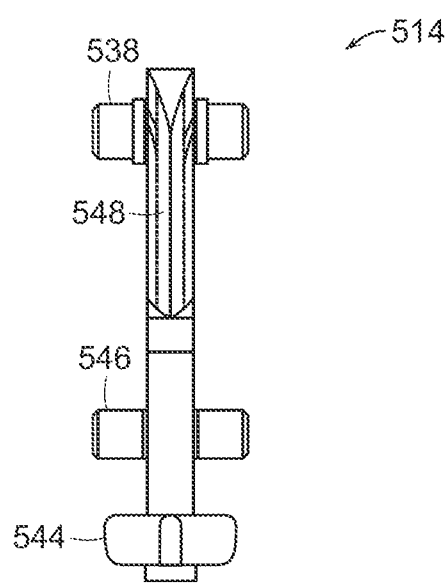
FIG. 16 is a front view of the cutting member of FIG. 15 in accordance with one non-limiting embodiment of the present disclosure.

In one embodiment, referring to FIGS. 14-16, the firing bar 514 can comprise three vertically spaced pins that can control the spacing of the end-effector assembly 512 during firing. In particular, an upper pin 538 can be staged to enter an anvil pocket 540 near the pivot between the first jaw 518 and the second jaw 516. When fired with the first jaw 518 closed, the upper pin 538 can advance distally within a longitudinal anvil slot 542 extending distally through the first jaw 518. Any minor upward deflection in the first jaw 518 can be overcome by a downward force imparted by the upper pin 538. In various embodiments, the firing bar 514 can comprise a lowermost pin, or firing bar cap, 544 that can upwardly engage a channel slot 545 in the second jaw 516, thereby cooperating with the upper pin 538 to draw the first jaw 518 and the second jaw 516 slightly closer together in the event that excess tissue is clamped therebetween.

Figure 17:
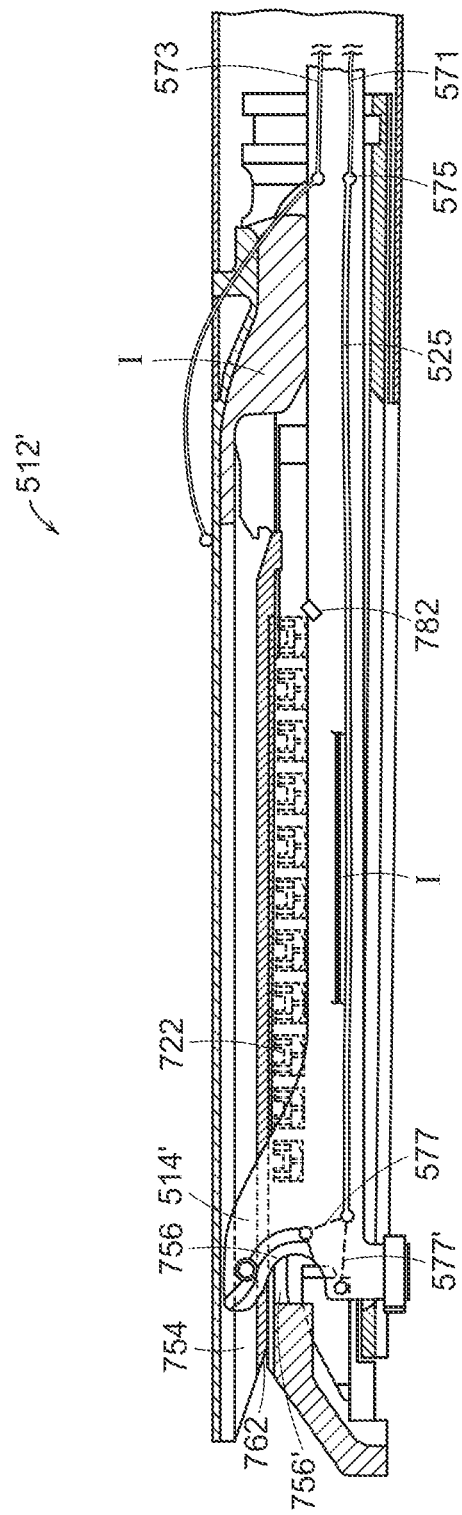
FIG. 17 is a cut-away side view of an end-effector assembly with a cutting member and a driver in the fully extended position in accordance with one non-limiting embodiment of the present disclosure.

In one embodiment, the firing bar 514 can comprise a middle pin 546 that can pass through a firing drive slot 547 formed in a lower surface of the cartridge 537 and an upward surface of the second jaw 516, thereby driving the staples from within the cartridge 537 as described below. The middle pin 546, by sliding against the second jaw 516, can resist any tendency for the end-effector assembly 512 to be pinched shut at its distal end. To illustrate an advantage of the middle pin 546, FIG. 17 illustrates an alternative end-effector assembly 512' that lacks a middle pin on a firing bar 514'. In this illustration, the end-effector assembly 512' can pinch shut at its distal end, which can tend to impair desired staple formation.

In various embodiments, again referring to FIGS. 14-16, a distally presented cutting member 548 between the upper and middle pins 538 and 546 on the firing bar 514 can traverse through a proximally presented, vertical slot 549 in the cartridge 537 to sever tissue clamped within the end-effector assembly 512. The affirmative positioning of the firing bar 514 with regard to the second jaw 516 and the first jaw 518 can assure that an effective cut of the tissue is performed.

In one embodiment, the affirmative vertical spacing provided by the E-Beam firing bar 514 can be suitable for the limited size available for endoscopic devices. Moreover, the E-Beam firing bar 514 can enable fabrication of the first jaw 518 with a camber imparting a vertical deflection at its distal end, similar to the position illustrated in FIG. 17. The cambered first jaw 518 can assist in achieving the desired gap in the end-effector assembly 512 even with the anvil's reduced thickness, which is thus more suited to the size limitations of an endoscopic device.

In various embodiments, the E-Beam firing bar 514 can enable increased applications, especially in combination with a range of configurations of staple cartridges. For instance, a surgeon may select a gray staple cartridge yielding a 0.02 mm tissue gap, a white staple cartridge yielding a 0.04 mm tissue gap, a blue staple cartridge yielding a 0.06 mm tissue gap, and/or a green staple cartridge yielding a 0.10 mm tissue gap. The vertical height of each respective staple cartridge in combination with the length of staples and an integral wedge sled (described in more detail below) can predetermine this desired tissue thickness with the first jaw 518 appropriately vertically spaced by the E-Beam firing bar 514.

In various embodiments, referring to FIGS. 18-21, the handle portion 520 can be comprised of first and second base sections 550 and 552, which can be molded from a polymeric material, such as a glass-filled polycarbonate, for example. In one embodiment, the first base section 550 can comprise a plurality of cylindrical-shaped pins 554, while the second base section 552 can comprise a plurality of extending members 556, each comprising a hexagonal-shaped opening 558 or otherwise shaped opening. The cylindrical-shaped pins 554 can be received within the hexagonal-shaped openings 558 and can be frictionally held therein or otherwise held therein for maintaining the first and second base sections 550 and 552 in assembly.

In one embodiment, a rotating knob 560 can comprise a bore 562 extending completely therethrough for engaging and rotating the implement portion 522 about its longitudinal axis. The rotating knob 560 can comprise an inwardly protruding boss 564 extending along at least a portion of the bore 562. The protruding boss 564 can be received within a longitudinal slot 566 formed at a proximal portion of the closure sleeve 532 such that rotation of the rotating knob 560 can effect rotation of the closure sleeve 532. It will be appreciated that the boss 564 can extend through the frame 534 and into contact with a portion of the firing drive member 536 to effect their rotation as well. Thus, the end-effector assembly 512 (not illustrated in FIGS. 18-21) can rotate with the rotating knob 560.

In one embodiment, a proximal end 568 of the frame 534 can pass proximally through the rotating knob 560 and can comprise a circumferential notch 570 that can be engaged by opposing channel securement members 572 extending respectively from the base sections 550 and 552. Only the channel securement member 572 of the second base section 552 is illustrated. The channel securement members 572 extending from the first and second base sections 550 and 552 can serve to secure the frame 534 to the handle portion 520 such that the frame 534 does not move longitudinally relative to the handle portion 520.

In various embodiments, the closure trigger 526 can comprise a handle section 574, a gear segment section 576, and an intermediate section 578. A bore 580 can extend through the intermediate section 578. A cylindrical support member 582 extending from the second base section 552 can pass through the bore 580 for pivotably mounting the closure trigger 526 on the handle portion 520. A second cylindrical support member 583 extending from the second base section 552 can pass through a bore 581 of the firing trigger 528 for pivotally mounting on the handle portion 520. A hexagonal opening 584 can be provided in the cylindrical support member 583 for receiving a securement pin (not illustrated) extending from the first base section 550.

In one embodiment, a closure yoke 586 can be housed within the handle portion 520 for reciprocating movement therein and can serve to transfer motion from the closure trigger 526 to the closure sleeve 532. Support members 588 extending from the second base section 552 and a securement member 572, which extends through a recess 589 in the yoke 586, can support the yoke 586 within the handle portion 520.

In various embodiments, a proximal end 590 of the closure sleeve 532 can comprise a flange 592 that can be snap-fitted or otherwise fitted into a receiving recess 594 formed in a distal end 596 of the yoke 586. A proximal end 598 of the yoke 586 can comprise a gear rack 600 that can be engaged by the gear segment section 576 of the closure trigger 526. When the closure trigger 526 is moved toward the pistol grip 524 of the handle portion 520, the yoke 586 and, hence, the closure sleeve 532 can move distally, compressing a spring 602 that biases the yoke 586 proximally. Distal movement of the closure sleeve 532 can effect pivotal translational movement of the first jaw 518 distally and toward the second jaw 516 of the end-effector assembly 512 and proximal movement can effect closing, as discussed below.

In various embodiments, the closure trigger 526 can be forward biased to an open position by a front surface 630 interacting with an engaging surface 628 of the firing trigger 628. Clamp first hook 604 that can pivot top to rear in the handle portion 520 about a pin 606 can restrain movement of the firing trigger 528 toward the pistol grip 524 until the closure trigger 526 is clamped to its closed position. The first hook 604 can restrain the firing trigger 528 motion by engaging a lockout pin 607 in the firing trigger 528. The hook 604 can also be in contact with the closure trigger 526. In particular, a forward projection 608 of the hook 604 can engage a member 610 on the intermediate section 578 of the closure trigger 526, the member 610 being positioned outward of the bore 580 toward the handle section 574. The hook 604 can be biased toward contact with the member 610 of the closure trigger 526 and can be engaged with a lockout pin 607 in the firing trigger 528 by a release spring 612. As the closure trigger 526 is depressed, the hook 604 can be moved top to rear, compressing the release spring 612 that is captured between a rearward projection 614 on the hook 604 and a forward projection 616 on the release button 530.

Figure 20:
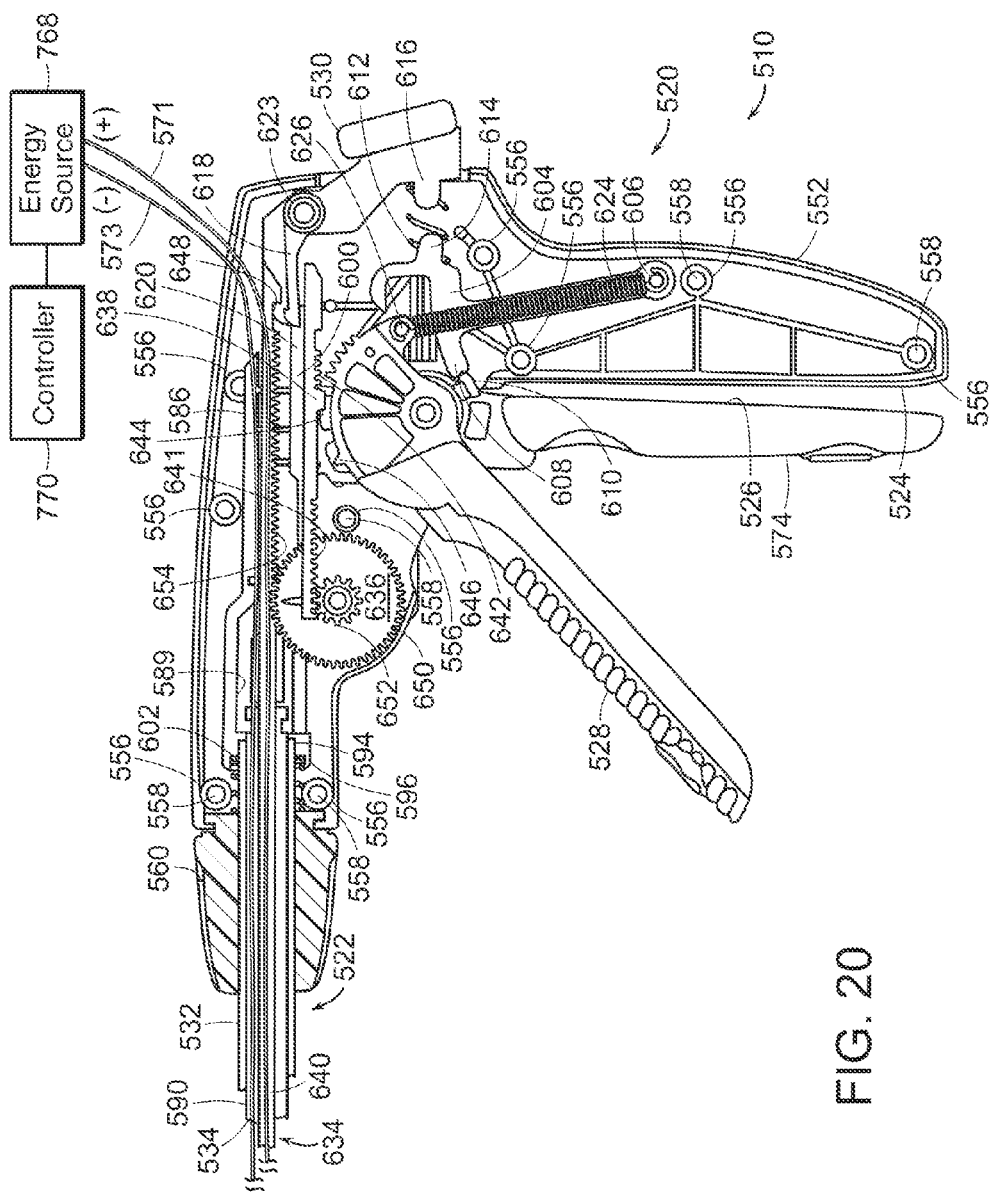
FIG. 20 is a cut-away side view of the handle portion of the surgical instrument of FIG. 13 with one of the triggers in the retracted position and the one of the triggers in the non-retracted position in accordance with one non-limiting embodiment of the present disclosure.

In one embodiment, as the yoke 586 moves distally in response to proximal movement of the closure trigger 526, an upper latch arm 618 of the release button 530 can move along an upper surface 620 on the yoke 586 until dropping into an upwardly presented recess 622 in a proximal, lower portion of the yoke 586. The release spring 612 can urge the release button 530 outward, which can pivot the upper latch arm 618 downwardly into engagement with the upwardly presented recess 622, thereby locking the closure trigger 556 in a tissue clamping position, such as illustrated in FIG. 20, for example.

In various embodiments, the latch arm 618 can be moved out of the recess 622 to release the first jaw 518 by pushing the release button 530 inward. Specifically, the upper latch arm 618 can pivot upward about a pin 623 of the second base section 552. The yoke 586 can then be permitted to move proximally in response to return movement of the closure trigger 526.

In one embodiment, a firing trigger return spring 624 can be located within the handle portion 520 with one end attached to the pin 606 of the second base section 552 and the other end attached to a pin 626 on the firing trigger 528. The firing return spring 624 can apply a return force to the pin 626 for biasing the firing trigger 528 in a direction away from the pistol grip 524 of the handle portion 520. The closure trigger 526 can also be biased away from pistol grip 524 by the engaging surface 628 of the firing trigger 528 biasing the front surface 630 of the closure trigger 526.

In various embodiments, as the closure trigger 526 is moved toward the pistol grip 524, its front surface 630 can be engaged with the engaging surface 628 on the firing trigger 528 causing the firing trigger 528 to move to its "firing" position. When in its firing position, the firing trigger 528 can be located at an angle of approximately 45 degrees, for example, to the pistol grip 524. After staple firing, the spring 624 can cause the firing trigger 528 to return to its initial unfired position. During the return movement of the firing trigger 528, its engaging surface 628 can push against the front surface 630 of the closure trigger 526 causing the closure trigger 526 to return to its initial position. A stop member 632 can extend from the second base section 552 to prevent the closure trigger 526 from rotating beyond its initial position.

In various embodiments, the surgical stapling, sealing, and/or severing instrument 510 additionally can comprise a reciprocating section 634, a multiplier 636, and a drive member 638. The reciprocating section 634 can comprise a wedge sled in the implement portion 522 (not illustrated in FIGS. 18-21) and a metal drive rod 640.

In one embodiment, the drive member 638 can comprise first and second gear racks 641 and 642. A first notch 644 can be provided on the drive member 638 intermediate the first and second gear racks 641 and 642. During return movement of the firing trigger 528, a tooth 646 on the firing trigger 528 can be engaged with the first notch 644 for returning the drive member 638 to its initial position after staple firing. A second notch 648 can be located at a proximal end of the metal drive rod 640 for locking the metal drive rod 640 to the upper latch arm 618 of the release button 530 in its unfired position.

In various embodiments, the multiplier 636 can comprise first and second integral pinion gears 650 and 652. The first integral pinion gear 650 can be engaged with a first gear rack 654 provided on the metal drive rod 640 and the second integral pinion gear 652 can be engaged with the first gear rack 641 on the drive member 638. The first integral pinion gear 650 can have a first diameter and the second integral pinion gear 652 can have a second diameter that is smaller than the first diameter.

Figure 18:
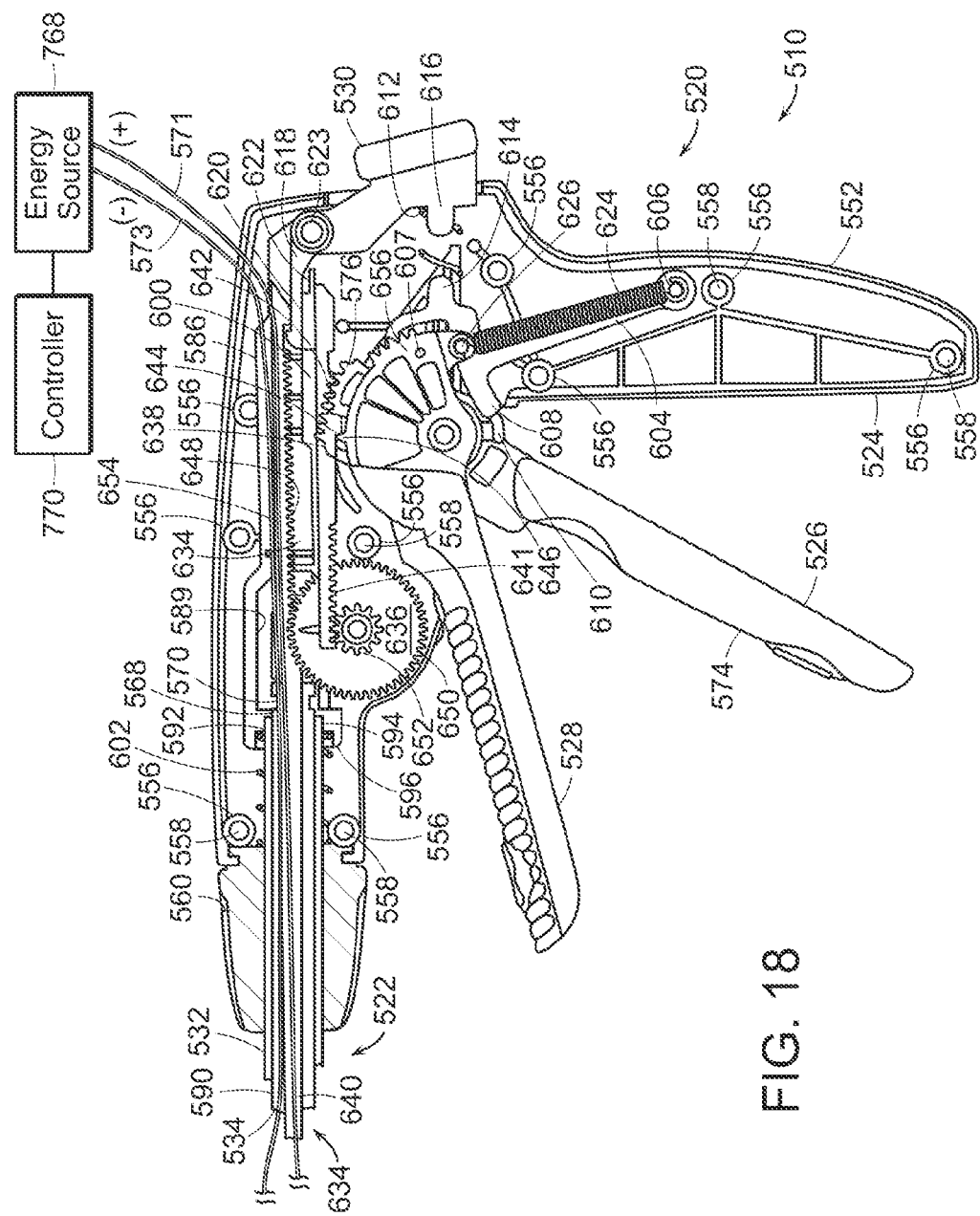
FIG. 18 is a cut-away side view of a handle portion of the surgical instrument of FIG. 13 with a base portion thereof removed and both triggers in the non-retracted position in accordance with one non-limiting embodiment of the present disclosure.
Figure 19:
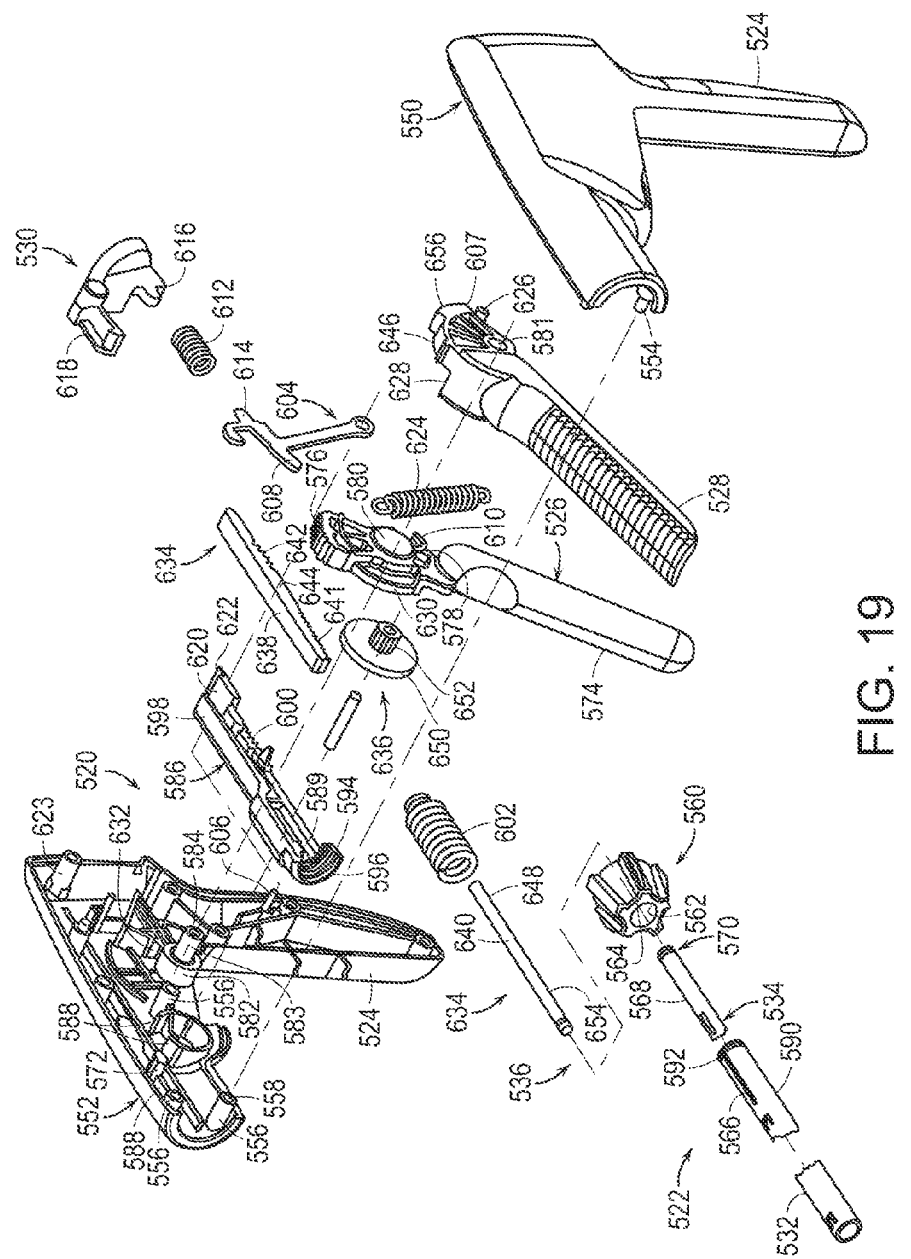
FIG. 19 is an exploded perspective view of the handle portion of the surgical instrument of FIG. 13 in accordance with one non-limiting embodiment of the present disclosure.
Figure 21:
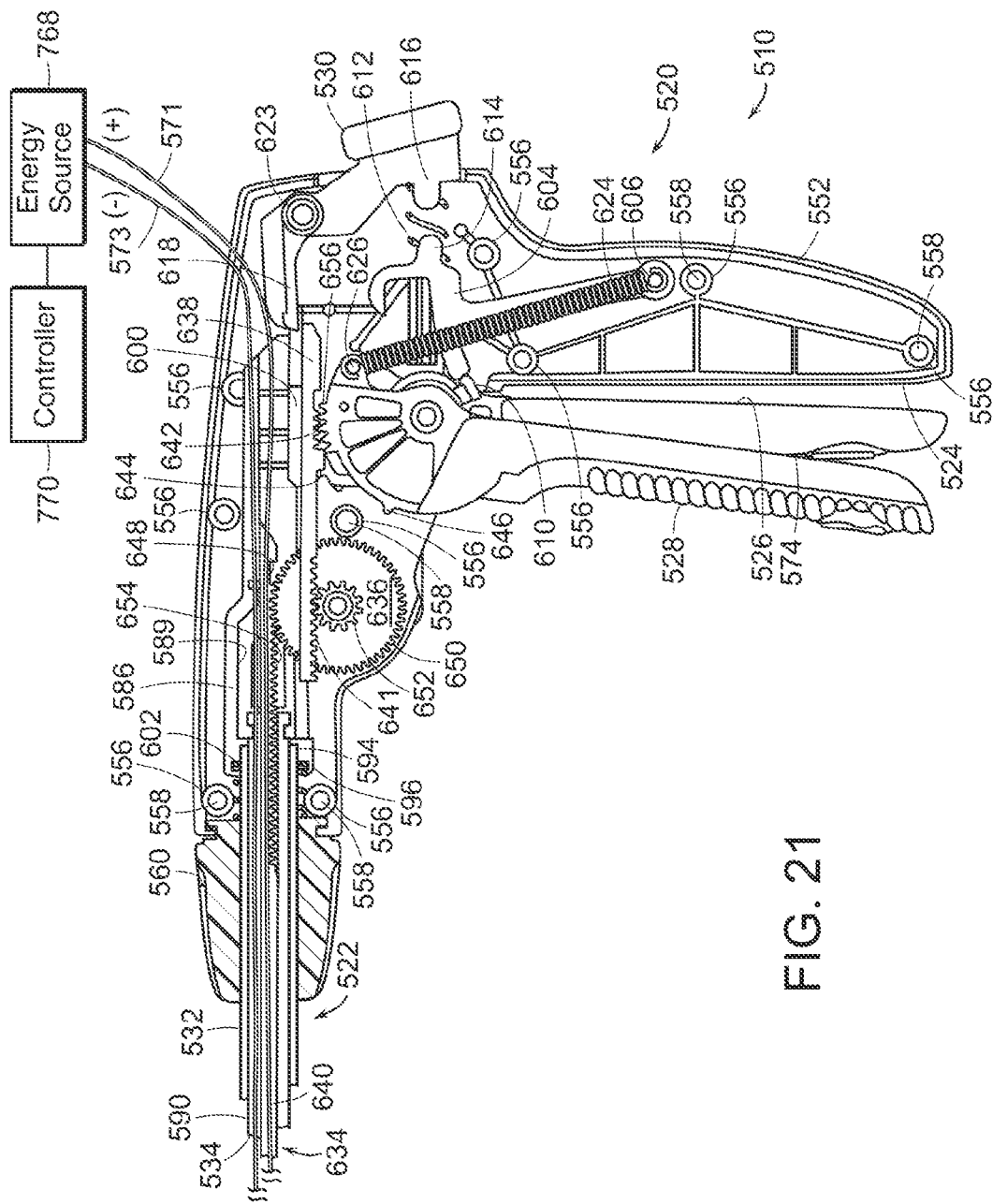
FIG. 21 is a cut-away side view of the handle portion of the surgical instrument of FIG. 13 with both of triggers in the retracted position in accordance with one non-limiting embodiment of the present disclosure.

In various embodiments, FIGS. 18, 20, and 21 illustrate, respectively, the handle portion 520 in the start position (open and unfired), a clamped position (closed and unfired), and a fired position. The firing trigger 528 can be provided with a gear segment section 656. The gear segment section 656 can be engaged with the second gear rack 642 on the drive member 638 such that motion of the firing trigger 528 can cause the drive member 638 to move back and forth between a first drive position, illustrated in FIG. 20, and a second drive position, illustrated in FIG. 21. In order to prevent staple firing before tissue clamping has occurred, the upper latch arm 618 on the release button 530 can be engaged with the second notch 648 on the drive member 638 such that the metal drive rod 640 can be locked in its proximal-most position, as illustrated in FIG. 18. When the upper latch arm 618 falls into the recess 622, the upper latch arm 618 can disengage with the second notch 648 to permit distal movement of the metal drive rod 640, as illustrated in FIG. 20.

Because the first gear rack 641 on the drive member 638 and the gear rack 654 on the metal drive rod 640 are engaged with the multiplier 636, movement of the firing trigger 528 can cause the metal drive rod 640 to reciprocate between a first reciprocating position, illustrated in FIG. 20, and a second reciprocating position, illustrated in FIG. 21. Since the diameter of the first pinion gear 650 is greater than the diameter of the second pinion gear 652, the multiplier 636 can move the reciprocating section 634 a greater distance than the drive member 638 is moved by the firing trigger 528. In various embodiments, the diameters of the first and second pinion gears 650 and 652 can be changed to permit the length of the stroke of the firing trigger 528 and the force required to move it to be varied.

It will be appreciated that the handle portion 520 is illustrative and that other actuation mechanisms may be employed. For instance, the closing and firing motions may be generated by automated means and/or can be generated by retracting a single trigger that can accomplish both closing and firing motions, for example.

In various embodiments, referring to FIGS. 22-28, the end-effector assembly 512 of the surgical instrument 510 is illustrated in further detail. As described above, the handle portion 520 can produce separate and distinct closing and firing motions that actuate the end-effector assembly 512. The end-effector assembly 512 can maintain the clinical flexibility of this separate and distinct closing and firing (i.e., stapling and severing). In addition, the end-effector assembly 512 can introduce the aforementioned ability to affirmatively maintain the closed spacing during firing after the surgeon positions and clamps the tissue within the end-effector assembly 512. Both features procedurally and structurally enhance the ability of the surgical instrument 510 by ensuring adequate spacing for instances where an otherwise inadequate amount of tissue is clamped by the end-effector assembly 512 and to enhance the clamping in instances where an otherwise excessive amount of tissue has been clamped by the end-effector assembly 512.

Figure 22:
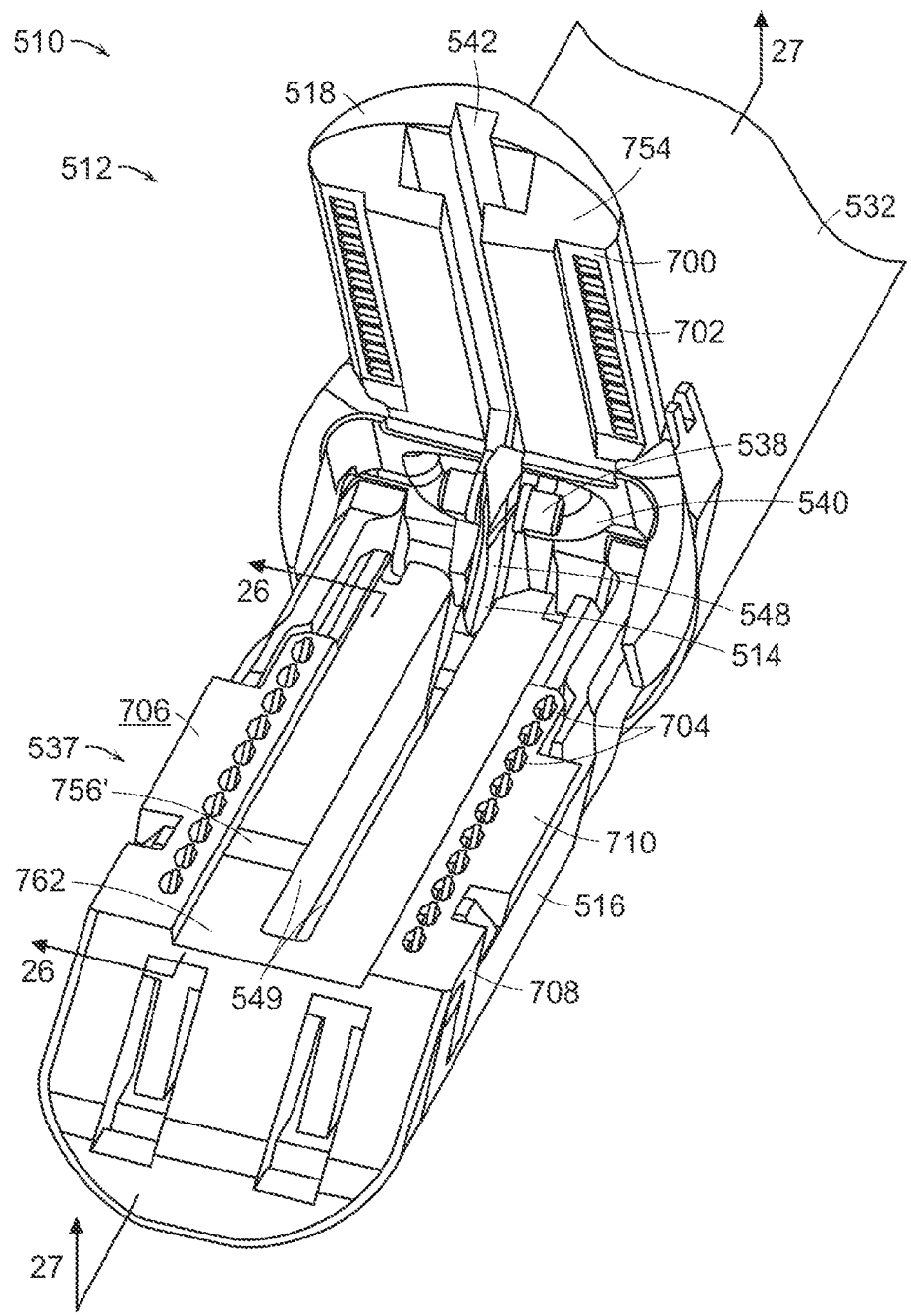
FIG. 22 is a perspective view of the end-effector assembly of the surgical instrument of FIG. 13 in an open configuration in accordance with one non-limiting embodiment of the present disclosure.

In one embodiment, FIG. 22 illustrates the end-effector assembly 512, which is in an open position by the retracted closure sleeve 532, with the staple cartridge 537 installed in the second jaw 516. On a lower surface 700 of the first jaw 518, one or more rows of stapling forming pockets 702 can be arrayed to correspond to one or more rows of staple cavities 704 in an upper surface 706 of the staple cartridge 537. The firing bar 514 is at its proximal position, with the upper pin 538 aligned in a noninterfering fashion with the anvil pocket 540. The anvil pocket 540 is illustrated as communicating with the longitudinal anvil slot 542 in the first jaw 518. The distally presented cutting member 548 of the firing bar 514 can be aligned with and proximally from removed from the vertical slot 549 in the staple cartridge 537, thereby allowing removal of a spent cartridge and insertion of an unfired cartridge, which can be snap-fit or otherwise fit into the second jaw 516. Specifically, extension features 708 and 710 of the staple cartridge 537 can engage recesses 712, 714 (illustrated in FIG. 24) of the second jaw 516.

Figure 23:
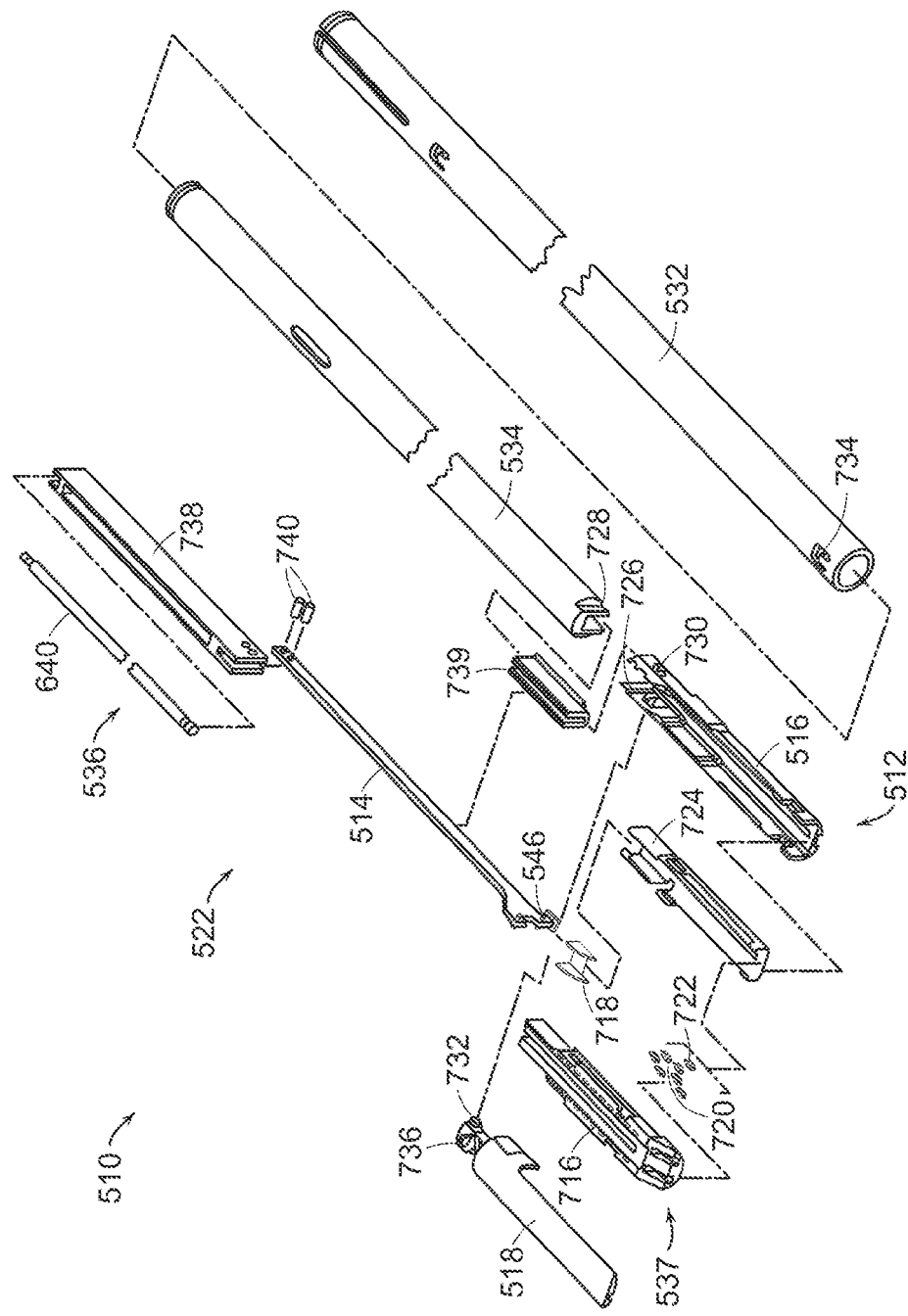
FIG. 23 is an exploded perspective view of a shaft and an end-effector assembly of the surgical instrument of FIG. 13 in accordance with one non-limiting embodiment of the present disclosure.

In one embodiment, FIG. 23 illustrates the implement portion 522 and the end-effector assembly 512 of the surgical instrument 510 in disassembled form. The end-effector assembly 512 can comprises the staple cartridge 537 illustrated as being comprised of a cartridge body 716, a wedge sled 718, drivers 720, staples 722, and a cartridge tray 724. When assembled, the cartridge tray 724 can hold the wedge sled 718, the drivers 720, and the staples 722 inside the cartridge body 716. Drivers 720 can be used when one staple line is being deployed from a side of the staple cartridge 537 and double drivers can be used with two staple lines are being deployed from a side of the staple cartridge 537. Of course, if three staple lines are being deployed from each side of the staple cartridge 537, three drivers can be provided and so forth. The drivers 720 and the wedge sled 718 together can be referred to herein as driver 718 and/or an electrically-conductive driver 718, since they both function to drive staples into tissue positioned within the end-effector assembly 512.

Having a wedge sled 718 integral to the staple cartridge 537 can enable a number of flexible design options as compared to incorporating camming surfaces onto a firing bar itself. For instance, a number of different staple cartridges may be selected for use in the surgical instrument 510 with each staple cartridge having a different configuration of one or more rows of staples, each thus having a unique wedge sled configured to contact the middle pin 546 of the firing bar 514 while causing the driving of the staples 722.

In one embodiment, the second jaw 516 can have a proximally placed attachment cavity 726 that can receive a channel anchoring member 728 on the distal end of the frame 534 for attaching the end-effector assembly 512 to the handle portion 520. The second jaw 516 can also have an anvil cam slot 730 that can pivotally receive an anvil pivot 732 of the first jaw 518. The closure sleeve 532 that encompasses the frame 534 can comprise a distally presented tab 734 that can engage an anvil feature 736 proximately on the first jaw 518 but distal to the anvil pivot 732 to thereby effect opening and closing of the first jaw 518. The firing drive member 536 is illustrated as being assembled to the firing bar 514 attached to a firing connector 738 by pins 740, which in turn is rotatingly and proximally attached to the metal drive rod 640. The firing bar 514 can be guided at a distal end of the frame by a slotted guide 739 inserted therein, for example.

Figure 24:
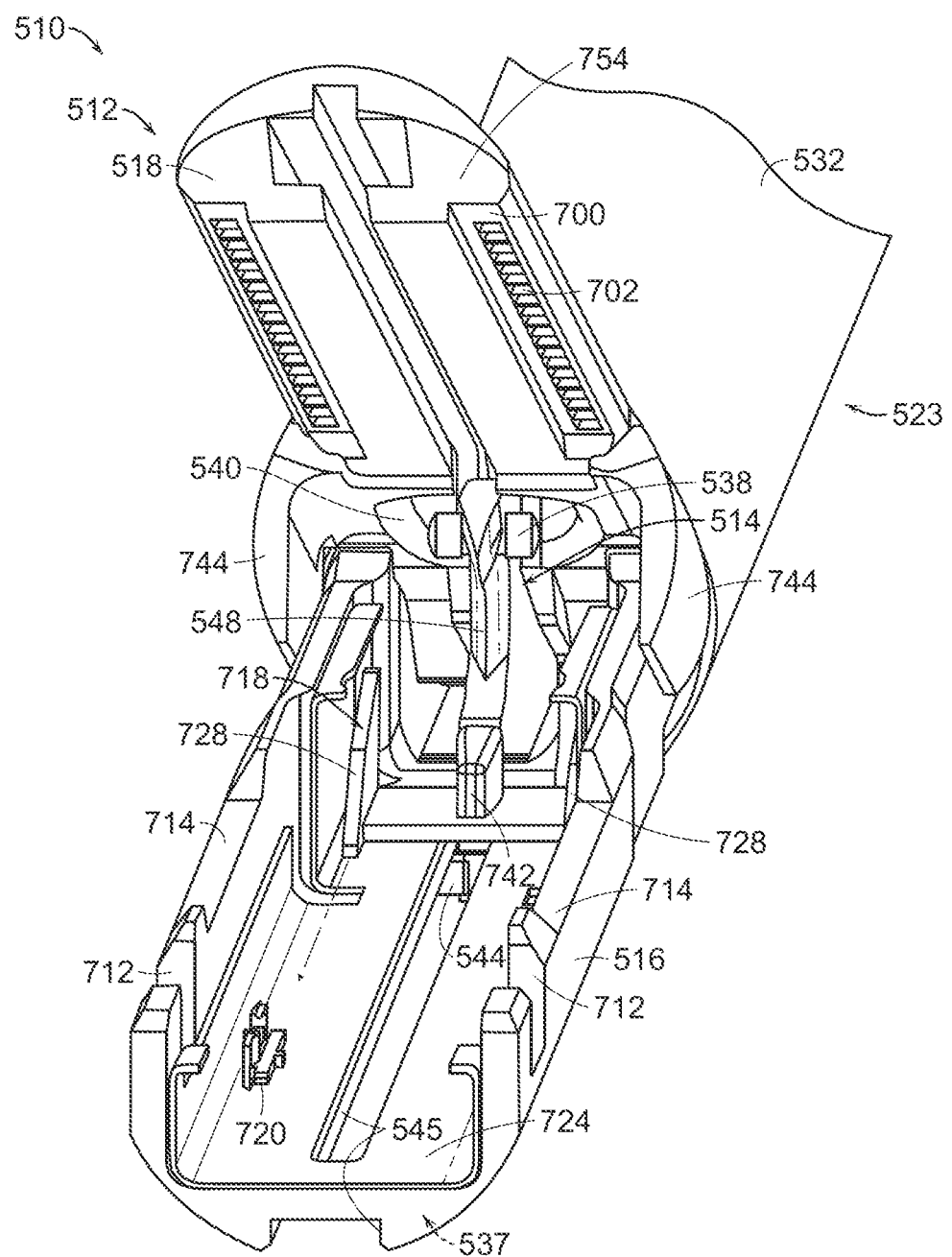
FIG. 24 is a perspective view of the end-effector assembly of the surgical instrument of FIG. 13 with a staple cartridge partially removed in accordance with one non-limiting embodiment of the present disclosure.

In various embodiments, with particular reference to FIG. 24, a portion of the staple cartridge 537 is removed to expose portions of the second jaw 516, such as the recesses 712 and 714 and to expose some components of the staple cartridge 737 in their unfired position. In particular, the cartridge body 716 (illustrated in FIG. 23) has been removed. The wedge sled 718 is shown at its proximal, unfired position with a pusher block 742 contacting the middle pin 546 (not illustrated in FIG. 24) of the firing bar 514. The wedge sled 718 can be in longitudinal sliding contact upon the cartridge tray 724 and can comprise wedges 728 that force upward the drivers 720 as the wedge sled 718 moves distally. Staples 722 (not illustrated in FIG. 24) resting upon the drivers 720 can thus also be forced upward into contact with the staple forming pockets 702 on the first jaw 518 to form closed staples. Also illustrated is the channel slot 545 in the second jaw 516 that can be aligned with the vertical slot 549 in the staple cartridge 537.

Figure 25:
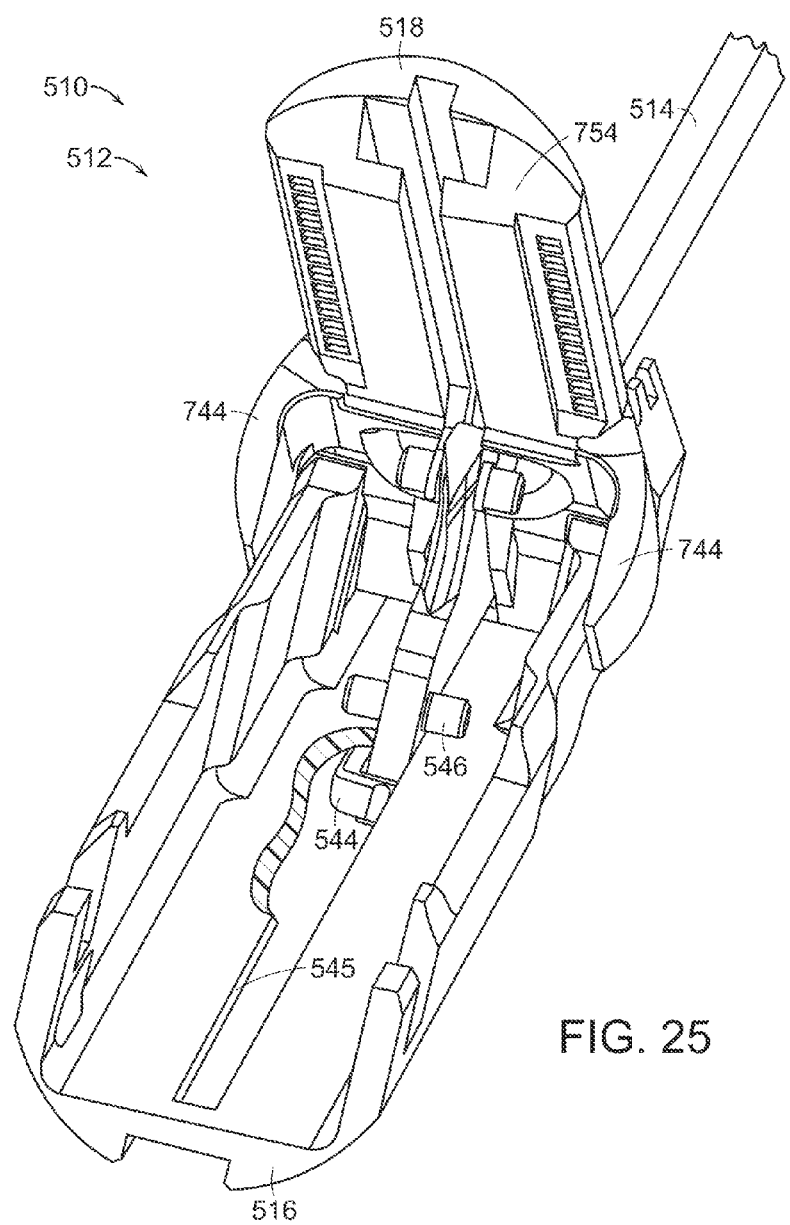
FIG. 25 is a perspective view of the end-effector assembly of the surgical instrument of FIG. 24 with the staple cartridge fully removed in accordance with one non-limiting embodiment of the present disclosure.

In one embodiment, FIG. 25 illustrates the end-effector assembly 512 of FIG. 24 with all of the staple cartridge 537 removed to show the middle pin 546 of the firing bar 514 as well as portion of the second jaw 516 removed adjacent to the channel slot 545 to expose the firing bar cap 544. In addition, the shaft 523 is removed to expose a proximal portion of the firing bar 514. Projecting downward from the first jaw 518 near the pivot, a pair of opposing tissue stops 744 can prevent, or at least inhibit, tissue from being positioned too far up into the end-effector assembly 512 during clamping.

Figure 26:
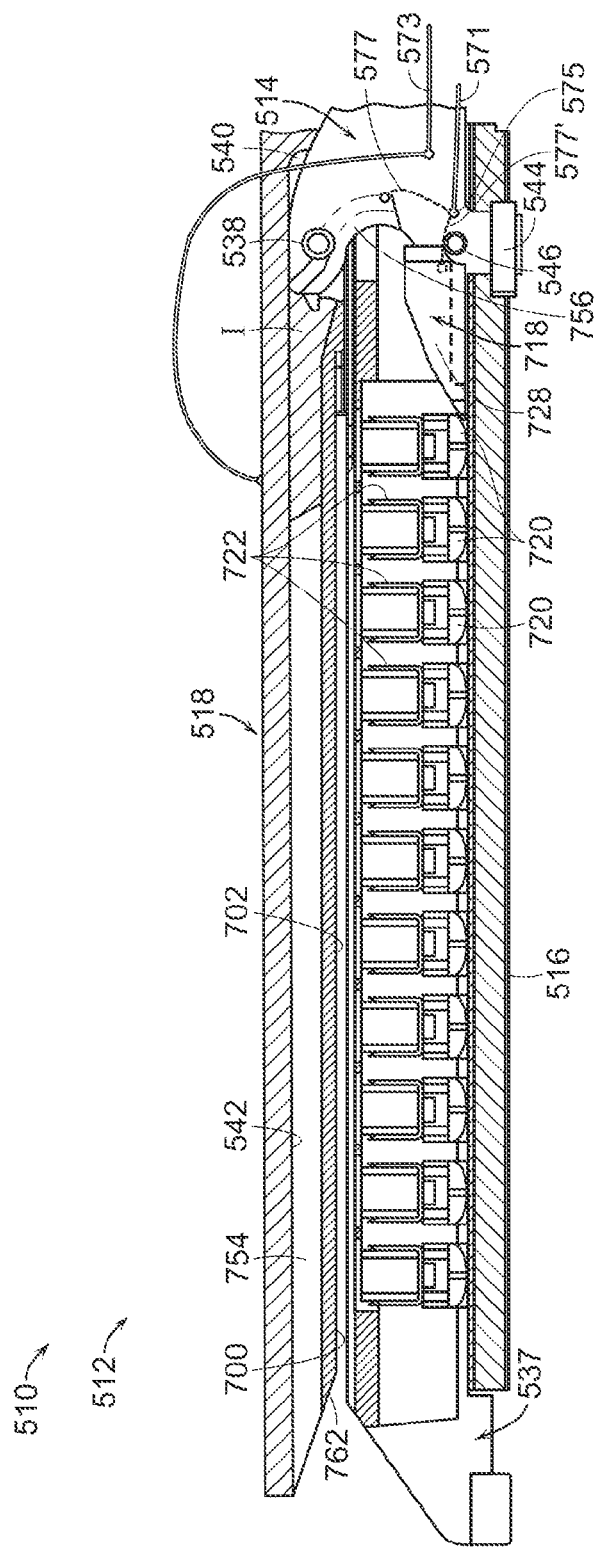
FIG. 26 is sectional view of the end-effector assembly of FIG. 22 taken along line 26-26 with a cutting member and a driver in a retracted position in accordance with one non-limiting embodiment of the present disclosure.

In various embodiments, FIG. 26 illustrates the end-effector assembly 512 closed in a tissue clamping position with the firing bar 514 unfired. The upper pin 538 can be in the anvil pocket 540, vertically aligned with the anvil slot 542 for distal longitudinal movement of the firing bar 514 during firing. The middle pin 546 can be positioned to push the wedge sled 718 distally so that wedge 728 can sequentially contact and lift drivers 720 and the respective staples 722 into forming contact with staple forming pockets 702 in the lower surface 700 of the first jaw 518.

In various embodiments, FIG. 27 illustrates the upper surface 706 of the staple cartridge 537 with the firing bar 514 in its unfired, proximal position. The one or more staple cavities 704 can be arrayed on each side of the vertical slot 549 in the staple cartridge 537.

In one embodiment, FIG. 28 illustrates the end-effector assembly 512 near the pivot showing that the second jaw 516 has opposing ramp portions 746 to thereby cooperate with the tissue stops 744 of the first jaw 518 (not illustrated in FIG. 28) to prevent tissue from jamming the end-effector assembly 512. Also illustrated in greater detail are the drivers 720 and their relation to the staples 722.

The features of the surgical instrument 510 which enable sealing of tissue disposed and/or clamped within the end-effector assembly 512 will now be described. It will be understood by those of skill in the art that surgical instruments, other than the surgical instrument 510, can be configured or produced to comprise such sealing features. The present disclosure is not limited to the use of such features with the surgical instrument 510 and can be used with other surgical instruments.

In one embodiment, referring generally to FIGS. 13-15, 17, 18, 20-22, and 24-35, the surgical instrument 510, can be electrically coupled to an energy source 768 in communication with a controller 770. In various embodiments, the energy source 768 can provide energy to the surgical instrument 510 and at least to one electrode of the end-effector assembly 512, wherein the magnitude, duration, wave form, and/or frequency, for example, of the energy can be sufficiently controlled or modulated, by the controller 770, for example, to provide a desired amount or type of energy to the surgical instrument 510. The energy source 768 and the energy provided to the surgical instrument 510 can be the same as or similar to that described herein. Further, the controller 770 can be the same as or similar to that described herein. The energy source 768 can be in electrical communication with the surgical instrument 510 through first and second conductors 571 and 573 or through other suitable methods. The first and second conductors 571 and 573 can extend from the energy source 768 to or proximate to the end-effector assembly 512 or to other portions of the surgical instrument 510.

In one embodiment, the first conductor 571 can extend proximate to a portion of the firing bar 514 when the firing bar 514 is in the retracted position (see e.g., FIG. 14). In various embodiments, the first conductor 571, which can act as the supply or positive conductor, can be engaged with a contact 575 positioned adjacent to the firing bar 514. The contact 575 or other conductive element in communication with the contact 575 can be biased or spring-biased towards the firing bar 514 such that energy can be provided to a conductive track 525 in the firing bar 514, to the firing bar 514 itself, and/or to a conductive portion of the firing bar 514, for example. By providing such a contact 575 and conductive track 525 or conductive portion of the firing bar 514, energy can be supplied by the first conductor 571 to a distal portion of the firing bar 514 even when the firing bar 514 is moved distally within the end-effector assembly 512 into its extended position (see e.g., FIG. 17). In one embodiment, the energized portion of the firing bar 514, such as the conductive track 525, for example, can be surrounded by an insulative material or a non-conductive material (indicated as "I" in the figures) such that only the conductive track 525 is energized, instead of the entire firing bar 514. In other various embodiments, the entire firing bar 514 can be energized and can be surrounded by an insulative material or a non-conductive material in the appropriate places, such that energy can be directed within the end-effector assembly 512 as necessary.

Various conductors 577, 577', 577", and/or other conductors can extend from the contact 575 or from portions of the conductive track 525 to energize various portions of the end-effector assembly 512 or the staple cartridge 537. The conductor 577, if provided, can extend from the contact 575 or the conductive track 525 to the cutting member 548 to supply energy to the cutting member 548. The conductor 577', if provided, can extend from the contact 575 or the conductive track 525 to the driver 718, such as an electrically-conductive staple driver, for example, to supply energy to the staples 722 when contacted by the driver 718. The conductor 577", if provided, can extend from the contact 575 or the conductive track 525 to an electrode on or in one of the first jaw 518 and the second jaw 516 (or on or in a staple cartridge of the second jaw 516) to supply energy to the electrode. In other various embodiments, the contact 575 or the first conductor 571 can be in electrical communication with an electrode on the first jaw 518 and/or the second jaw 516, for example, and may not be in contact with the firing bar 514. In any event, energy can be supplied to the end-effector assembly 512 such that tissue can be sealed by the end-effector assembly 512.

In various embodiments, the second conductor 573, which can act as the return or negative conductor, can extend from the energy source 768 to a portion of the end-effector assembly 512, such as the first jaw 518, for example. In one embodiment, the second conductor 573 can be in electrical communication with a contact on the first jaw 518 or can be directly attached to the first jaw 518 at a conductive section of the first jaw 518. The second conductor 573 can channel energy from the end-effector assembly 512 back to the energy source 768 and/or the controller 770, for example. Although the first conductor 571 is described as being the supply or positive conductor and the second conductor 573 is described as being the return or negative conductor, in various embodiments, the first conductor 571 can be the return or negative conductor and the second conductor 573 can be the supply or positive conductor, for example.

In one embodiment, at least one of the first and second conductors 571 and 573, such as the first conductor 571, can comprise a switch 579, optionally engaged with an activation button 764 on the surgical instrument 510. The switch 579 can act as a typical switch and can disrupt the flow of energy through the surgical instrument 510 and/or through the end-effector assembly 512 of the surgical instrument 510 when in an open position. In one embodiment, the switch 579 can be in a normally-open position and the activation button 764, when depressed, can be used to close the switch 579 to complete the circuit between the energy source 768 and the surgical instrument 510. In other embodiments, full retraction of the closure trigger 526 or the firing trigger 528 can close the switch 579 or another suitable switch and allow energy to flow to the surgical instrument 510. In any event, the switch 579 can be configured to remain closed until a predetermined time has lapsed such that energy can flow through portions of the end-effector assembly 512 and through the tissue to cause a suitable seal to be formed in the tissue. In one embodiment, the switch 579 can remain closed for a predetermined period of time although the activation button 764 is released or although the firing trigger 528 is released and allowed to retract into its unfired state.

In various embodiments, portions of the end-effector assembly 512 and/or portions of the surgical instrument 510 can comprise insulative materials or non-conductive materials, such as plastic or rubber, for example. Such insulative materials or non-conductive materials can aid in confining the energy within the end-effector assembly 512 within the conductive portions. For instance, an insulative material can be provided on the proximal portion of the first jaw 518 such that energy can be returned from the first jaw 518 though the second conductor 573 without coming into electrical contact with the firing bar 514, for example.

In one embodiment, the staples 722 positioned with the staple cavity 704 of the second jaw 516 can comprise the first electrode. Although referred to as the "first electrode", those of ordinary skill in the art will recognize that each staple 722 or less than all of the staples 722 can comprise a first electrode (i.e., only some staples make comprise conductive portions). In various embodiments, the staples 722 can comprise conductive portions or can be comprised of conductive materials, such as metals, for example. To allow energy to flow to the staples 722, the first conductor 571 can supply energy to the contact 575. The contact 575 can then supply energy to the firing bar 514, the conductive track 525, and/or to the electrically conductive driver 718 optionally using the conductor 577'. In one embodiment, the staples 722 can supply energy to the tissue when they are in contact with the electrically-conductive driver 718. In one embodiment, the staples 722 can be removably positioned within staple cavities 704 in the second jaw 518 or the staple cartridge 537. In various embodiments, the electrically-conductive driver 718 can be configured to move each of the staples 722 between a first stored position in which the staple 722 is at least partially positioned within the staple cavity 704 and a second position in which the staples 722 are at least partially deployed from the staple cavity 704 into tissue positioned intermediate the first jaw 518 and the second jaw 516. In one embodiment, more than one staple 722 can be in electrical communication with the electrically-conductive driver 718 at one time or more than one electrically-conductive driver can be in communication with the staples 722 at one time. By supplying energy to the staples 722, the tissue can be sealed in the area in which staple legs of the staples 722 puncture the tissue. Such sealing about a perimeter of the staple legs can decrease bleeding caused by the puncturing of the tissue by the staple legs. In various embodiments, the staples 722 and/or the electrically-conductive driver 718 can comprise a fuse, such as the PTC material described above, for example, to regulate the energy flow of the energy from the staples 722 to another electrode within the end-effector 512.

In one embodiment, the end-effector assembly 512 and/or the staple cartridge 537 can comprise a second electrode on one of the first jaw 518 or the second jaw 516. The second electrode can have the same polarity or a different polarity than the first electrode. In various embodiments, a second electrode 754 can be positioned on or form a portion of the first jaw 518 and can be in electrical communication with the second conductor 573. In such an embodiment, the second electrode 754 can receive the energy supplied by the first electrode after such energy passes through and seals the tissue. In this configuration, portions of a tissue-contacting surface of the second jaw 516 and/or the staple cartridge 537 can be comprised of an insulative material such that energy flows from the first electrode (e.g., portions of the staples 722) toward the second electrode 754 on the first jaw 518. The first jaw 518 can comprise a fuse 762, such as the PTC material described above, to regulate or inhibit the energy flow between the first electrode and the second electrode 754. The fuse 762 can be positioned around or in the pockets of the first jaw 518 and the second electrode 754 can be positioned underneath the fuse 762, for example. In such an embodiment, a tissue-contacting surface of the first jaw 518 can comprise an insulative material such that energy can pass from the first electrode, through the fuse 762, to the second electrode 754, and then to the second conductor 573.

In one embodiment, the end-effector assembly 512 can comprise a third electrode. In various embodiments, a third electrode 756 can be positioned on or form the cutting member 548. In other various embodiments, the third electrode 756' can be positioned on or form a portion of the second jaw 516. In various embodiments, the third electrode 756 or 756' can have the same polarity or a different polarity than the first electrode and/or the second electrode 754, for example. In one embodiment, the third electrodes 756 and 756' can both be provided on an end-effector assembly of a surgical instrument. In various configurations, energy can flow from the third electrode 756 or 756', through the tissue, toward the first electrode and/or the second electrode 754, for example. By providing the third electrode 756 on the cutting member 548, tissue can be sealed as it is cut by the cutting member 548 thereby reducing bleeding at the cutting site. In one example embodiment, energy can travel from the first electrode (i.e., staples 722) and the cutting member (i.e., third electrode 756), through the tissue, and possibly through a fuse, to the second electrode 754 on the first jaw 518. The fuse 762 can be positioned adjacent to the second electrode 754 on the first jaw 518. In such an embodiment, the first electrode and the third electrode 756 can have the same polarity (e.g., positive) while the second electrode 754 can have a different polarity (e.g., negative). Other polarity configurations of the various electrodes are also within the scope of the present disclosure. In various embodiments, the various electrodes can be positioned within the end-effector assembly 512 in a fashion such that the flow of energy through the tissue and the end-effector assembly 512 can be controlled to control the thermal spread caused by the energy flow. As discussed herein, heat can be generated in the tissue by the resistance to energy flow that the tissue creates between the various electrodes.

In an embodiment, where the third electrode 756' is positioned on the second jaw 516, the third electrode 756' can act as a supply or a return electrode. In one embodiment, the third electrode 756' can be positioned on or in the staple cartridge 537 positioned within the second jaw 516, for example. In other various embodiments, the third electrode 756' can be positioned adjacent to a fuse, such as fuse 762, for example. The fuse 762 can be similar to the fuse 62 discussed herein and can be positioned more proximal to a tissue-contacting surface of the second jaw 516 than the third electrode 756', such that energy can passes through the fuse 762 before reaching the third electrode 756' or can pass through the fuse 762 after leaving the third electrode 756'. As discussed herein with respect to the fuse 62, the fuse 762 can be used to limit, restrict, and/or stop the energy flow from one electrode to another.

In one embodiment, temperature measuring devices or sensors, such as thermocouples, RTD's (resistive thermal devices), thermistors, and other suitable devices can be embedded at strategic locations within the end-effector assembly 512 to sense the temperature of the tissue positioned within the end-effector assembly 512. As a result, the delivery of energy to at least one of the electrodes can be controlled in response to feedback from these devices, for example.

In various embodiments, by using more than two electrodes (e.g., three or four), the thermal spread of heat within the tissue compressed between the first jaw 518 and the second jaw 516 can be minimalized thereby reducing heating of the tissue adjacent to the end-effector assembly 512. Such minimalization can occur owing to a controlled path of the energy through the various electrodes.

In various embodiments, in order to direct the energy flow through the end-effector assembly 512 through the various electrodes and the tissue properly, certain portions of the end-effector assembly 512 can comprise insulative materials or non-conductive portions. In one embodiment, portions of the tissue-contacting surfaces of the first jaw 518 and the second jaw 516 can comprise insulative materials or non-conductive portions to cause energy to flow from at least one electrode, through the fuse 762 or another fuse, to at least one other electrode. In other embodiments, portions of the first jaw 518 and the second jaw 516 adjacent to the electrodes can comprise insulative materials or non-conductive portions to maintain the energy flow between the various electrodes and at least inhibit energy from flowing to other portions of the end-effector assembly 512. Those of skill in the art will understand how and where, in various embodiments, the various insulative materials or non-conductive portions can be placed within the end-effector assembly 512.

Figure 36:
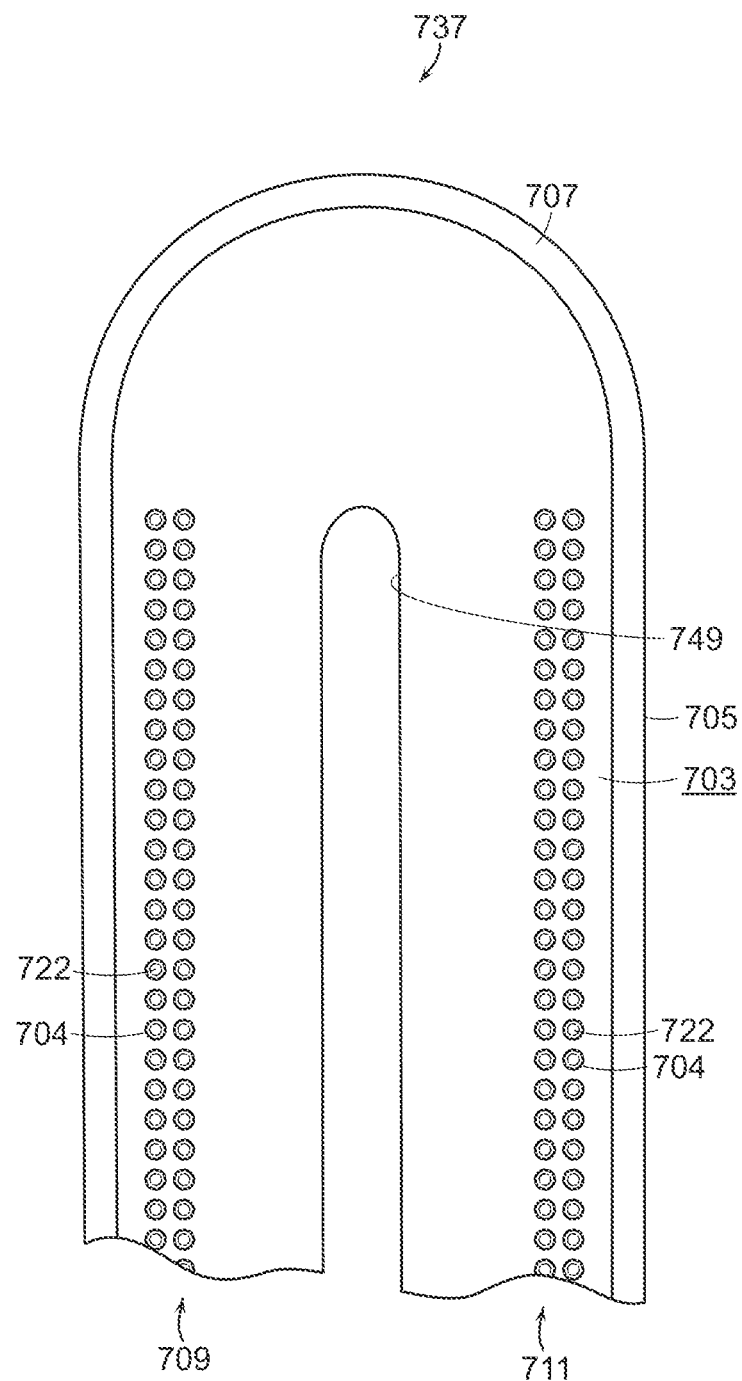
FIG. 36 is a schematic illustration of a second jaw of an end-effector assembly in accordance with one non-limiting embodiment of the present disclosure.
Figure 37:
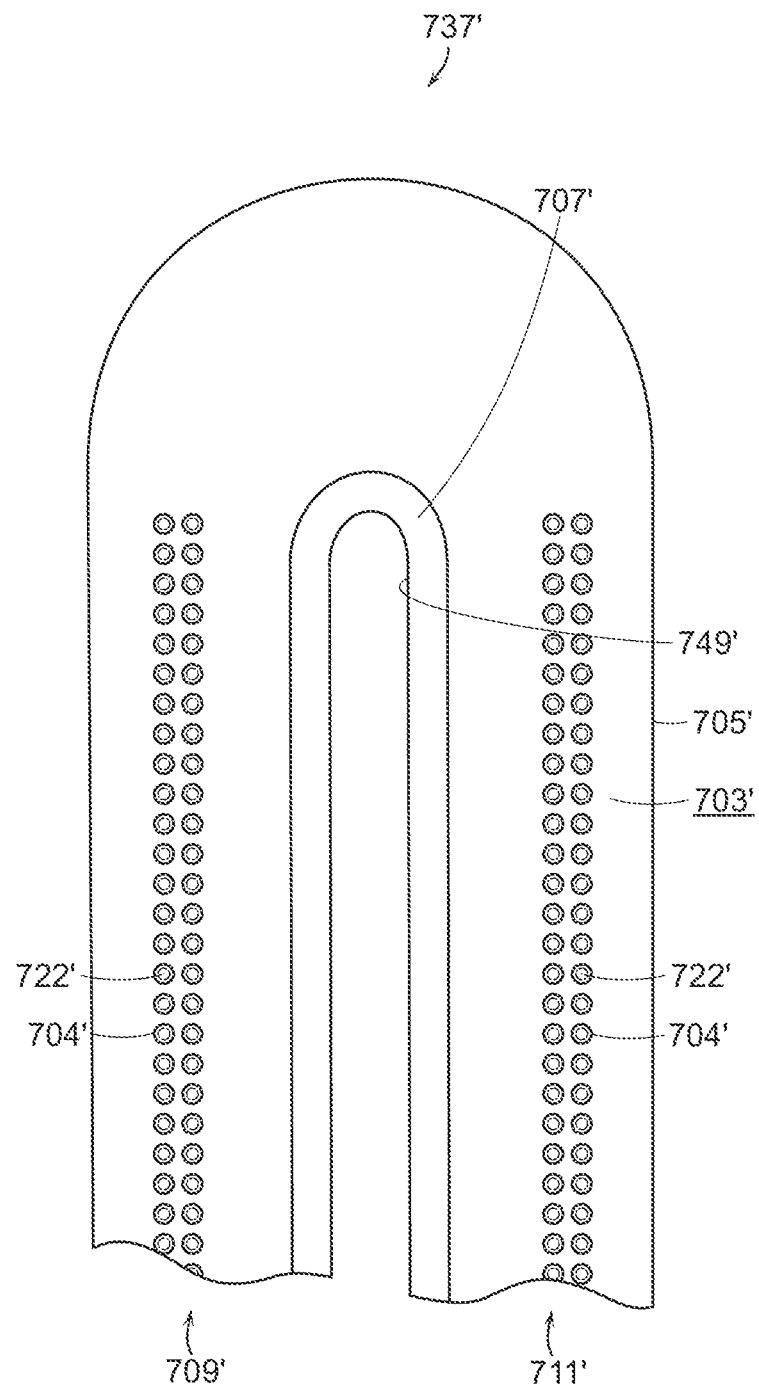
FIG. 37 is a schematic illustration of another second jaw of an end-effector assembly in accordance with one non-limiting embodiment of the present disclosure.
Figure 38:
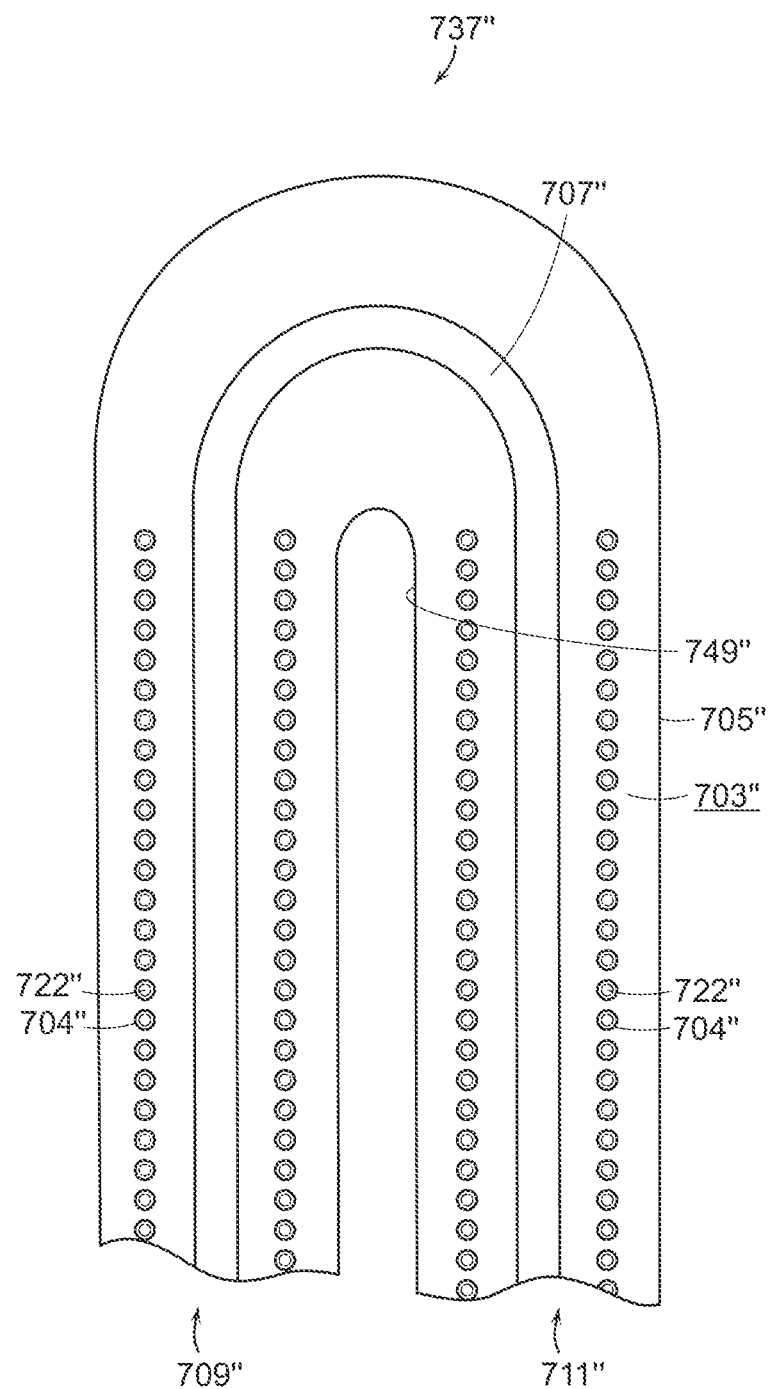
FIG. 38 is a schematic illustration of still another second jaw of an end-effector assembly in accordance with one non-limiting embodiment of the present disclosure.

In one embodiment, referring to FIGS. 36-38, a staple cartridge 737 is illustrated. The staple cartridge can be configured to be positioned on or within the second jaw 518 and can comprise a plurality of staple cavities 704, a plurality of staples 722, and a tissue-contacting surface 703 comprising an outer perimeter 705. The tissue-contacting surface 703 can comprise an electrode 707, such as a third electrode, for example. The staple cartridge 737 can also comprise a first side 709, a second side 711, and a cutting member slot 749 defined at least partially intermediate the first side 709 and the second side 711. A first plurality of staples 722 can be at least partially positioned within a first plurality of staple cavities 704 in the first side 709. The first plurality of staples 722 can form at least one row of staples 722. A second plurality of staples 722 can be at least partially positioned within a second plurality of staple cavities 704 in the second side 711. The second plurality of staples 722 can form at least a second row of staples 722. In various embodiments, FIGS. 37 and 38 illustrate the staple cartridge 737' and the staple cartridge 737", respectively. Like numbers between FIG. 36 and FIGS. 37 and 38 designate like components.

In one embodiment, referring to FIG. 36, the electrode 707 can be positioned proximate to the outer perimeter 705 of the staple cartridge 737, while the one or more rows of staples 722 can be positioned distal from the outer perimeter 705 or closer to the cutting member slot 749 than the one or more rows of staples 722. In another embodiment, referring to FIG. 37, the one or more rows of staples 722' can be positioned proximate to the outer perimeter 705' of the staple cartridge 737', while the electrode 707' can be positioned distal from the outer perimeter 705' or closer to the cutting member slot 749' than the electrode 707'. In one embodiment, referring to FIG. 38, the electrode 707" can be positioned intermediate a first row of staples 722" and a second row of staples 722". In various embodiments, more than one first row of staples 722" can be provided on the first side 709" of the electrode 707" and more than one second row of staples 722" can be provided the second side 711" of the electrode 707", for example. As a result of the various embodiments described above, the staples can be applied more proximal to a cut line in tissue than the seal created by the electrode (in conjunction with another electrode) or can be applied more distal from the cut line while the seal is positioned more proximal to the cut line in the tissue. In one embodiment, it may be desirable to have the staples positioned in the tissue more distal from the cut line in the tissue than the seal, such that the tissue can be sealed proximate to the cut line to reduce bleeding at the cut line while the staples provide support to the seal and maintain it in place. In other various embodiments, the staples can be deployed directly adjacent to or within a seal created in the tissue.

In one embodiment, referring to FIG. 13, the end effector assembly 512 can comprise one or more tissue thickness sensors, such as tissue thickness sensors 780 and 781, for example, positioned on the end-effector assembly 512. The tissue thickness sensors 780 and 781 can sense the distance between a tissue-contacting surface of the first jaw 518 and a tissue-contacting surface of the second jaw 516 to determine the thickness of the tissue clamped between the first jaw 518 and the second jaw 516. In various embodiments, the sensors 780 and 781 can be any suitable sensors known in the art, such as Hall effect sensors, capacitive sensors, optical sensors, RF sensors, and/or strain gauges, for example. In one embodiment, a signal generated by the sensors 780 and 781 can be outputted to a processor, such as a microprocessor, for example. The processor can interpret the signal to determine the thickness of the tissue clamped between the first jaw 518 and the second jaw 516. Upon determining the thickness of the tissue, the processor can be used to control a solenoid that can extend a piston to engage a recess (not illustrated) in the driver 718. Such a feature can essentially lock-out the driver 718 and prevent it from moving from the proximal position (see e.g., FIG. 14) into the extended position (see e.g., FIG. 17) if the tissue thickness is below (i.e., less than) a predetermined tissue thickness threshold. Such a feature can also prevent staples 722 from being deployed into tissue that can be sufficiently sealed with energy delivered by the various electrodes. In such an embodiment, a cutting member can be moved within the end-effector assembly 512 independently from the staple driver. If the measured tissue thickness is at or above (i.e., thicker) the predetermined tissue thickness threshold, the staples 722 can be deployed into the tissue using the driver 718. In various embodiments, the tissue thickness can also be used to determine how long (e.g., in seconds) or how much energy flows (e.g., watts) between the various electrodes when activated. For thinner tissue, the duration or strength of energy flow can be less than when sealing thicker tissue, for example.

In one embodiment, referring to FIG. 17, one or more staple sensors 782 can sense when at least one staple 722 is positioned within at least one staple cavity 704 (i.e., when the staple is in or at least partially in the first, undeployed position). The one or more staple sensors 782 can also be in communication with the processor described above such that when at least one staple 722 is not sensed within at least one staple cavity 704 and the tissue thickness measured by the sensors 780 and 781 is at or above the predetermined tissue thickness threshold, a solenoid can extend a piston to engage a recess in the firing bar 514, a staple driver, and/or cutting member and restrict or prevent movement of the firing bar 514, the staple driver, and/or the cutting member between the proximal position (see e.g., FIG. 14) and the extended position (see e.g., FIG. 17). This solenoid mechanism is one example of a lockout device, although other lockout devices known to those of skill in the art are envisioned and are within the scope of the present disclosure. The movement of the firing bar 514, the staple driver, and/or the cutting member can be restricted in that the tissue clamped within the end-effector assembly 512 may be too thick to be sealed merely by the electrodes without the use of the staples 722. Once the sensor 782 senses that at least one staple 722 is present in at least one staple cavity 704, the solenoid can retract the piston from engagement with the firing bar 514, the staple driver, and/or the cutting member and the firing bar 514, the staple driver, and/or the cutting member can advance distally within the end-effector assembly 512 and staples 722 can be deployed into the tissue using the firing bar 514 or the staple driver 718. If the tissue thickness is below the predetermined tissue thickness threshold and the sensor 782 indicates that at least one staple 722 is not present in at least one staple cavity 704, the solenoid may not extend the piston to engage the recess in the firing bar 514, the staple driver, and/or the cutting member and a seal and a cut may be made in the tissue, (i.e., no staples are required). Such a feature can at least inhibit a surgeon from merely sealing tissue using the various electrodes when staples should also be deployed into the tissue to aid the tissue seal owing to the thickness of the tissue. In various embodiments, the predetermined tissue thickness threshold can be in the range of 0 mm to 4 mm, alternatively in the range of 0.0 mm to 1.0 mm, alternatively in the range of 1 mm to 2 mm, and alternative in the range of 2 mm to 3 mm, for example. In other embodiments, the predetermined tissue thickness threshold can be set at other tissue thicknesses for various suitable applications. In various embodiments, more than one staple sensor 782 can be provided to sense staples in more than one staple cavity 704. In other various embodiments, a staple cartridge sensor (not illustrated) can be provided to sense the presence of a staple cartridge within the end-effector assembly 512.

In one embodiment, another lockout device can be configured to deactivate the electrode system when the sensed thickness of the tissue is greater than the predetermined tissue thickness threshold and when the sensor 782 does not sense a staple 722 in or at least partially in the first, undeployed position. To accomplish the same, the lockout device can be in electrical communication with the processor and can essentially function as a switch. When the lockout device receives a signal from the processor that the tissue thickness is greater than the predetermined tissue thickness threshold and/or no staples 722 are sensed in or at least partially in the first position by the sensor 782, the lockout device can interrupt the energy flow to the various electrodes of the end-effector assembly 512 by opening a switch positioned in series with the conductor supplying energy to the electrode. The lockout device can then allow energy flow to the various electrodes when the staples 722 are sensed in or at least partially in the first position by the sensor 782. Such a feature can prevent, or at least inhibit, sealing of tissue that is too thick to be sealed without the use of fasteners, such as staples, for example.

In one embodiment, a predetermined tissue sealing time can be associated with each tissue thickness or each range of tissue thickness. For example, if the tissue thickness is in the range of 3 mm to 8 mm, the tissue sealing time (or time energy is flowing through the end-effector assembly 512) can be 5 to 10 seconds, for example. In one embodiment, for a 45 mm staple cartridge, the tissue sealing time can be 4 to 15 seconds or longer, for example. Longer tissue sealing times may be helpful or required for staple cartridges longer than 45 mm. In various embodiments, when the energy flow to the end-effector assembly 512 is activated by retraction of the firing trigger 528, the cutting member 548 can be restricted in its movement along the cutting member slot 549 in the staple cartridge 537 or the second jaw 516. Such restriction can be to cause adequate energy flow to the various electrodes and create a suitable seal in the tissue for a predetermined period of time prior to advancing the cutting member 548. In one embodiment, the speed of the cutting member 548 can be modulated by allowing the cutting member 548 to be energized so that energy at the cutting edge enhances the sharpness of the cutting edge. If the cutting member 548 moves too quickly along the cutting member slot 549, a seal may not be fully formed in the tissue depending on the thickness of the tissue. The restriction of the movement of the cutting member 548 can be effected by a resistive member acting on or against the firing bar 514 or another cutting member, for example. In one embodiment, the resistive member can comprise a biasing or biased member that pushes against a side surface or other portion of the firing bar 514 or another cutting member to create a frictional resistance to proximal to distal movement of the firing bar 514 or another cutting member. In other embodiments, magnets can be used as the resistive member to restrict proximal to distal movement of the firing bar 514 or another cutting member.

Figure 29:
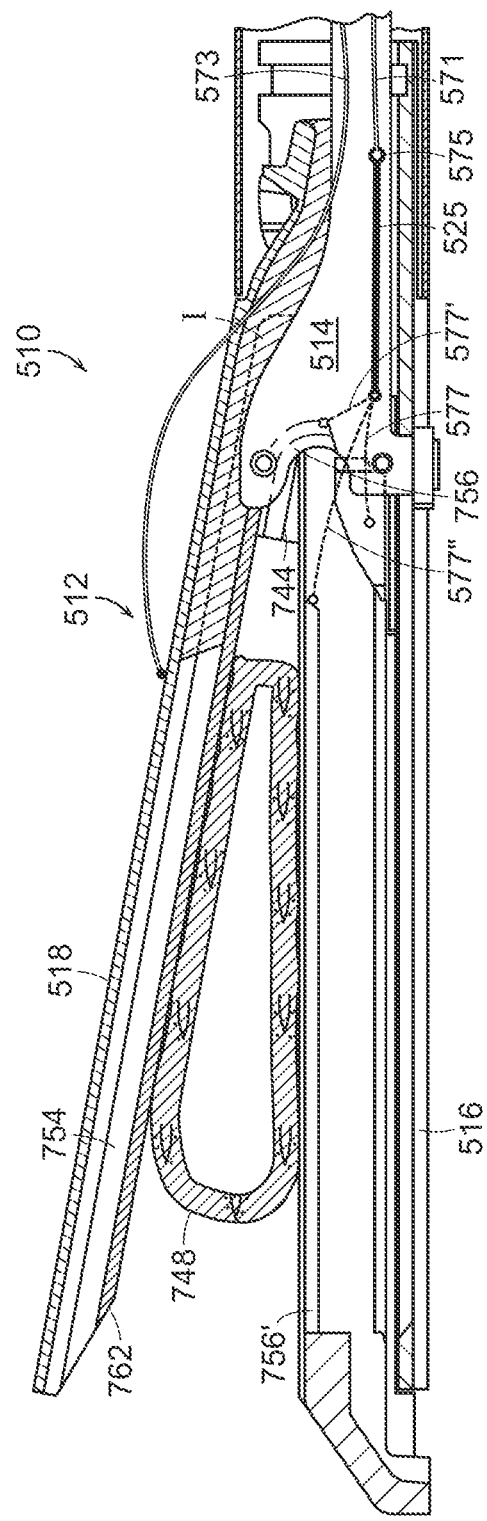
FIG. 29 is a cut-away side view of the end-effector assembly of FIG. 13 taken along the longitudinal centerline of the end-effector assembly in an open position in accordance with one non-limiting embodiment of the present disclosure.

In use, in one embodiment, the surgical stapling and severing instrument 510 can be used as illustrated in FIGS. 13, 14, and 29-35. In FIGS. 13 and 14, the surgical instrument 510 is in its initial position, having had an unfired, fully loaded staple cartridge 537 snap-fitted or otherwise fitted into the distal end of the second jaw 516. Both of the triggers 526, 528 are forward and the end-effector assembly 512 is open, such as would be typical after inserting the end-effector assembly 512 through a trocar or other opening into a body cavity of a patient. The surgical instrument 510 can then be manipulated by the surgeon such that tissue 748 to be stapled, sealed, and/or severed is positioned between the staple cartridge 537 and the first jaw 518, as illustrated in FIG. 29.

In various embodiments, referring to FIGS. 30 and 31, next, the surgeon can move the closure trigger 526 proximally until it is positioned adjacent or directly adjacent to the pistol grip 524, thereby locking the handle portion 520 into the closed and clamped position. The retracted firing bar 514 in the end-effector assembly 512 may not impede the selective opening and closing of the end-effector assembly 512, but rather resides within the anvil pocket 540. With the first jaw 518 closed and clamped, the firing bar 514 can be aligned for firing through the end-effector assembly 512. In particular, the upper pin 538 can be aligned with the anvil slot 542 and the second jaw 516 can be affirmatively engaged about the channel slot 545 by the middle pin 546 and the firing bar cap 544.

In one embodiment, referring to FIGS. 32 and 33, after tissue clamping has occurred, the surgeon can move the firing trigger 528 proximally to cause the firing bar 514 to move distally into the end-effector assembly 512. In particular, the middle pin 546 can enter the staple cartridge 537 through the firing drive slot 547 to effect the firing of the staples 722 (not illustrated in FIGS. 32 and 33) via wedge sled 718 toward the first jaw 518. The lower most pin, or firing bar cap 544, can cooperate with the middle pin 546 to slidingly position cutting member 548 of the firing bar 514 to sever the tissue 748. The firing bar cap 544 and middle pin 546 can also position the upper pin 538 of the firing bar 514 within the longitudinal anvil slot 542 of the first jaw 518, affirmatively maintaining the spacing between the first jaw 518 and the second jaw 516 throughout its distal firing movement.

In one embodiment, referring to FIGS. 34 and 35, the surgeon can continue moving the firing trigger 528 until brought proximal to the closure trigger 526 and the pistol grip 524. As a result, all of the ends of the staples 722 can be deformed owing to their engagement with the first jaw 518. The firing bar cap 544 can be arrested against a firing bar stop 750 projecting toward the distal end of the channel slot 545. In such a position, the cutting member 548 has traversed completely through the tissue 748. The process can be completed by releasing the firing trigger 528 and by then depressing the release button 530 while simultaneously squeezing the closure trigger 526 to open the end-effector assembly 512.

In one embodiment, the retraction of the firing trigger 528 can activate the electrode system of the surgical instrument 510 by closing a switch in the first conductor 571, for example, thereby allowing energy from the energy source 768 to flow to and through the end-effector assembly 512 and back to the energy source 768. The energy can flow from one electrode, such as the first electrode, in electrical communication with the first conductor 571, flow through the tissue clamped within the end-effector assembly 512 to create a seal in the tissue, and flow to the second electrode 754, for example. In other embodiments, the energy can flow to a third or a fourth electrode depending on the electrode configuration within the end-effector assembly 512. The energy can then flow back to the energy source 768, thereby completing the circuit between the surgical instrument 510 and the energy source 768.

In other various embodiments, referring to FIG. 13, the energy can flow to the end-effector assembly 512 and at least one electrode thereof when the activation button 764 is depressed. Depression of the activation button 764 can close the switch 579 in the first conductor 571 to allow energy to flow the end-effector assembly for a predetermined amount of time or as long as the activation button 764 is depressed by the surgeon.

The present disclosure has been illustrated by describing several embodiments and while the example embodiments have been described in detail, it is not the intention of the applicants to restrict or in any way limit the scope of the appended claims to such detail. Additional advantages and modifications will be readily apparent to those of skill in the art.

For example, the affirmative spacing of the first jaw 518 and the second jaw 516 can be achieved in part with two pins 544 and 546 on the firing bar 514 engaging opposite sides of a channel slot and a single upper pin 538 entrained within an first jaw slot 542. It would be consistent with aspects of the present disclosure for a first jaw to be captured by opposing pins on either side of a longitudinal slot and/or for a second jaw to have an internal slot that entrains a lower pin.

As another example, although the firing bar 514 has various advantages for an endoscopically employed surgical instrument 510, a similar firing bar may be used in other clinical procedures. It is generally accepted that endoscopic procedures are more common than laparoscopic procedures. Accordingly, the present disclosure has been discussed in terms of endoscopic procedures and apparatuses. However, use herein of terms such as "endoscopic," should not be construed to limit the present disclosure to a surgical instrument for use only in conjunction with an endoscopic tube (i.e., trocar). On the contrary, it is believed that the present disclosure may find use in any procedure where access is limited to a small incision, including but not limited to laparoscopic procedures, as well as open procedures.

As still another example, although an illustrative handle portion 520 described herein is manually operated by a surgeon, it is consistent with aspects of the present disclosure for some or all of the functions of a handle portion to be powered (e.g., pneumatic, hydraulic, electromechanical, ultrasonic, robotic etc.). Furthermore, controls of each of these functions can be manually presented on a handle portion or be remotely controlled (e.g., wireless remote, automated remote console, etc.), for example.

In one embodiment, referring to FIGS. 39-41, 47, and 48, a surgical instrument, such as surgical instrument 910, can comprise an elongate shaft 912 comprising a first proximal end 914 and a second distal end 916. A handle portion 918 can extend from the first end 914 and an end-effector 920 or an end-effector assembly can extend from the second end 916. In various embodiments, the surgical instrument 910 can be used to sever and/or join tissue or layers of tissue. In various embodiments, the surgical instrument 910 can be used to create a seal in tissue. In one embodiment, the surgical instrument 910 can be operably connected to an energy source 968 such that energy can flow to the end-effector 920 to seal tissue and then flow back to the energy source 968. Such energy flow and the energy source 968 can be the same as or similar to that described herein with respect to surgical instrument 510 and the energy source 768, for example. The energy source 968 can be operatively connected with a controller 970, which can be the same as or similar to the controllers 70 and/or 770 described above.

In one embodiment, the handle portion 918 can comprise an articulation knob 919 configured to rotate the end-effector 920 about a longitudinal axis of the elongate shaft 912. Such articulation can be useful in positioning the end-effector 920 during a surgical procedure. The handle portion 918 can also comprise a trigger 922 and a trigger 923. The trigger 922 can be used to close the end-effector 920 and clamp or compress tissue therein, while the trigger 923 can be used to distally advance a cutting member to cut tissue positioned within the end-effector 920 and/or distally advance a rivet driver to deploy or fire rivets from the end-effector 920 and into the tissue. In various embodiments, the cutting member can be part of the rivet driver, for example. In one embodiment, the trigger 923 can be geared such that more than one stroke of the trigger 923 can be used to distally advance the cutting member and/or the rivet driver. In other embodiments, only one trigger may be provided and that trigger can close the end-effector 920 and also distally advance the cutting member and/or the rivet driver. In various embodiments, the handle portion 918 or one of the triggers can comprise an activation button 964, as described herein.

In one embodiment, still referring to FIGS. 39-41, 47 and 48, the end-effector 920 can comprise a first jaw 926 and a second jaw 928. At least one of the first jaw 926 and the second jaw 928 can be moved toward each other by retraction of the trigger 922, for example, to thereby compress or clamp tissue positioned therebetween. In one embodiment, the first jaw 926 can be moved or pivoted toward the second jaw 928 to compress tissue therebetween. Such tissue compression can aid in sealing the tissue using rivets or electrodes in that the compression can reduce the amount of water in the tissue and can reduce the thickness of the tissue at locations in the tissue where a rivet line or a seal is to be formed. In one embodiment, the first portion 926 can comprise an anvil comprising anvil pockets 958. The anvil pockets 958 can be formed in the first portion 926 and can be configured to deform portions of rivets or staples. In other embodiments, the anvil pockets 958 may not be provided and a face of the anvil can deform and/or melt portions of the rivets. In one embodiment, formation of rivet heads can be dependent on the shape of the anvil pockets 958. Cubical-shaped anvil pockets can create cubical-shaped rivet heads and half sphere-shaped anvil pockets can create half sphere-shaped rivet heads, for example. Other shapes of the rivet heads are also envisioned within the scope of the present disclosure. In various embodiments, the first portion 926 can comprise a first electrode 954 and an optional fuse 962, such as the PTC material, for example, as discussed in further detail herein. In various embodiments, one or more insulative materials can also be provided on the face or other portions of the first jaw 926 to properly direct the energy flow within the end-effector 920. In other embodiments, the first electrode 954 can be at least a portion of the first portion 926, for example.

In one embodiment, the second jaw 928 can comprise a rivet cartridge receiving portion 929 configured to receive or at least partially receive a rivet cartridge 949 in a snap-fit or a press-fit fashion, for example. In various embodiments, the rivet cartridge 949 and/or the rivet cartridge receiving portion 929 can comprise a second electrode 960 and an optional fuse 962, such as the PTC material, for example, as discussed in further detail herein. In certain embodiments, the fuse 962 can be provided on both of the first portion 926 and the second portion 928 or on one of the first portion 926 and the second portion 928. The rivet cartridge 949 and/or the second jaw 928 can also comprise one or more insulative materials to help direct the energy between the electrodes 954 and 960 or between other various electrodes. Although the present disclosure discusses the rivet cartridge 949 comprising rivets, it will be understood that the rivet cartridge 949 can also comprise staples or other fasteners in addition to the rivets. Such a cartridge may be suitable for various surgical procedures. Also, although the rivet cartridge 949 is illustrated and described herein, it will be understood that rivet cavities can be formed in the second jaw 928 and that a separate rivet cartridge may not be required. Further, those of skill in the art will understand that the rivet cartridge 949, if provided, can be formed with or formed on the second jaw 928. As such, an end-effector or a surgical instrument used to deploy rivets can be provided with or without the rivets and/or with or without the rivet cartridge 949. In various embodiments, the rivet cartridge 949 can be disposable or can be reusable after being reloaded with rivets.

Figure 39:
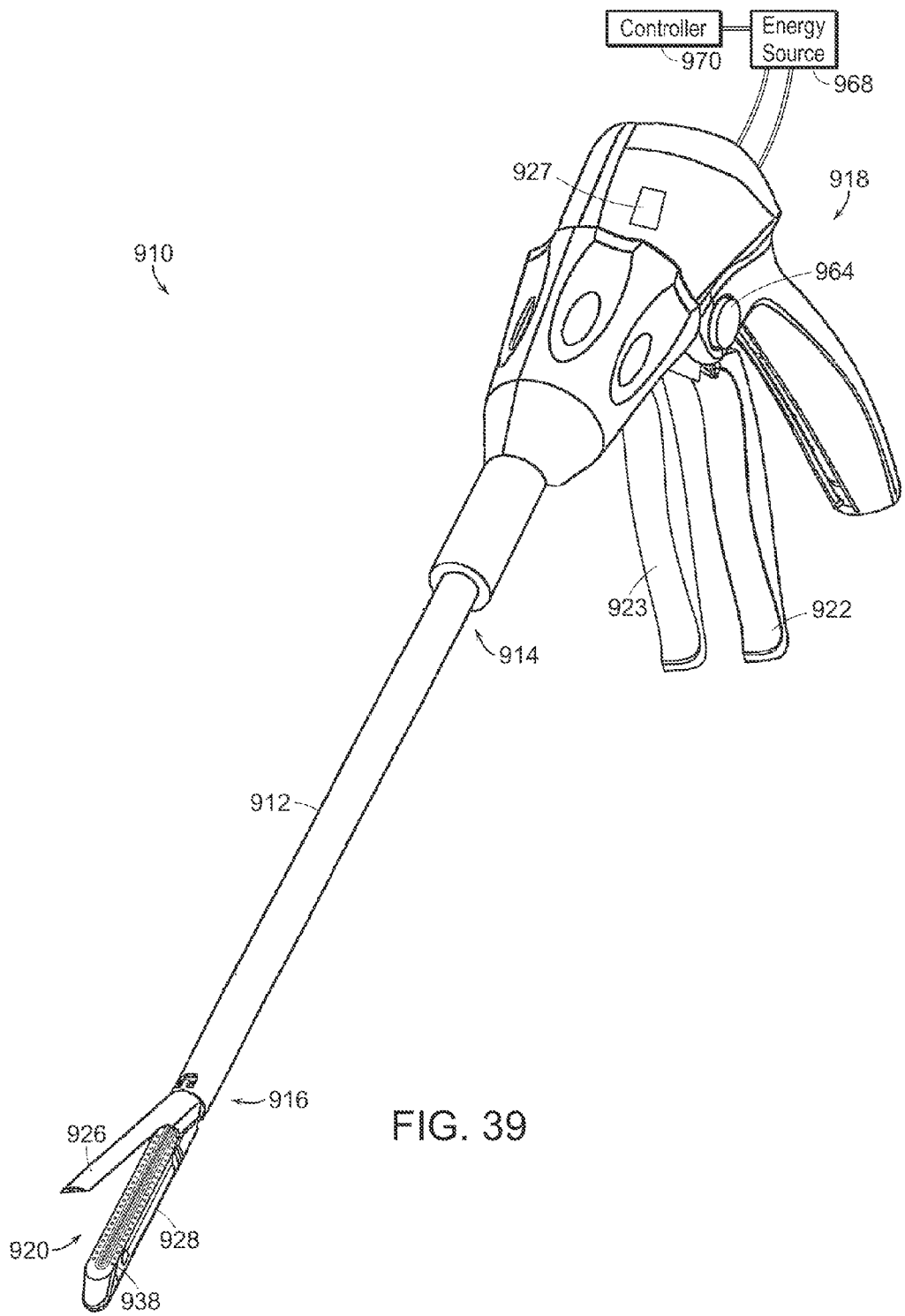
FIG. 39 is a perspective view of a surgical instrument configured to deploy rivets in accordance with one non-limiting embodiment of the present disclosure.
Figure 40:
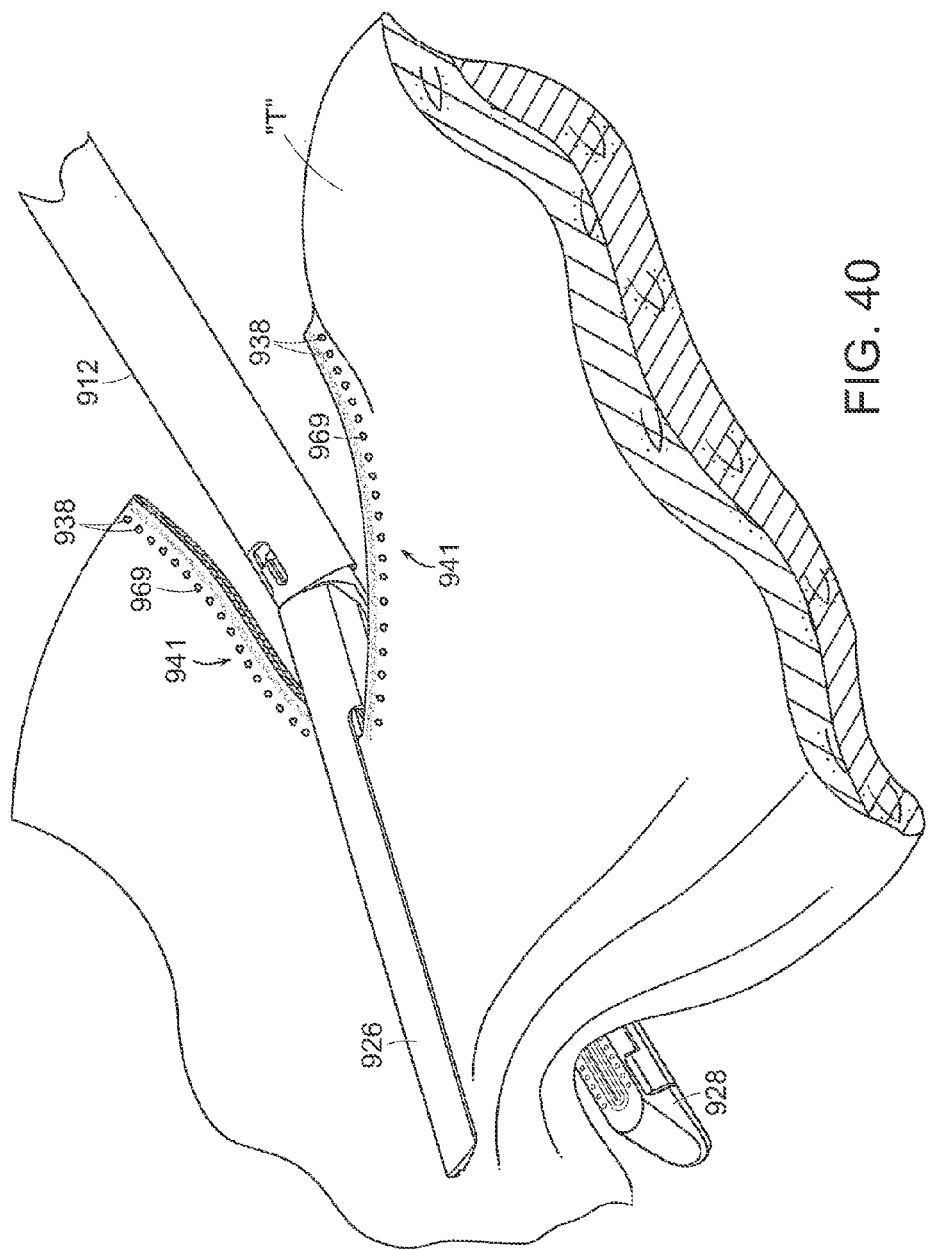
FIG. 40 is a perspective view of an end-effector of the surgical instrument of FIG. 39 cutting, sealing, and forming a rivet line in tissue in accordance with one non-limiting embodiment of the present disclosure.
Figure 41:
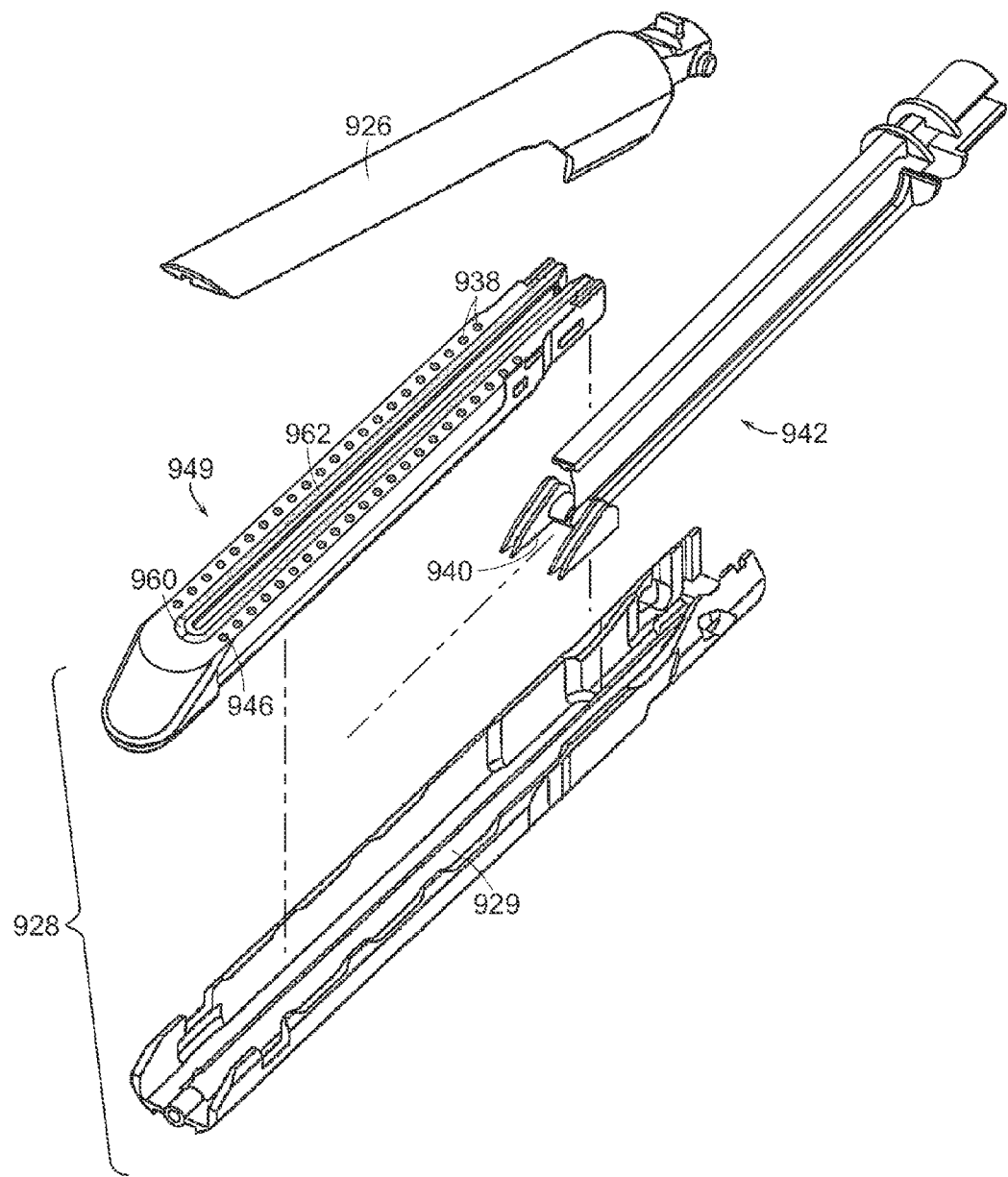
FIG. 41 is an exploded perspective view of an end-effector of the surgical instrument of FIG. 39 in accordance with one non-limiting embodiment of the present disclosure.

In one embodiment, referring to FIGS. 39-41, the trigger 922 can be retracted proximally to close the end-effector 920 and compress tissue "T" between the first jaw 926 and the second jaw 928. Once suitable tissue compression in the end-effector 920 is achieved, using a tissue compression indicator and/or a rivet formation indicator 927, for example, the trigger 923 can be retracted proximally one or more times (i.e., more than one stroke) to drive a cutting member 940 and a driver 942 distally within the end-effector 920. A stroke of the trigger 923 could advance the driver 942 ⅓ of the length of the rivet cartridge 949, for example. Such actuation can cause the driver 942 to move rivets 938 within the rivet cartridge 949 between a first position in which the rivets 938 can be at least partially positioned within a rivet cavity 946 and a second position in which the rivets 938 can be at least partially deployed from the rivet cavity 946. This can cause the rivets 938 to form a rivet line 941 in the tissue "T" by formation of the rivet heads 969, as illustrated in one example embodiment in FIG. 40, and as discussed in further detail herein. The rivet heads 969 can be formed by deforming and/or melting portions of the rivets 938. In one embodiment, the rivet heads 969 and/or other portions of the rivets 938 can be melted and/or deformed at temperatures in the range of about 107° F. to about 121° F., for example. In other embodiments, the rivet heads 969 and/or other portions of the rivets 938 can be melted and/or deformed at temperatures in the range of about 100° C. to about 220° C., greater than about 50° C., or less than about 100° C. In the latter embodiment, the tissue being anchored by the rivets 938 may need to be insulated from this higher heat such that overheating or burning of the tissue does not occur. In still other embodiments, other suitable melting and/or deforming temperatures of the rivets 938 can be used depending on the material(s) of the rivets 938 as will be recognized by those of skill in the art. The actuation of the trigger 923 can also cause the cutting member 940 to advance distally within the end-effector 920 and sever or incise the tissue "T", again as illustrated in one example embodiment in FIG. 40. In one embodiment, the driver 942 and the cutting member 940 can be formed of a single component or can be formed of more than one component. In any event, both the cutting member 940 and the driver 942 can be configured to be driven distally within the end-effector 920 upon retraction of the trigger 923 or other suitable trigger.

The general operation of a surgical instrument, such as surgical instrument 910 is described in further detail herein and in U.S. Pat. No. 7,000,818 to Shelton et al., entitled SURGICAL STAPLING INSTRUMENT HAVING SEPARATE CLOSING AND FIRING SYSTEMS, which issued on Feb. 21, 2006, the entire disclosure of which is incorporated herein by reference in its entirety. The surgical instrument 910 can also operate in other fashions and still be within the scope of the present disclosure. Surgical instruments operably engaged with energy sources are described in greater detail above.

In one embodiment, referring to FIGS. 42 and 43, the rivet cartridge 949 is illustrated. The rivet cartridge 949 can be configured to be engaged with, attached to, or formed with an end-effector of a surgical instrument, such as the end-effector 920 of the surgical instrument 910, for example. In one embodiment, the rivet cartridge 949 can be configured to be positioned within the receiving portion 929 of the second portion 928. In one embodiment, although not illustrated, the rivet cartridge 949 can be engaged with, attached to, or formed with the first portion 926 and the second portion 928 can act as the anvil, for example. In various embodiments, the rivet cartridge 949 can comprise a first surface 950 defining one or more openings 952 therein and a second surface 953. One or more of the rivet cavities 946 can be defined at least partially intermediate the first surface 950 and the second surface 953. In one embodiment, the one or more rivet cavities 946 can extend from the first surface 950 to the second surface 953. The one or more rivet cavities 946 can be in communication with the openings 952 in the first surface 950. The rivet 938 can be removably positioned within each of the rivet cavities 946 and/or the openings 952 or less than each of the rivet cavities 946 and/or the openings 952. FIG. 43 illustrates a cross-sectional view of the rivet cartridge 949 taken along line 43-43 of FIG. 42. In FIG. 43, none of the rivets 938 have been fully deployed from the rivet cartridge 949. As such, the rivets 938 are illustrated in the stored position, or substantially in the stored position. In other embodiments, the rivet cartridge 949 can comprise other suitable configurations.

Figure 44:
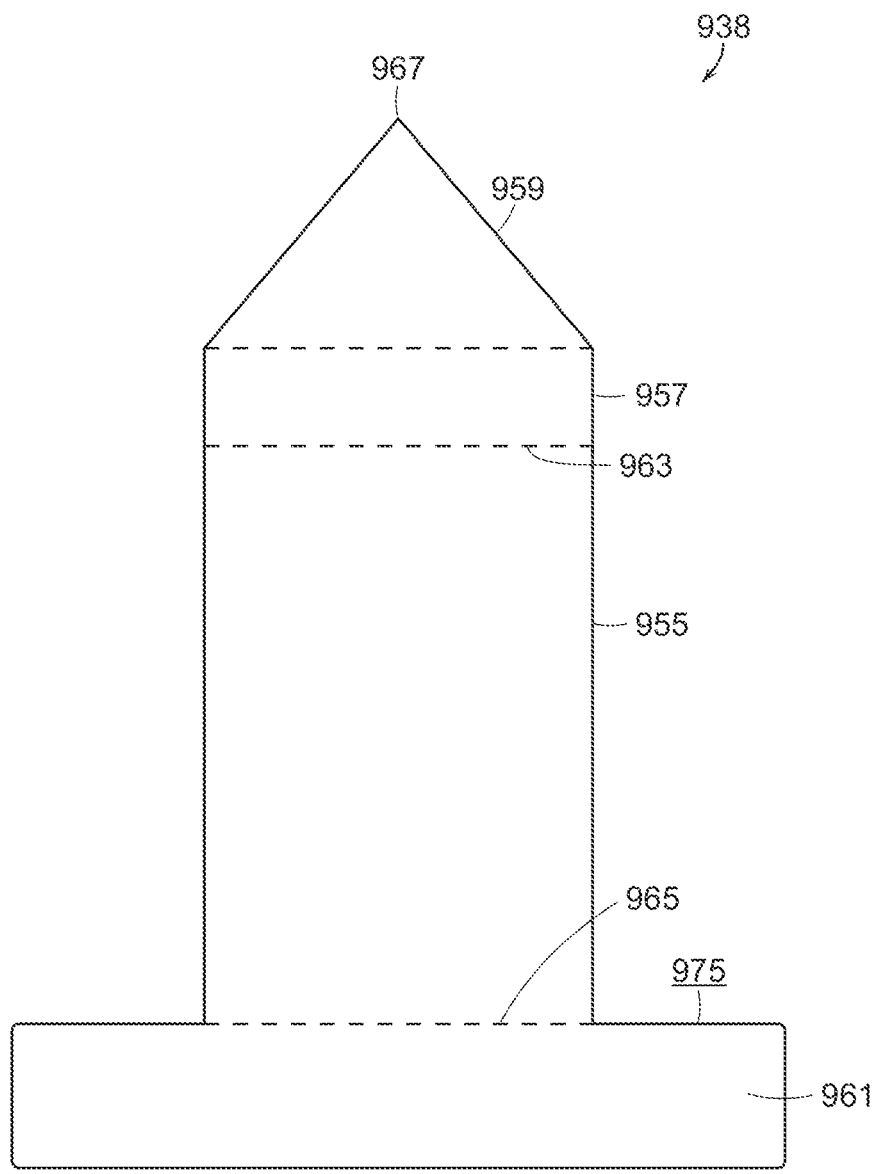
FIG. 44 is an elevation view of a rivet that can be deployed from an end-effector of the surgical instrument of FIG. 39 in accordance with one non-limiting embodiment of the present disclosure.

In various embodiments, referring to FIG. 44 as an example, the rivet 938 can comprise a tissue-engaging portion 955, an elongate portion 957 extending from the tissue-engaging portion 955, and a meltable and/or deformable portion 959. In one embodiment, the elongate portion 957 can comprise or form the meltable and/or deformable portion 959. The meltable and/or deformable portion 959 can be deformed by the first portion 926 or the anvil pockets 958 of the first portion 926 and/or melted by heat generated within the end-effector 920. In various embodiments, the rivet 938 can comprise a base 961 comprising a tissue-engaging surface 975. In such an embodiment, the tissue-engaging portion 955 of the rivet 938 can comprise a first end 963 and a second end 965, such that the elongate portion 957 extends from the first end 963 and the base 961 extends from the second end 965. In one embodiment, a base of the rivets can comprise a camming surface configured to be engaged with the driver 942 or a camming surface on the driver 942 to drive the rivets into tissue and against the first portion 926.

In one embodiment, the rivets 938 can comprise a meltable and/or a deformable material. Example materials can comprise collagen, keratin, synthetic absorbable and non-absorbable polymers, amorphous (as opposed to crystalline) thermoplastics, such as Noryl (blend of polyphenylene oxide and polystyrene), ABS (acrylonitrile butadiene styrene), polycarbonate, Ultem (polyetherimide), and/or polystyrene, for example, although other suitable materials can also be used. In one embodiment, the materials of the rivets 938 can comprise polylactic acid (PLA), high density polyethylene (HDPE), poly(lactic-co-glycolic acid) (PLGA), polyether ether ketone (PEEK), ethylene-vinyl acetate (EVA), and/or polyethylene oxide (PEO), for example. In various embodiments, the rivets 938 can comprise meltable and/or deformable portions, such as the meltable and/or deformable portion 959 and the elongate portion 957, for example. In one embodiment, the rivets 938 comprising the meltable and/or deformable material can have portions thereof melted through heat generated in the end-effector 920 by the resistance to energy flow through the tissue. In other embodiments, the rivets 938 comprising the meltable and/or deformable material can have portions thereof deformed by the first portion 926. In one embodiment, the rivets 938 can comprise absorbable and/or dissolvable materials, such as collagen, keratin, and/or synthetic absorbable materials, for example. These various materials can comprise biologically active components, for example. As a result of the usage of such materials, after the rivets 938 are deployed into the tissue and the end-effector 920 is removed from the surgical site, the rivets 938, over time, can be absorbed and/or dissolved into tissue and/or the body. In other various embodiments, the rivets 938 can comprise or can be coated with a medication, a therapeutic agent, and/or a collagen-based material to aid the tissue surrounding the rivets 938 in the healing process.

In one embodiment, the rivets 938 can comprise a tissue-puncturing tip 967 or tissue-piercing tip on the meltable and/or deformable portion 959 or on the elongate portion 957. The tissue-puncturing tip 967 can be configured to pierce tissue and/or buttress material, such as a collagen-based buttress material, for example, when forced into the tissue by the driver 942. In various embodiments, the tissue-puncturing tip 967 can be comprised of the same material as the meltable and/or deformable portion 959 and/or the elongate portion 957 or can be comprised of a different material, such as titanium or other biocompatible alloy, for example. In an embodiment where the tissue-puncturing tip 967 comprises the same materials as the meltable and/or deformable portion 959 or other meltable and/or deformable materials, it may be advantageous to first cut the tissue and then energize the end-effector and deploy the rivets 938 to prevent, or at least inhibit, the tissue-puncturing tip 967 from melting prior to being deployed into the tissue, for example.

In one embodiment, FIGS. 45 and 46 illustrate the rivets 938 in the process of being deployed or fired into tissue compressed intermediate the first jaw 926 and the second jaw 928. In various embodiments, the rivets 938 can be moved from the first stored position into a second deployed positioned using the driver 942. As illustrated in FIG. 46, the extent to which the rivets heads 969 of the rivets 938 are formed can be based on the tissue thickness where a particular rivet 938 is deployed into the tissue "T." Stated another way, in various embodiments, the rivets heads 969 can be melted and/or deformed more in thinner areas of the tissue and melted and/or deformed less in thicker areas of the tissue. Such adjustability of rivet head formation can allow a suitable bond to be formed in the tissue regardless of the thickness of the tissue where a particular rivet 938 is deployed. In one embodiment, the elongate portion 957 of the rivets 938 can have a first circumferential perimeter when the rivets 938 are in the first, stored position (i.e., the undeployed position) and can have a meltable and/or deformable portion 959 that has a second circumferential perimeter when the rivets 938 are moved into the second position (i.e., the deployed position). In such an embodiment, the second circumferential perimeter of the meltable and/or deformable portion 959 can be greater than the first circumferential perimeter of the elongate portion 957 after the rivet head 969 is formed. In one embodiment, the meltable and/or deformable portion 959 of the rivet 938 can have a first axial length when the rivet 938 is in the first stored position and can have a second axial length when the rivet 938 is in the second deployed position after the rivet head 969 is formed. The first axial length of the meltable portion 959 can be greater than the second axial length of the meltable and/or deformable portion 959 when the meltable and/or deformable portion 959 is at least partially melted or deformed. In various embodiments, the base 961 can form the other rivet head on the side of the tissue proximate to the second portion 928. In other embodiments, a rivet head can be formed on the rivet on the side of the tissue proximate to the second portion 928 by the driver 942 applying pressure to the rivet while deploying the rivet and/or by heat created within the end-effector 920. In any event, either a base or a rivet head is generally present on both ends of the various rivets when the rivets are deployed into tissue, such that the rivets remain within the tissue.

In one embodiment, the rivets 938 and the driver 942 can be comprised of or can comprise a conductive or electrically conductive portion such that energy can pass to the driver 942 and to the rivets 938 when the driver 942 is in contact with the rivets 938. In such an embodiment, the rivets 938 can be deformable, for example. Such a feature allows the rivets 938 to seal tissue as the rivets 938 are forced through the tissue by the driver 942, similar to that described above with respect to the staples 72.

Figures 47, 48:
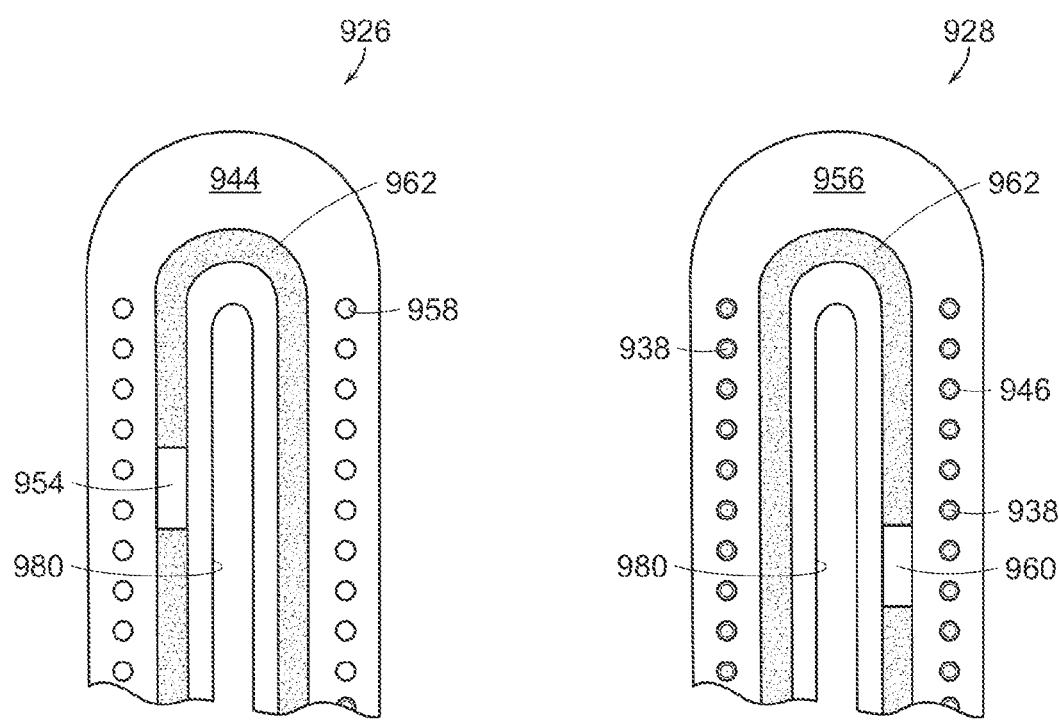
FIG. 47 is a partial view of a first face of a first portion of an end-effector in accordance with one non-limiting embodiment of the present disclosure.
FIG. 48 is a partial view of a second face of a second portion of an end-effector in accordance with one non-limiting embodiment of the present disclosure.

In one embodiment, referring to FIGS. 47 and 48, an example configuration of a first face 944 of the first jaw 926 (FIG. 47) and a second face 956 of the second jaw 928 (FIG. 48) is illustrated. In various embodiments, the first jaw 926 can comprise the first electrode 954 and optionally can comprise the fuse 962, such as the PTC material, for example, positioned at least partially over the first electrode 954. The cutting member 940 can be moved through a cutting member channel 980 when forced distally within the end-effector 920 by the driver 940. In one embodiment, the anvil pockets 958 can be formed in the first face 944. These anvil pockets 958 can be configured to receive the meltable and/or deformable portion 959 and/or the elongate portion 957 of the rivet 938 and deform and/or melt the same. Although, the anvil pockets 958 of FIG. 47 are illustrated as being dome-shaped, those of skill in the art will recognized that anvil pockets can be any other suitable shape configured to deform and/or melt portions of the rivet 938 and form the rivet head 969 in tissue. In one embodiment, the shape of the rivet heads 969 can be dependent on the shape of the anvil pockets 958. In other embodiments, the shape of the rivet heads 969 can be dependent on the shape of the meltable and/or deformable portion 959 and/or the elongate portion 957. The first face 944 can comprise an insulator material thereon to aid in directing energy from the first electrode 954 to the second electrode 960 with minimal thermal spread of the heat generated between the electrodes 954 and 960.

In one embodiment, referring to FIG. 48, the second face 956 of the second portion 928 can comprise the rivet cavities 946 which can each comprise the rivet 938 removably positioned therein. As discussed above, the rivet cavities 946 can be defined in the second portion 928 or defined in a rivet cartridge that can be attached to or engaged with the second portion 928. The second portion 928 can comprise the fuse 962, such as PTC material, for example, and can also comprise or can be comprised of the second electrode 960. In general, the fuse 962 is usually provided on only one of the first portion 926 and the second portion 928, although, in some embodiments, the fuse 962 can be provided on both of the first portion 926 and the second portion 928. For example, the second portion 928 can comprise conductive portions underneath the fuse 962. Similar to the first face 944, the second face 956 can comprise an insulator material thereon to aid in directing energy from the first electrode 954 to the second electrode 960 with minimal thermal spread of the heat generated between the electrodes 954 and 960.

In various embodiments, the rivets 938 in the rivet cavities 946 can be deployed by the driver 942 from the second portion 928 toward the first portion 926 or toward the anvil pockets 958 such that portions thereof can be deformed by the anvil pockets 958. In other embodiments, the rivets 938 can be deformed by the first face 944 of the first portion 926. At the same time, before, or after the rivets 938 are deployed into the tissue, the first electrode 954 or the second electrode 960 can be energized to supply energy to the tissue and to the first electrode 954 or the second electrode 954. The energy can be supplied to the first electrode 954 and returned from the second electrode 960 or can be supplied to the second electrode 960 and returned from the first electrode 954 similar to or the same as that described above. An activation button 964 (FIG. 39) can also be used to allow the energy to pass through the end-effector 920, similar to or the same as that described above. In one embodiment, various lockouts or lockout devices can also be provided in the rivet firing trigger 923 or in the activation button 964 similar to or the same as that described above.

In the example embodiments of FIGS. 47 and 48, the rivets 938 and the anvil pockets 958 are illustrated in a linear fashion and positioned outwardly from the first electrode 954, the second electrode 960, and the fuse 962. Such example embodiments are not intended to limit the scope of the present disclosure. In fact, the rivets 938 and the anvil pockets 958 can be positioned in a linear or non-linear fashion outwardly or inwardly from the first electrode 954, the second electrode 960, and the fuse 962, for example. In certain other embodiments, two or more lines of the rivets 938 can be provided. If two or more lines of the rivets 938 are provided, a first line of the rivets 938 can be staggered or off-set from the second line of the rivets 938 such that a better seal can be created in the tissue by reducing the spacing of gaps between the rivets 938. In one embodiment, one or more lines of the rivets 938 can be positioned on each side of the seal, for example. Furthermore, spacing between one rivet 938 and another rivet 938 may vary according to a particular surgical purpose of the rivets 938. As discussed above, in certain embodiments, staples or other suitable fasteners may also be used to compliment the rivets 938.

Figure 49:
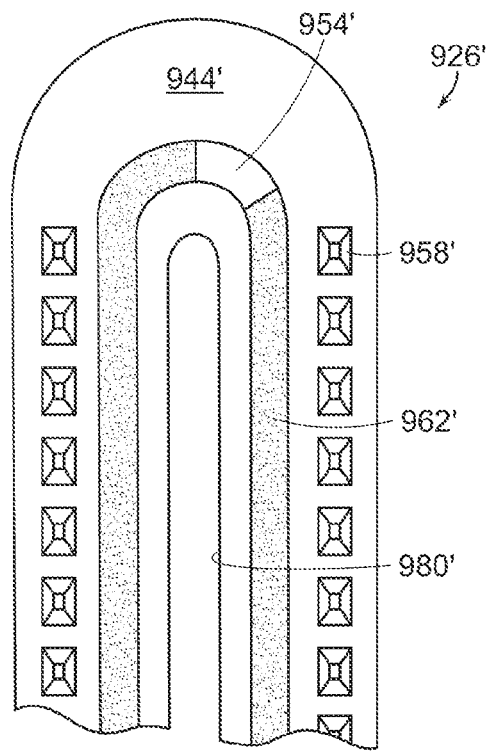
FIG. 49 is a partial view of a first face of a first portion of an end-effector in accordance with one non-limiting embodiment of the present disclosure.
Figure 50:
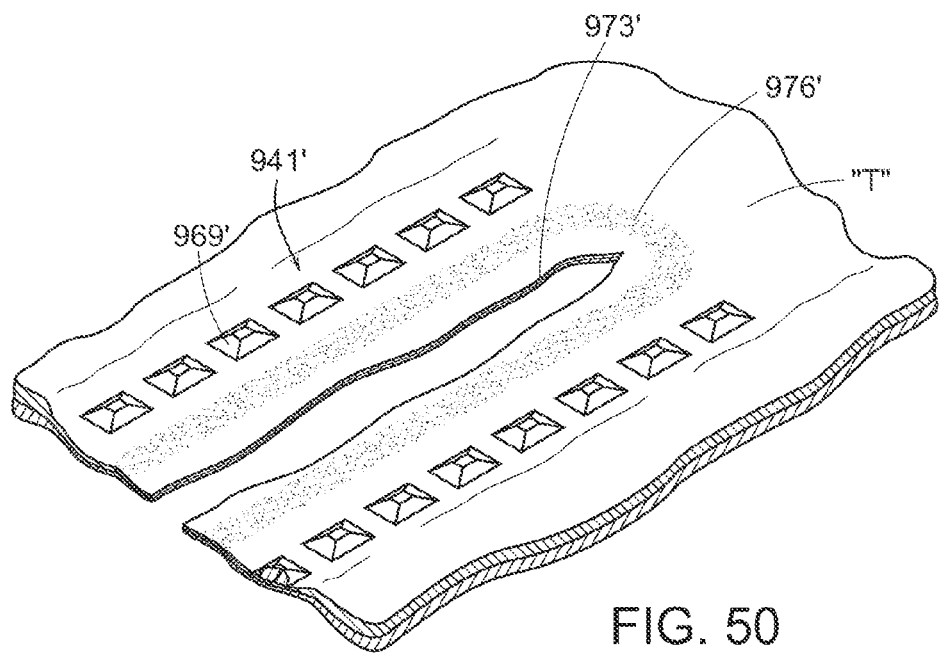
FIG. 50 is a view of a piece of tissue after an end-effector having the first portion of FIG. 49 has deployed rivets into the tissue, created a seal in the tissue, and created a cut line in the tissue in accordance with one non-limiting embodiment of the present disclosure.

In one embodiment, referring to FIGS. 49 and 50, another example of a first portion 926' that can be used with the second portion 928 of FIG. 48 is provided. In such an embodiment, anvil pockets 958' can be defined in a first face 944'. The anvil pockets 958' can have a rectangular or substantially rectangular opening at or proximate to the first face 944' to produce a rivet line 941' having rivet heads 969' in the tissue "T" as illustrated in FIG. 50. The tissue can also comprise a seal 976' produced by the electrodes and a cut line 973' produced by the cutting member 940 when the cutting member 940 is moved along the cutting member channel 980'.

Figure 51:
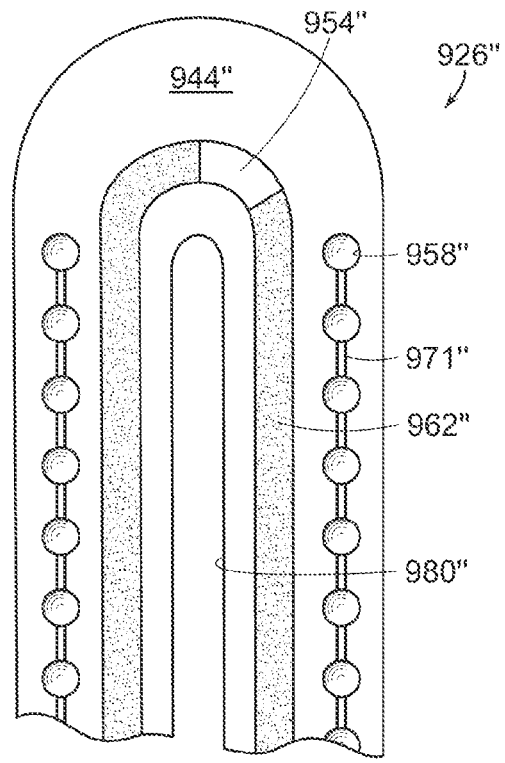
FIG. 51 is a partial view of a first face of a first portion of an end-effector in accordance with one non-limiting embodiment of the present disclosure.
Figure 52:
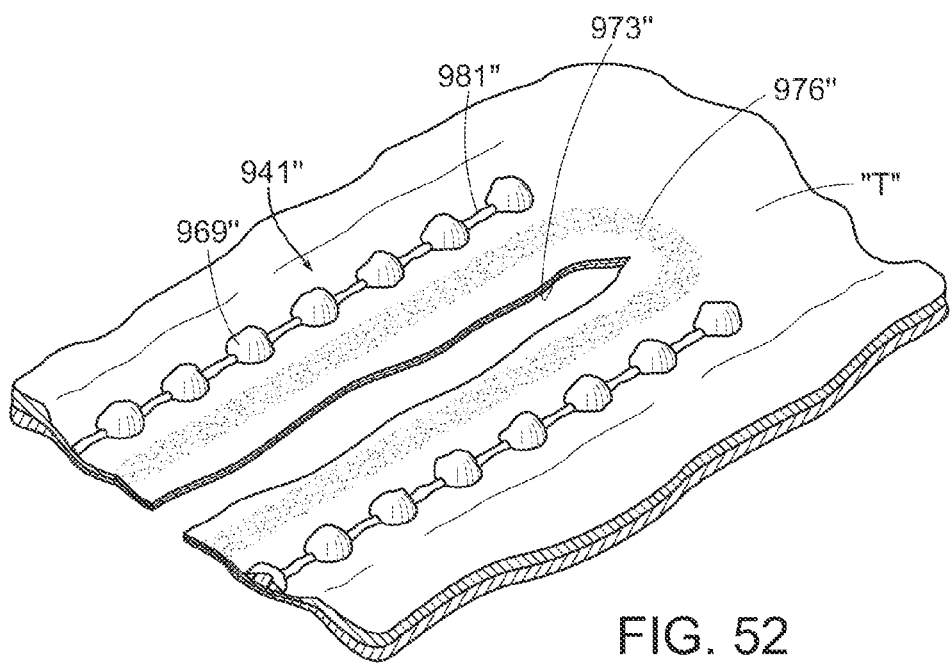
FIG. 52 is a view of a piece of tissue after an end-effector having the first portion of FIG. 51 has deployed rivets into the tissue, created a seal in the tissue, and created a cut line in the tissue in accordance with one non-limiting embodiment of the present disclosure.

In one embodiment, referring to FIGS. 51 and 52, another example of a first portion 926" that can be used with the second portion 928 of FIG. 48 is provided. In such an embodiment, anvil pockets 958" can be defined in a first face 944". Channels 971" can be defined in the first face 944" intermediate a first anvil pocket 958" and a second anvil pocket 958". The anvil pockets 958" can have a circular or substantially circular opening at or proximate to the first face 944" to produce a rivet line 941" having rivet heads 969" in the tissue "T" connected by elongate members 981" as illustrated in FIG. 52. The elongate members 981" can be formed by portions of the rivets 938" being melted and/or being deformed within the channels 971". As can be seen in FIG. 52, the rivets 938" of the rivet line 941" can be connected to each other from the rivet material melted within the channels 971". As a result, the rivet line 941" can be robust and can create an appropriate seal in the tissue or layers of tissue. Such a rivet line 941" can also protect, by providing structural support to the tissue "T", the seal 976" formed in the tissue "T" around the cut line 973" by the various electrodes. The cut line 973" can be formed by the cutting member 940 moving along the cutting member channel 980".

Figure 53:
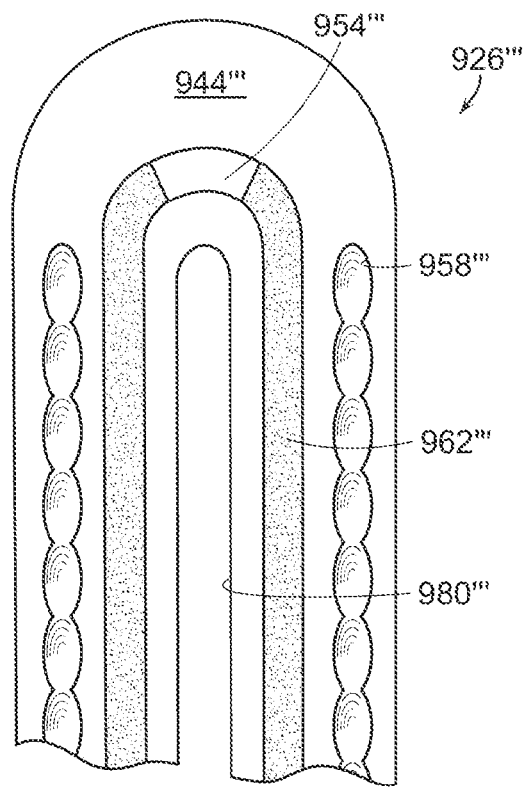
FIG. 53 is a partial view of a first face of a first portion of an end-effector in accordance with one non-limiting embodiment of the present disclosure.
Figure 54:
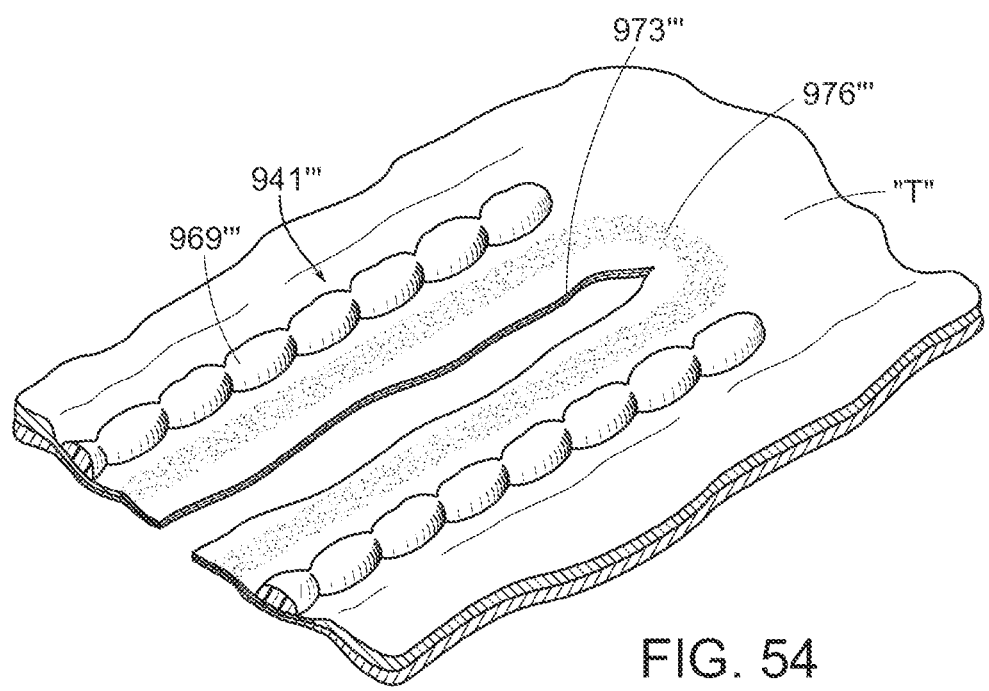
FIG. 54 is a view of a piece of tissue after an end-effector having the first portion of FIG. 53 has deployed rivets into the tissue, created a seal in the tissue, and created a cut line in the tissue in accordance with one non-limiting embodiment of the present disclosure.

In one embodiment, referring to FIGS. 53 and 54, another example of a first portion 926'" that can be used with the second portion 928 of FIG. 48 is provided. In such an embodiment, anvil pockets 958'" can be defined in a first face 944'". One anvil pocket 958'" can touch or be positioned very proximal to another anvil pocket 958'" to form a rivet line 941'" in the tissue "T" as illustrated in FIG. 54. The anvil pockets 958'" can have an elongate opening at or proximate to the first face 944'" to produce the rivet line 941'" having rivet heads 969'". As can be seen from FIG. 54, the rivet heads 969'" of the rivets 938'" can be connected to each other from the rivet material melted within the anvil pockets 958'". As a result, the rivet line 941'" can be robust and can create an appropriate seal in the tissue or layers of tissue. Such a rivet line 941'" can also protect, by providing structural support to the tissue, a seal 976'" formed in the tissue by the various electrodes around the cut line 973'". The cut line 973'" can be formed by the cutting member 940 moving along a cutting member channel 980'". Those of skill in the art will recognize that other suitable patterns of rivets and/or rivet lines are within the scope of the present disclosure.

Figure 55A:
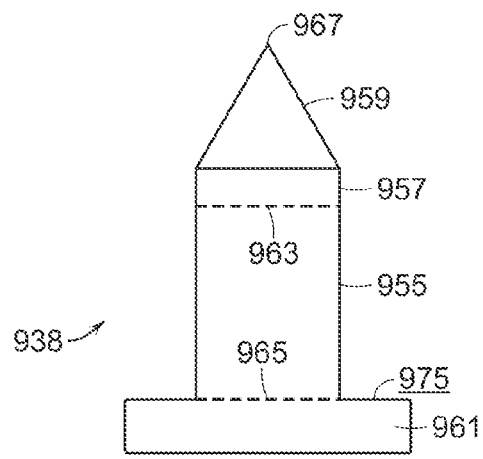
FIG. 55A is an elevation view of a rivet in an undeformed, unmelted, and/or undeployed state in accordance with one non-limiting embodiment of the present disclosure.
Figure 55B:
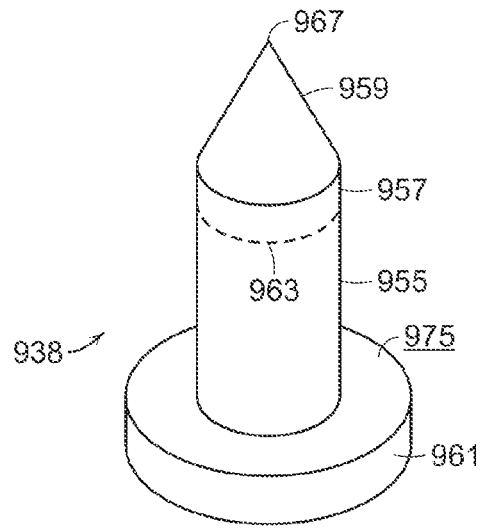
FIG. 55B is a perspective view of the rivet of FIG. 55A in accordance with one non-limiting embodiment of the present disclosure.
Figure 55C:
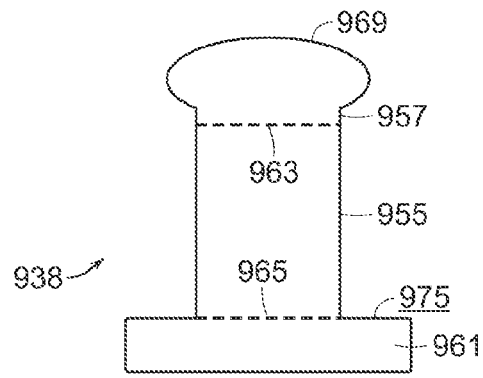
FIG. 55C is an elevation view of the rivet of FIGS. 55A and 55B in a melted, deformed, and/or deployed state in accordance with one non-limiting embodiment of the present disclosure.

In one embodiment, referring to FIGS. 55A-55C, a rivet 938 is illustrated. The rivet 938 is illustrated in the undeployed, undeformed, and/or unmelted state in FIGS. 55A and 55B and is illustrated, in one example embodiment, in a deployed, deformed, and/or melted state in FIG. 55C. In one embodiment, the rivet 938 can comprise a tissue-puncturing tip 967, a meltable and/or deformable portion 959, an elongate portion 957, a tissue-engaging portion 955, and a base 961. The tissue engaging-portion 955 can comprise a first end 963 and a second end 965. The elongate portion 957 can extend from the first end 963 and the base 961 can extend from the second end 965. The base 961 can comprise a tissue-engaging surface 975. The meltable and/or deformable portion 959 and possibly a portion of the elongate portion 957 can be deformed by the first face of the first portion and the driver and can be at least partially melted by heat within the end-effector generated by the resistance to the energy flow that the tissue provides intermediate the first electrode and the second electrode. In such an embodiment, the elongate portion 957 and/or the meltable and/or deformable portion 959 can form a rivet head 969 while the base 961 can form the other rivet head.

In one embodiment, referring to FIG. 46, a buttress material "B", such as a collagen-based buttress material, for example, can be positioned intermediate the first jaw 926 and the second jaw 928 and/or can be attached to one of the first jaw 926 and the second jaw 928. The tissue-puncturing tip 967 or other various tissue-puncturing tips can be configured to puncture not only the tissue, but also the buttress material when the rivet 938 is deployed towards the first portion 926. Such use of the collagen-based buttress material can aid the healing process in the area near the cut line 973 or where the rivets 938 have punctured the tissue. Such a buttress material can be used with any of the other rivets or end-effectors of the present disclosure in the same or a similar fashion.

Figure 56A:
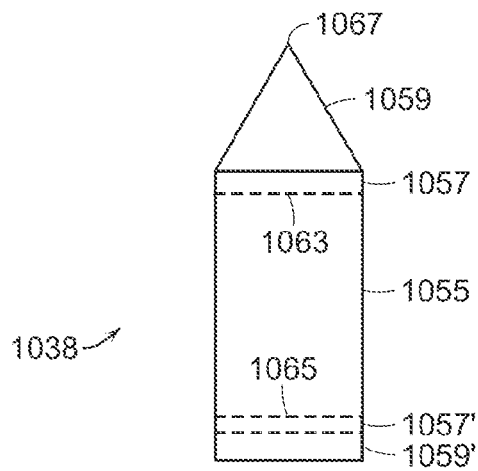
FIG. 56A is an elevation view of a rivet in an undeformed, unmelted, and/or undeployed state in accordance with one non-limiting embodiment of the present disclosure.
Figure 56B:
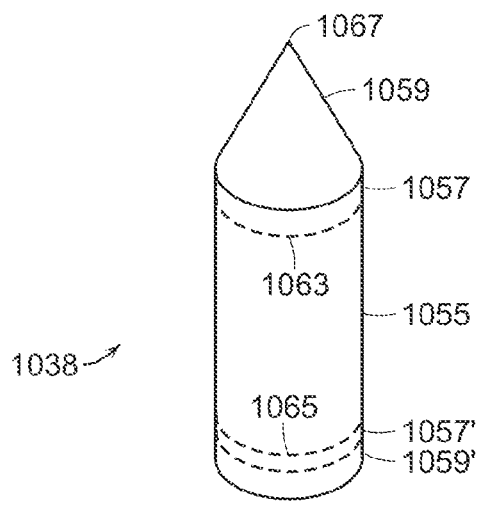
FIG. 56B is a perspective view of the rivet of FIG. 56A in accordance with one non-limiting embodiment of the present disclosure.
Figure 56C:
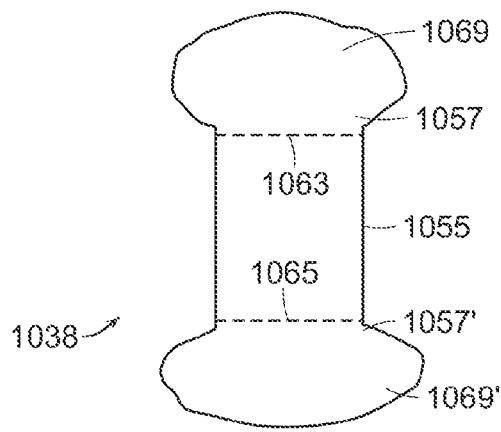
FIG. 56C is an elevation view of the rivet of FIGS. 56A and 56B in a melted, deformed, and/or deployed state in accordance with one non-limiting embodiment of the present disclosure.

In one embodiment, referring to FIGS. 56A-56C, a rivet 1038 is illustrated. The rivet 1038 is illustrated in the undeployed, undeformed, and/or unmelted state in FIGS. 56A and 56B and is illustrated, in one example embodiment, in a deployed, deformed, and/or melted state in FIG. 56C. In one embodiment, the rivet 1038 can comprise a tissue-puncturing tip 1067, a meltable and/or deformable portion 1059, an elongate portion 1057, a tissue-engaging portion 1055, a second elongate portion 1057', and a second meltable and/or deformable portion 1059'. The tissue engaging-portion 1055 can comprise a first end 1063 and a second end 1065. The elongate portion 1057 can extend from the first end 1063 and the second elongate portion 1057' can extend from the second end 1065. The meltable and/or deformable portions 1059 and 1059' and possibly a part of the elongate portions 1057 and 1057' can be deformed and/or melted by the first face of the first portion and the driver and can be melted by heat within the end-effector generated by the resistance to the energy flow that the tissue provides intermediate the first electrode and the second electrode. In such an embodiment, the elongate portions 1057 and 1057' and/or the meltable and/or deformable portions 1059 and 959' can form rivet heads 1069 and 1069'.

Figure 57A:
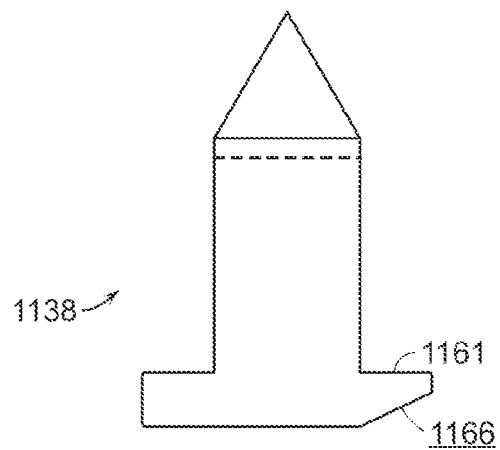
FIG. 57A is an elevation view of a rivet in an undeformed, unmelted, and/or undeployed state in accordance with one non-limiting embodiment of the present disclosure.
Figure 57B:
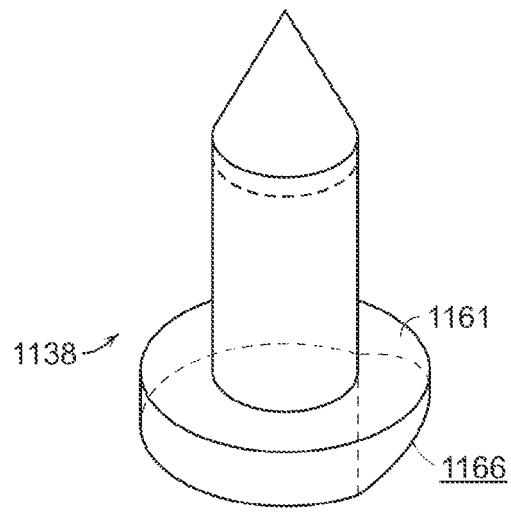
FIG. 57B is a perspective view of the rivet of FIG. 57A in accordance with one non-limiting embodiment of the present disclosure.
Figure 57C:
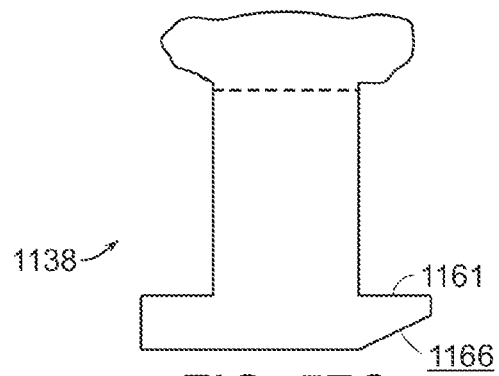
FIG. 57C is an elevation view of the rivet of FIGS. 57A and 57B in a melted, deformed, and/or deployed state in accordance with one non-limiting embodiment of the present disclosure.

In one embodiment, referring to FIGS. 57A-57C, a rivet 1138 is illustrated. The rivet 1138 is illustrated in the undeployed, undeformed, and/or unmelted state in FIGS. 57A and 57B and is illustrated, in one example embodiment, in a deployed, deformed, and/or melted state in FIG. 57C. In one embodiment, the rivet 1138 can be similar to the rivet 938, but can comprise a base 1161 comprising a camming surface 1166 configured to be engaged with the driver or a camming surface on the driver to drive the rivets 1138 into tissue. In one embodiment, such a camming surface 1166 can be provided on all of the rivets of the present disclosure.

Figure 58A:
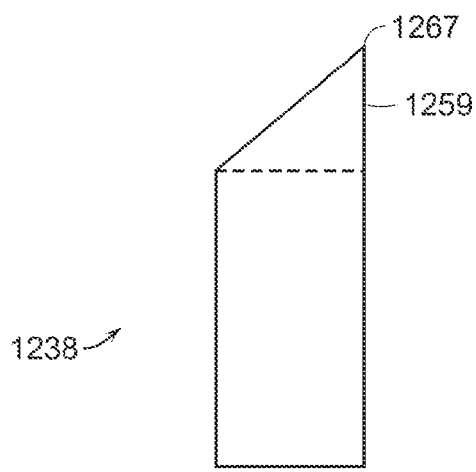
FIG. 58A is an elevation view of a rivet in an undeformed, unmelted, and/or undeployed state in accordance with one non-limiting embodiment of the present disclosure.
Figure 58B:
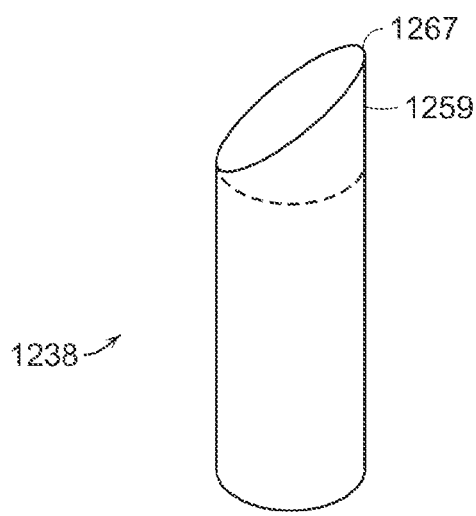
FIG. 58B is a perspective view of the rivet of FIG. 58A in accordance with one non-limiting embodiment of the present disclosure.
Figure 58C:
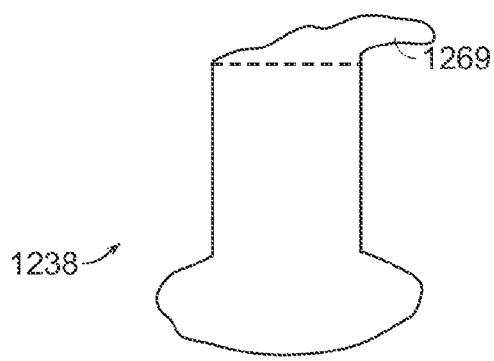
FIG. 58C is an elevation view of the rivet of FIGS. 58A and 58B in a melted, deformed, and/or deployed state in accordance with one non-limiting embodiment of the present disclosure.

In one embodiment, referring to FIGS. 58A-58C, a rivet 1238 is provided. The rivet 1238 is illustrated in the undeployed, undeformed, and/or unmelted state in FIGS. 58A and 58B and is illustrated, in one example embodiment, in a deployed, deformed, and/or melted state in FIG. 58C. In one embodiment, the rivet 1238 can be similar to the rivet 1038, but can comprise a different tissue-puncturing tip 1267 and a meltable and/or deformable portion 1259 configured to be formed into a rivet head 1269.

Figure 59A:
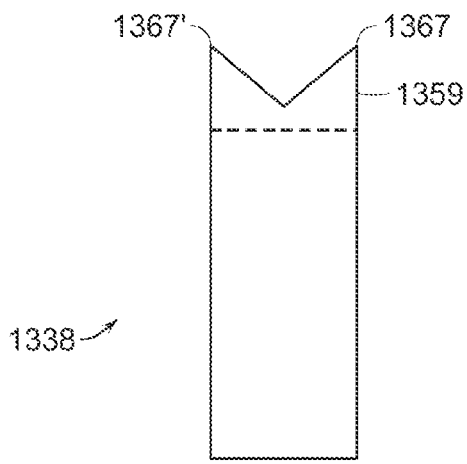
FIG. 59A is an elevation view of a rivet in an undeformed, unmelted, and/or undeployed state in accordance with one non-limiting embodiment of the present disclosure.
Figure 59B:
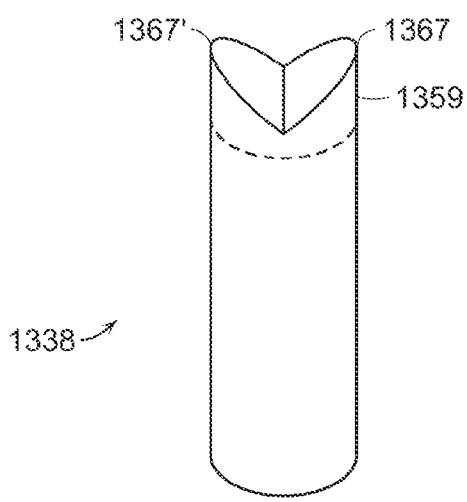
FIG. 59B is a perspective view of the rivet of FIG. 59A in accordance with one non-limiting embodiment of the present disclosure.
Figure 59C:
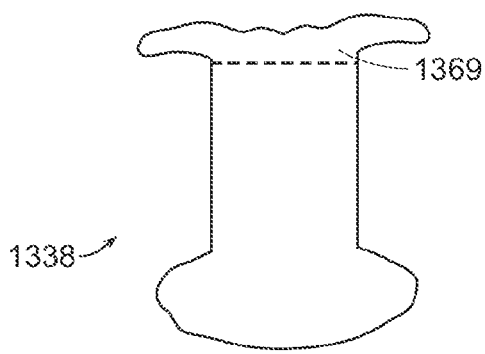
FIG. 59C is an elevation view of the rivet of FIGS. 59A and 59B in a melted, deformed, and/or deployed state in accordance with one non-limiting embodiment of the present disclosure.

In one embodiment, referring to FIGS. 59A-59C, a rivet 1338 is provided. The rivet 1338 is illustrated in the undeployed, undeformed, and/or unmelted state in FIGS. 59A and 59B and is illustrated, in one example embodiment, in a deployed, deformed, and/or melted state in FIG. 59C. In one embodiment, the rivet 1338 can be similar to the rivet 1238, but can comprise two tissue-puncturing tips 1367 and 1367' and a differently shaped meltable and/or deformable portion 1359 configured to be formed into a rivet head 1369.

Although the rivets and rivet cartridges have been discussed herein with respect to the surgical instrument 910, it will be understood that the rivets and rivet cartridges disclosed herein can be used with other linear cutting instruments, other linear cutting and sealing instruments, or other circular stapling instruments, such as the circular stapling instrument 10, for example. In a circular stapling instrument, the rivet cartridge can be circular or substantially circular such that it can be positioned within a receiving slot defined in the first portion 26 or the second portion 28 of the surgical instrument 10, for example. In one embodiment, the rivet cartridges discussed herein can be disposable or reloadable after use.

While the present disclosure has been illustrated by description of several example embodiments and while the example embodiments have been described in considerable detail, it is not the intention of the applicants to restrict or in any way limit the scope of the appended claims to such detail. Additional advantages and modifications may be readily apparent to those of skill in the art. Furthermore, although the example embodiments disclosed herein have been described in connection with various surgical instrument, other embodiments are envisioned in connection with other suitable medical devices and/or surgical instruments, such as a linear cutter for open surgery techniques, as disclosed in U.S. Patent Application Publication No. 2010/0072251 to Baxter et al., entitled LOCKOUT ARRANGEMENT FOR A SURGICAL STAPLER, filed on Sep. 19, 2008, the entire disclosure of which is hereby incorporated by reference. Furthermore, adjustable staple formation height technology can be used with the present disclosure. Example embodiments of the adjustable staple formation height technology are disclosed in U.S. Patent Application Publication No. 2010/0032470 to Hess et al., entitled SURGICAL STAPLING SYSTEMS AND STAPLE CARTRIDGES FOR DEPLOYING SURGICAL STAPLES WITH TISSUE COMPRESSION FEATURES, filed on Oct. 16, 2009, the entire disclosure of which is hereby incorporated by reference. While this disclosure has been described as having exemplary designs, the disclosure may be further modified within the spirit and scope of the disclosure. This application is therefore intended to cover any variations, uses, or adaptations of the disclosure using its general principles. Further, this disclosure is intended to cover such departures from the present disclosure as come within known or customary practice in the art to which this disclosure pertains.

The various embodiments of the present disclosure have been described above in connection with cutting-type surgical instruments. It should be noted, however, that in other embodiments, the surgical instruments disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc. In certain embodiments, an ultrasonic instrument can be utilized in accordance with the embodiments disclosed herein. In one such embodiment, an ultrasonic instrument can comprise a first portion comprising a handle portion and/or end effector, for example, and a second portion comprising radiation-sensitive electronics. Various ultrasonic instruments are disclosed in U.S. Pat. No. 6,063,098 to Houser et al., entitled ARTICULATABLE ULTRASONIC SURGICAL APPARATUS, which issued on May 16, 2000, the entire disclosure of which is hereby incorporated by reference in its entirety. Adjustable height staples and/or adjustable height staple formation technology may also be used with the embodiments of the present disclosure. An examples of such technology is disclosed in U.S. patent application Ser. No. 12/622,113 to Bedi et al., entitled SURGICAL STAPLER COMPRISING A STAPLE POCKET, filed on Nov. 19, 2009, the entire disclosure of which is incorporated herein by reference in its entirety. Although the present disclosure has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Further to the above, the various staple cartridges and/or rivet cartridges disclosed herein can be disposable. In one embodiment, an expended staple cartridge or rivet cartridge, or an at least partially expended staple cartridge or rivet cartridge, can be removed from a surgical stapler and replaced with another staple cartridge or rivet cartridge. In other various embodiments, the staple cartridge or rivet cartridge may not be removable and/or replaceable during the ordinary use of the surgical instrument but, in some circumstances, may be replaceable while and/or after the surgical stapler is reconditioned as described in greater detail below. In various embodiments, the staple cartridge or rivet cartridge can be part of a disposable loading unit or end-effector which can comprise a staple cartridge carrier or rivet cartridge carrier, an anvil, a cutting member, and/or a staple or rivet driver. In one embodiment, the entire, or at least a portion of, the disposable loading unit or end-effector can be detachably connected to a surgical instrument and can be configured to be replaced.

The surgical instruments disclosed herein can be designed to be disposed of after a single use, or they can be designed to be used multiple times. In either case, however, the surgical instruments can be reconditioned for reuse after at least one use. Reconditioning can comprise any combination of the steps of disassembly of the surgical instruments, followed by cleaning or replacement of particular pieces, and subsequent reassembly. In particular, the surgical instruments can be disassembled, and any number of the particular pieces or parts of the surgical instruments can be selectively replaced or removed in any combination. Upon cleaning and/or replacement of particular parts, the surgical instruments can be reassembled for subsequent use either at a reconditioning facility, or by a surgical team immediately prior to a surgical procedure. Those skilled in the art will appreciate that reconditioning of a surgical instrument can utilize a variety of techniques for disassembly, cleaning/replacement, and reassembly. Use of such techniques, and the resulting reconditioned surgical instrument, are all within the scope of the present disclosure.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An end-effector assembly configured to be attached to a surgical instrument, the end-effector assembly comprising:
   a first jaw;
   a second jaw comprising a staple cavity, wherein at least one of the first jaw and the second jaw is movable relative to the other jaw;
   a staple removably positioned within the staple cavity, wherein the staple comprises an electrode; and
   an electrically-conductive driver configured to move the staple between a first stored position in which the staple is at least partially positioned within the staple cavity and a second position in which the staple is at least partially deployed from the staple cavity into tissue positioned intermediate the first jaw and the second jaw.

2. The end-effector assembly of claim 1, wherein the electrode comprises a first electrode, and wherein one of the first jaw and the second jaw comprises a second electrode.

3. The end-effector assembly of claim 2, wherein the second electrode is positioned adjacent to a positive temperature coefficient material.

4. The end-effector assembly of claim 2, wherein the first electrode is configured to have a different polarity than the second electrode.

5. The end-effector assembly of claim 1, wherein the electrode comprises a first electrode, the end-effector assembly comprising a cutting member one of formed with and operably engaged with the electrically-conductive driver, wherein one of the first jaw and the second jaw comprises a second electrode, and wherein the cutting member comprises a third electrode.

6. The end-effector assembly of claim 1, wherein the electrically-conductive driver is in electrical communication with the electrode when moving the staple between the first position and the second position.

7. The end-effector assembly of claim 1, comprising a tissue thickness sensor configured to sense a thickness of the tissue positioned intermediate the first jaw and the second jaw, wherein the staple optionally remains in the first position when the sensed thickness is less than a predetermined tissue thickness threshold, and wherein the staple is moved into the second position when the sensed thickness is greater than the predetermined tissue thickness threshold.

8. The end-effector assembly of claim 7, comprising:
   a cutting member one of attached to and formed with the electrically-conductive driver, wherein the cutting member is movable along a cutting path to form a cut line in the tissue;
   a staple sensor configured to sense when the staple is in the first position; and
   a lockout device configured to selectively restrict movement of the cutting member along the cutting path when the sensed thickness is greater than the predetermined tissue thickness threshold and when the staple sensor indicates that the staple is not in the first position.

9. The end-effector assembly of claim 1, comprising:
   a cutting member configured to travel along a cutting path; and
   a resistive member configured to restrict the speed of the travel of the cutting member along the cutting path.

10. The end-effector assembly of claim 9, wherein the resistive member comprises one of a biasing member and a magnet.

11. The end-effector assembly of claim 1, wherein the electrode comprises a first electrode, the end-effector assembly comprising a staple cartridge comprising:
   the staple cavity;
   the staple; and
   a tissue-contacting surface, wherein the tissue-contacting surface comprises a second electrode.

12. The end-effector assembly of claim 1, comprising a staple cartridge comprising:
   a tissue-contacting surface having an outer perimeter;
   a first side;
   a second side;
   a cutting member slot defined at least partially intermediate the first side and the second side;
   a first plurality of staples at least partially positioned within a first plurality of staple cavities in the first side, wherein the first plurality staples form at least a first row of staples; and
   a second plurality of staples at least partially positioned within a second plurality of staple cavities in the second side, wherein the second plurality of staples form at least a second row of staples.

13. The end-effector assembly of claim 12, wherein the electrode comprises a first electrode, the end-effector assembly comprising a second electrode on the tissue-contacting surface, wherein the second electrode is positioned proximate to the outer perimeter of the tissue-contacting surface, and wherein the first row of staples and the second row of staples are positioned distal from the outer perimeter of the tissue-contacting surface.

14. The end-effector assembly of claim 12, wherein the electrode comprises a first electrode, the end-effector assembly comprising a second electrode on the tissue-contacting surface, wherein the first row of staples and the second row of staples are positioned proximate to the outer perimeter of the tissue-contacting surface, and wherein the second electrode is positioned distal from the outer perimeter of the tissue-contacting surface.

15. An end-effector assembly configured to be engaged with a surgical instrument, the end-effector assembly comprising:
   a first jaw;
   a second jaw comprising a staple cavity, wherein at least one of the first jaw and the second jaw is movable relative to the other jaw;
   a staple removably positioned within the staple cavity, wherein the staple comprises a first electrode; and
   an electrically-conductive driver configured to deploy the staple at least partially from the staple cavity into tissue positioned intermediate the first jaw and the second jaw; and
   wherein one of the first jaw and the second jaw comprises a second electrode.

16. The end-effector assembly of claim 15, wherein the staple comprises a first staple, the end-effector assembly comprising a second staple removably positioned within the staple cavity, wherein the second staple comprises a third electrode, and wherein the electrically-conductive driver is movable within the end-effector assembly between a first position in which the electrically-conductive driver is in electrical contact with the first staple and a second position in which the electrically-conductive driver is in electrical contact with the second staple.

17. The end-effector assembly of claim 15, wherein the first electrode is configured to have a different polarity than the second electrode, the end-effector assembly comprising a positive temperature coefficient material configured to selectively restrict an electrical current flow between the first electrode and the second electrode.

18. An end-effector assembly configured to be engaged with a surgical instrument, the end-effector assembly comprising:
   an electrode system comprising an electrode;
   a staple deploying system, comprising:
      a staple cavity;
      a staple removably positioned within the staple cavity; and
      a staple driver configured to move the staple between a first position in which the staple is stored at least partially within the staple cavity and a second position in which the staple is at least partially deployed from the staple cavity;
   a staple sensor configured to sense when the staple is in the first position;
   a tissue thickness sensor configured to sense a thickness of tissue positioned within the end-effector assembly; and
   a lockout device configured to deactivate the electrode system when the sensed thickness is greater than a predetermined tissue thickness threshold and when the staple sensor does not sense the staple in the first position.

19. The end-effector assembly of claim 18, wherein the electrode is a first electrode, wherein the staple comprises a second electrode, and wherein the staple driver comprises an electrically conductive portion configured to be placed in electrical contact with the second electrode.

20. The end-effector assembly of claim 18, wherein the staple deploying system is configured to deploy the staple into the tissue when the sensed thickness is greater than the predetermined tissue thickness threshold and when the staple sensor senses the staple in the first position.

21. An end-effector assembly configured to be attached to a surgical instrument, the end-effector assembly comprising:
   a first jaw;
   a second jaw, wherein at least one of the first jaw and the second jaw is movable relative to the other jaw;
   a staple removably positioned within the second jaw, wherein the staple comprises an electrode; and
   an electrically-conductive driver configured to deploy the staple into tissue positioned intermediate the first jaw and the second jaw.

22. The end-effector assembly of claim 21, wherein one of the first jaw and the second jaw comprises a second electrode.

23. An end-effector assembly configured to be engaged with a surgical instrument, the end-effector assembly comprising:
   an electrode system comprising an electrode;
   a staple deploying system, comprising:
      a staple cavity;
      a staple removably positioned within the staple cavity; and
      a staple driver configured to move the staple between a first position in which the staple is stored at least partially within the staple cavity and a second position in which the staple is at least partially deployed from the staple cavity;
   a staple sensor configured to sense when the staple is in the first position;
   a tissue thickness sensor configured to sense a thickness of tissue positioned within the end-effector assembly; and
   a lockout device configured to deactivate the electrode system when at least one of the sensed thickness is greater than a predetermined tissue thickness threshold and the staple sensor does not sense the staple in the first position.

24. A staple cartridge for use with a surgical instrument comprising a first jaw and a second jaw, the staple cartridge comprising:
    a cartridge body, comprising:
        a staple removably positioned within the cartridge body, wherein the staple comprises an electrode; and
        an electrically-conductive driver configured to deploy the staple into tissue positioned intermediate the first jaw and the second jaw.

* * * * *